United States Patent [19]

Whittaker et al.

[11] Patent Number: 5,200,412
[45] Date of Patent: Apr. 6, 1993

[54] HETEROBICYCLIC CONTAINING BENZENE SULFONAMIDES WHICH ARE PLATELET ACTIVATING FACTOR ANTAGONISTS

[75] Inventors: Mark Whittaker; Andrew Miller, both of Oxfordshire, England

[73] Assignee: British Bio-Technology Limited, Oxford, England

[21] Appl. No.: 745,471

[22] Filed: Aug. 15, 1991

[30] Foreign Application Priority Data

Aug. 15, 1990 [GB] United Kingdom ............... 9017878
Aug. 16, 1990 [GB] United Kingdom ............... 9018040
Jun. 14, 1991 [GB] United Kingdom ............... 9112857

[51] Int. Cl.⁵ ............... C07D 235/06; C07D 235/07; C07D 471/04; A61K 31/435; A61K 31/415
[52] U.S. Cl. ............... 514/293; 514/303; 514/394; 514/395; 546/82; 546/118; 548/306.1; 548/302.1; 548/306.4; 548/307.1; 548/310.1; 548/310.4; 548/304.4
[58] Field of Search ............... 546/82, 118; 548/325, 548/326, 329, 330, 332, 333, 334; 514/293, 303, 394, 395

[56] References Cited

FOREIGN PATENT DOCUMENTS

90/09997 9/1990 World Int. Prop. O. .......... 548/325

Primary Examiner—Bernard Dentz
Attorney, Agent, or Firm—Allegretti & Witcoff

[57] ABSTRACT

Compounds of general formula I;

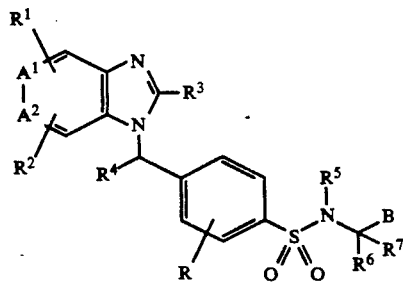

wherein:
$A^1$ is =N—, =CH— or =CR$^1$—;
$A^2$ is —N=, —CH= or —CR$^2$=;
provided that, when one of $A^1$ and $A^2$ is a nitrogen atom, the other of $A^1$ and $A^2$ is other than a nitrogen atom;
the rest of the variables are described in the specification;
and their pharmaceutically and veterinarily acceptable acid addition salts and hydrates are antagonists of platelet activating factor (PAF) and as such are useful in the treatment or amelioration of various diseases or disorders mediated by PAF.

20 Claims, No Drawings

HETEROBICYCLIC CONTAINING BENZENE SULFONAMIDES WHICH ARE PLATELET ACTIVATING FACTOR ANTAGONISTS

This invention relates primarily to novel compounds which are antagonists of platelet activating factor.

Platelet Activating Factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds which have been disclosed as possessing activity as PAF antagonists include compounds which are structurally related to the PAF molecule such as glycerol derivatives (EP-A-0238202), and heterocyclic compounds such as 2,5-diaryl tetrahydrofurans (EP-A-44804) and imidazopyridine derivatives (EP-A-0260613 and WO-A-908653).

The present invention provides novel and useful substituted amino acid derivatives and their pharmaceutically acceptable acid addition salts, and pharmaceutical uses thereof as PAF. antagonists.

According to a first aspect of the invention there is provided a compound of general formula I;

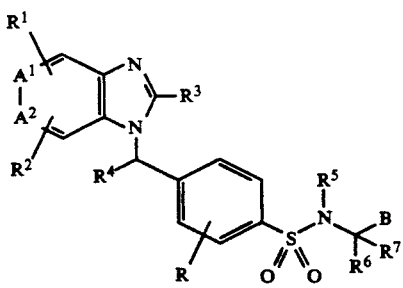

I wherein:
$A^1$ is =N—, =CH— or =CR$^1$—;
$A^2$ is —N=, —CH= or —CR$^2$=;
provided that, when one of $A^1$ and $A^2$ is a nitrogen atom, the other of $A^1$ and $A^2$ is other than a nitrogen atom;
R represents hydrogen, —$C_1$-$C_6$ alkyl, —$C_2$-$C_6$ alkenyl, halogen or —$OC_1$-$C_6$ alkyl;
each of $R^1$ and $R^2$ independently represents hydrogen, —$C_1$-$C_6$ alkyl, —$C_2$-$C_6$ alkenyl, halogen, —CN, —$CO_2$H, —$CO_2C_1$-$C_6$ alkyl, —$CONH_2$, —CHO, —$CH_2$OH, —$CF_3$, —$OC_1$-$C_6$ alkyl, —$SC_1$-$C_6$ alkyl, —$SOC_1$-$C_6$ alkyl, —$SO_2C_1$-$C_6$ alkyl, —$NH_2$, —NHCOMe or —$NO_2$ or $R^1$ and $R^2$ together with the carbon atoms to which they are attached form a fused phenyl ring;
$R^3$ represents hydrogen, —$C_1$-$C_6$ alkyl, —$C_2$-$C_6$ alkenyl, —$C_2$-$C_6$ alkynyl, —$OC_1$-$C_6$ alkyl, —$SC_1$-$C_6$ alkyl, —($C_1$-$C_6$ alkyl)$OC_1$-$C_6$ alkyl, —($C_1$-$C_6$ alkyl)$SC_1$-$C_6$ alkyl, —$CF_3$, —($C_1$-$C_6$ alkyl)phenyl, —$C_3$-$C_8$ cycloalkyl, —$C_4$-$C_8$ cycloalkenyl, —($C_1$-$C_6$ alkyl) $C_3$-$C_8$ cycloalkyl, —($C_1$-$C_6$ alkyl)$C_4$-$C_8$ cycloalkenyl or thiophenyl;
$R^4$ represents hydrogen, —$C_1$-$C_6$ alkyl, —$C_2$-$C_6$ alkenyl, —$C_2$-$C_6$ alkynyl, —$CO_2C_1$-$C_6$ alkyl, —$SC_1$-$C_6$ alkyl, —($C_1$-$C_6$ alkyl)$SC_1$-$C_6$ alkyl, —($C_1$-$C_6$ alkyl)$OC_1$-$C_6$ alkyl, —($C_1$-$C_6$ alkyl)phenyl or thiophenyl;
$R^5$ represents hydrogen, —$C_1$-$C_6$ alkyl, —$C_2$-$C_6$ alkenyl, —$C_2$-$C_6$ alkynyl, —$COC_1$-$C_6$ alkyl, —$CO_2C_1$-$C_6$ alkyl, —($COC_1$-$C_6$ alkyl)phenyl, —($CO_2C_1$-$C_6$ alkyl)phenyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)$CO_2C_1$-$C_6$ alkyl, —$C_3$-$C_8$ cycloalkyl, —$C_4$-$C_8$ cycloalkenyl or a group —D wherein D represents a group:

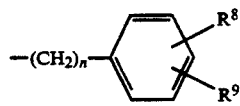

wherein n is an integer from 0 to 3, and each of $R^8$ and $R^9$ is independently hydrogen, —$C_1$-$C_6$ alkyl, —$C_2$-$C_6$ alkenyl, —$C_2$-$C_6$ alkynyl, halogen, —CN, —$CO_2$H, —$CO_2C_1$-$C_6$ alkyl, —$CONH_2$, —$CONH$-$C_1$-$C_6$ alkyl, —$CONH(C_1$-$C_6$ alkyl)$_2$, —CHO, —$CHO_2$H, —$CF_3$, —$OC_1$-$C_6$ alkyl, —$SC_1$-$C_6$ alkyl, —$SOC_1$-$C_6$ alkyl, —$SO_2C_1$-$C_6$ alkyl, —$NH_2$ or —NHCOMe;

each of $R^6$ and $R^7$ independently represents hydrogen, halogen, —$C_1$-$C_6$ alkyl optionally substituted by one or more halogen atoms, —$C_2$-$C_6$ alkenyl, —$C_2$-$C_6$ alkynyl, —($C_1$-$C_6$ alkyl)$CO_2C_1$-$C_6$ alkyl, —($C_1$-$C_6$ alkyl)$SC_1$-$C_6$ alkyl, —($C_1$-$C_6$ alkyl)$OC_1$-$C_6$ alkyl, —($C_1$-$C_6$alkyl)$N(C_1$-$C_6$ alkyl)$_2$, —$C_3$-$C_8$ cycloalkyl, —$C_4$-$C_8$ cycloalkenyl, —($C_1$-$C_6$ alkyl)$C_3$-$C_8$ cycloalkyl, —($C_1$-$C_6$ alkyl)$C_4$-$C_8$ cycloalkenyl, —($C_1$-$C_6$ alkyl)$OC_3$-$C_8$ cycloalkyl, —($C_1$-$C_6$ alkyl)$OC_4$-$C_8$ cycloalkenyl, —($C_1$-$C_6$ alkyl)$SC_3$-$C_8$ cycloalkyl, —($C_1$-$C_6$alkyl)$SC_4$-$C_8$ cycloalkenyl, a side chain of a naturally occurring amino acid, a group —D as defined above or a —($C_1$-$C_6$ alkyl)OD group wherein D is as defined above;

or $R^6$ together with $R^5$ and the atoms to which they are attached form a 5 to 8 membered nitrogen-containing heterocyclic ring;

or $R^6$ and $R^7$ together with the carbon atom to which they are attached form a $C_3$-$C_8$ cycloalkyl ring;

B represents a) a —$ZR^{10}$ group wherein Z is —C(-=O)—, —C(=O)O—, —C(=S)— or —C(=S)O— and $R^{10}$ is —$C_1$-$C_{18}$ alkyl optionally substituted by one or more halogen atoms, —$C_2$-$C_{18}$ alkenyl, —$C_2$-$C_{18}$ alkynyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)$O(C_1$-$C_6$ alkyl)$OC_1$-$C_6$ alkyl, —$C_3$-$C_8$ cycloalkyl, —$C_4$-$C_8$ cycloalkenyl, pyridyl, a group —D as defined above or a —($C_1$-$C_6$ alkyl)OD group wherein D is as defined above;

b) a —$CONR^{11}R^{12}$ group wherein each of $R^{11}$ and $R^{12}$ is independently hydrogen, —$C_1$-$C_{18}$alkyl optionally substituted by one or more halogen atoms, —$C_2$-$C_{18}$ alkenyl, —$C_2$-$C_{18}$ alkynyl, —$C_3$-$C_8$ cycloalkyl, —C-

4-C$_8$ cycloalkenyl, pyridyl, a group —D as defined above or R$^{11}$ and R$^{12}$ together with the nitrogen atom to which they are attached form a 5 to 8 membered nitrogen-containing heterocyclic ring;
or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "C$_1$-C$_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "C$_1$-C$_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to six carbon atoms may be preferred As used herein the term "C$_2$-C$_6$ alkenyl" refers to straight chain or branched chain hydrocarbon groups having from two to six carbon atoms and having in addition one doublebond, of either E or Z stereochemistry where applicable This term would include for example, vinyl, 1-propenyl, 1- and 2-butenyl and 2-methyl-2-propenyl.

As used herein the term "C$_2$-C$_{18}$ alkenyl" refers to straight chain or branched chain hydrocarbon groups having from two to eighteen carbon atoms and having in addition one or more double bonds, of either E or Z stereochemistry where applicable This term would include for example, vinyl, 1-propenyl, 1- and 2-butenyl, 2-methyl-2-propenyl, geranyl, and farnesyl. From two to six carbon atoms may be preferred.

As used herein the term "C$_2$-C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "C$_2$-C$_{18}$ alkynyl" refers to straight chain or branched chain hydrocarbon groups having from two to six carbon atoms and having in addition one triple bond This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

As used herein the term "OC$_1$-C$_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "SC$_1$-C$_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "C$_3$-C$_8$ cycloalkyl" refers to an alicyclic group having from 3 to 8 carbon atoms Illustrative of such cycloalkyl groups are cyclopropyl, cyclobutyl, cyclopentyl and cyclohexyl.

As used herein, the term "C$_4$-C$_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "naturally occurring amino acid" includes alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. The amino acids may have their sidechains protected for example the carboxyl groups of aspartic acid, glutamic acid and α-aminoadipic acid may be esterified (for example as a C$_1$-C$_6$ alkyl ester), the amino groups of lysine, ornithine, 5-hydroxylysine, 4-hydroxyproline may be converted to amides (for example as a COC$_1$-C$_6$ alkyl amide) or carbamates (for example as a C(=O)OC$_1$-C$_6$ alkyl or C(=O)OCH$_2$Ph carbamate), the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a C$_1$-C$_6$ alkyl or a (C$_1$-C$_6$ alkyl)phenyl ether) or esters (for example a C(=O)C$_1$-C$_6$ alkyl ester) and the thiol group of cysteine may be converted to thioethers (for example a C$_{1-C6}$ alky thioether) or thioesters (for example a C(=O)C$_1$-C$_6$ alkyl thioester).

As used herein, the term "nitrogen-containing heterocyclic ring" refers to an aromatic or alicyclic ring comprising one or more nitrogen atoms and optionally one or more other heteroatoms. Illustrative of such rings are pyrrolidine, piperidine, hexamethyleneimine, heptamethyleneimine, morpholine and piperazine.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts. p Preferred compounds include those in which, independently or in any compatible combination:
A$^1$ represents =N—, =CH— or =CR$^1$—;
A$^2$ represents —N=, —CH= or —CR$^2$=;
R represents a halogen (for example chlorine) atom or a hydrogen atom;
R$^1$ represents a halogen (for example fluorine) atom or a hydrogen atom;

$R^2$ represents a halogen (for example fluorine) atom or a hydrogen atom;

$R^3$ represents a hydrogen atom or a —$C_1$-$C_6$ alkyl (for example methyl, ethyl or n-pentyl) group;

$R^4$ represents a hydrogen atom;

$R^5$ represents a hydrogen atom, a —$C_1$-$C_6$ alkyl (for example methyl or propyl) group, a —$C_2$-$C_6$ alkenyl (for example allyl) group, a —$COC_1$-$C_6$ alkyl (for example acetyl) group, a —$CO_2C_1$-$C_6$ alkyl (for example ethoxycarbonyl) group, or a —($C_1$-$C_6$ alkyl)-$CO_2C_1$-$C_6$ alkyl (for example methoxycarbonylmethyl, ethoxycarbonylmethyl or t-butoxycarbonylmethyl) group;

$R^6$ represents a hydrogen atom, a —$C_1$-$C_6$ alkyl (for example methyl, isopropyl, n-butyl, isobutyl or 2-methylpropyl) group, a —$C_2$-$C_6$ alkenyl (for example allyl) group, a —($C_1$-$C_6$ alkyl)$CO_2C_1$-$C_6$ alkyl (for example ethyl 3-propionate) group, a —($C_1$-$C_6$ alkyl)$SC_1$-$C_6$ alkyl (for example methylthioethylene) group, the side chain of a naturally occurring amino acid, a group —D or a —($C_1$-$C_6$ alkyl)OD group, or $R^5$ and $R^6$, and the atoms to which they are attached form a 5 to 8 membered nitrogen-containing heterocyclic (for example pyrrolidine) ring;

$R^7$ represents a hydrogen atom or a —$C_1$-$C_6$ alkyl (for example methyl) group, or together with $R^6$ and the carbon atom to which they are attached forms a $C_3$-$C_8$ cycloalkyl (for example cyclohexyl) ring;

when $R^6$ represents the side chain of a naturally occurring amino acid the preferred stereochemistry of the carbon atom to which $R^6$ and $R^7$ are attached is the same as that of the naturally occurring amino acid;

n represents an integer of 0 or 1;

$R^8$ represents a hydrogen atom or a —$OC_1$-$C_6$ alkyl (for example methoxy) group;

$R^9$ represents a hydrogen atom;

Z represents a —C(=O)— group or a —C(=O)O— group;

$R^{10}$ represents a —$C_1$-$C_{18}$ alkyl (for example methyl, ethyl, n-propyl, isopropyl, n-butyl, sec-butyl, tert-butyl or octadecyl) group a —$C_2$-$C_{18}$ alkenyl (for example allyl) group, a —($C_1$-$C_6$ alkyl)$OC_1$-$C_6$ alkoxy (for example 2-ethoxyethyl, 1-methyl-2-methoxyethyl) group, a —($C_1$-$C_6$ alkyl)O($C_1$-$C_6$ alkyl)$OC_1$-$C_6$ alkyl (for example 2-(2-ethoxyethoxyethyl) group, a group —D or a —($C_1$-$C_6$ alkyl)OD (for example 2-benzoxyethyl) group;

$R^{11}$ represents a —$C_1$-$C_6$ alkyl (for example methyl) group or a pyridyl (for example 2-pyridyl) group, or together with $R^{12}$ and the nitrogen atom to which they are attached forms a 5 to 8 membered nitrogen-containing heterocyclic (for example pyrrolidine or morpholine) ring; and $R^{12}$ represents a hydrogen atom.

Preferred side chains of naturally occurring amino acids include side chains of alanine, valine, isoleucine, leucine, phenylalanine, tyrosine, serine, methionine, and aspartic acid.

Particularly preferred compounds include those in which, independently or in any compatible combination:

$A^1$ represents —N=;
$A^2$ represents =N—;
R represents a halogen (for example chlorine) atom or a hydrogen atom;
$R^1$ represents a hydrogen atom;
$R^2$ represents a hydrogen atom;
$R^3$ represents a —$C_1$-$C_6$ alkyl (for example methyl, ethyl or n-pentyl) group;
$R^4$ represents a hydrogen atom;
$R^5$ represents a hydrogen atom or a —$C_1$-$C_6$ alkyl (for example methyl or propyl) group, a —$C_2$-$C_6$ alkenyl (for example allyl) group, a —$CO_2C_1$-$C_6$ alkyl (for example ethoxycarbonyl) group or a —($C_1$-$C_6$ alkyl)$CO_2C_1$-$C_6$ alkyl (for example methoxycarbonylmethyl, ethoxycarbonylmethyl or t-butoxycarbonylmethyl) group;
$R^6$ represents a —$C_1$-$C_6$ alkyl (for example methyl, isopropyl, n-butyl, isobutyl or 2-methylpropyl) group, a —$C_2$-$C_6$ alkenyl (for example allyl) group, a —($C_1$-$C_6$ alkyl)$CO_2C_1$-$C_6$ alkyl (for example ethyl 3-propionate) group, —($C_1$-$C_6$ alkyl)$SC_1$-$C_6$ alkyl (for example methylthioethylene) group or the side chain of a naturally occurring amino acid;
$R^7$ represents a hydrogen atom;
when $R^6$ represents the side chain of a naturally occurring amino acid the preferred stereochemistry of the carbon atom to which $R^6$ and $R^7$ are attached is the same as that of the naturally occurring amino acid;
n represents an integer of 1;
$R^8$ represents a hydrogen atom;
$R^9$ represents a hydrogen atom;
B represents a —$ZR^{10}$ group;
Z represents a —C(=O)O— group;
$R^{10}$ represents a —$C_1$-$C_{18}$ alkyl (for example methyl, ethyl, n-propyl, isopropyl, n-butyl, sec-butyl, tert-butyl or octadecyl) group, a —$C_2$-$C_{18}$ alkenyl (for example allyl) group, a —($C_1$-$C_6$ alkyl)$OC_1$-$C_6$ alkyl (for example 2-ethoxyethyl, 1-methyl-2-methoxyethyl) group, —($C_1$-$C_6$ alkyl)O($C_1$-$C_6$ alkyl)$OC_1$-$C_6$ alkyl (for example 2-(2-ethoxyethoxyethyl) group, a group —D or a —($C_1$-$C_6$ alkyl)OD (for example 2-benzoxyethyl) group.

Particularly preferred side chains of naturally occurring amino acids include side chains of isoleucine, leucine and methionine.

Exemplary compounds include
1. N-4-(1H-2-Methylbenzimidazolylmethyl)phenylsulphonylglycine methyl ester,
2. N-4-(1H-2-Methylbenzimidazolylmethyl)phenylsulphonyl-2,2dimethylglycine methyl ester,
3. N-4-(1H-2-Methylbenzimidazolylmethyl)phenylsulphonyl-1-aminocyclohexanecarboxylic acid methyl ester,
4. N-4-(1H-2-Methylbenzimidazolylmethyl)phenylsulphonyl-L-2-phenylglycine methyl ester,
5. N-4-(1H-2-Methylbenzimidazolylmethyl)phenylsulphonyl-L-valine methyl ester,
6. N-4-(1H-2-Methylbenzimidazolylmethyl)phenylsulphonyl-L-isoleucine methyl ester,
7. N-4-(1H-2-Methylbenzimidazolylmethyl)phenylsulphonyl-L-leucine methyl ester,
8. N-4-(1H-2-Methylbenzimidazolylmethyl)phenylsulphonyl-D-leucine methyl ester,
9. N-4-(1H-2-Methylbenzimidazolylmethyl)phenylsulphonyl-L-norleucine methyl ester,
10. N-4-(1H-2-Methylbenzimidazolylmethyl)phenylsulphonyl-L-phenylalanine methyl ester,
11. N-4-(1H-2-Methylbenzimidazolylmethyl)phenylsulphonyl-O-methyl-L-tyrosine methyl ester,
12. N-4-(1H-2-Methylbenzimidazolylmethyl)phenylsulphonyl-O-benzyl-L-serine methyl ester,
13. N-4-(1H-2-Methylbenzimidazolylmethyl)phenylsulphonyl-L-methionine methyl ester, 14. N-4-(1H-2-Methylbenzimidazolylmethyl)phenylsulphonyl-L-leucine ethyl ester,
15. N-4-(1H-2-Methylbenzimidazolylmethyl)phenylsulphonyl-L-phenylalanine ethyl ester,
16. N-4-(1H-2-Methylbenzimidazolylmethyl)phenylsulphonyl-L-methionine ethyl ester,
17. N-4-(1H-2-Methylbenzimidazolylmethyl)phenylsulphonyl-L-aspartic acid diethyl ester,
18. N-4-(1H-2-Methylbenzimidazolylmethyl)phenylsulphonyl-L-leucine isopropyl ester,
19. N-4-(1H-2-Methylbenzimidazolylmethyl)phenylsulphonyl-L-leucine n-butyl ester,
20. N-4-(1H-2-Methylbenzimidazolylmethyl)phenylsulphonyl-L-alanine tert-butyl ester,
21. N-4-(1H-2-Methylbenzimidazolylmethyl)phenylsulphonyl-L-phenylalanine tert-butyl ester,
22. N-4-(1H-2-Methylbenzimidazolylmethyl)phenylsulphonyl-L-leucine benzyl ester,
23. N-4-(1H-2-Methylbenzimidazolylmethyl)phenylsulphonyl-L-phenylalanine benzyl ester,
24. N-4-(1H-2-Methylbenzimidazolylmethyl)phenylsulphonyl-L-isoleucine methylamide,
25. N-4-(1H-2-Methylbenzimidazolylmethyl)phenylsulphonyl-L-phenylalanine methylamide,
26. N-4-(1H-2-Methylbenzimidazolylmethyl)phenylsulphonyl-L-phenylalanine 2-pyridylamide,
27. N-4-(1H-2-Methylbenzimidazolylmethyl)phenylsulphonyl-L-phenylalanine morpholinoamide,
28. N-4-(1H-2-Methylbenzimidazolylmethyl)phenylsulphonyl-L-leucine pyrrolidinoamide,
29. N-4-(1H-2-Methylbenzimidazolylmethyl)phenylsulphonyl-L-prolinyl methyl ester,
30. N-4-(1H-2-Methylbenzimidazolylmethyl)phenylsulphonyl-L-prolinyl benzyl ester,
31. (A) N-4-(3H-Imidazo[4,5-c]pyridylmethyl)phenylsulphonyl-L-leucine methyl ester,
    (B) N-4-(1H-Imidazo[4,5-c]pyridylmethyl)phenylsulphonyl-L-leucine methyl ester,
32. (A) N-4-(3H-2-Methylimidazo[4,5-c]pyridylmethyl)phenylsulphonyl-L-leucine methyl ester,
    (B) N-4-(1H-2-Methylimidazo[4,5-c]pyridylmethyl)phenylsulphonyl-L-leucine methyl ester,
33. (A) N-4-(3H-Imidazo[4,5-c]pyridylmethyl)phenylsulphonyl-L-phenylalanine methyl ester,
    (B) N-4-(1H-Imidazo[4,5-c]pyridylmethyl)phenylsulphonyl-L-phenylalanine methyl ester,
34. (A) N-4-(3H-Imidazo[4,5-c]pyridylmethyl)phenylsulphonyl-O-benzyl-L-serine methyl ester,
    (B) N-4-(1H-Imidazo[4,5-c]pyridylmethyl)phenylsulphonyl-O-benzyl-L-serine methyl ester,
35. (A) N-4-(3H-2-Methylimidazo[4,5-c]pyridylmethyl)phenylsulphonyl-L-leucine ethyl ester,
    (B) N-4-(1H-2-Methylimidazo[4,5-c]pyridylmethyl)phenylsulphonyl-L-leucine ethyl ester,
36. (A) N-4-(3H-2-Methylimidazo[4,5-c]pyridylmethyl)phenylsulphonyl-L-leucine n-propyl ester,
    (B) N-4-(1H-2-Methylimidazo[4,5-c]pyridylmethyl)phenylsulphonyl-L-leucine n-propyl ester,
37. (A) N-4-(3H-2-Methylimidazo[4,5-c]pyridylmethyl)phenylsulphonyl-L-leucine allyl ester,
    (B) N-4-(1H-2-Methylimidazo[4,5-c]pyridylmethyl)phenylsulphonyl-L-leucine allyl ester,
38. (A) N-4-(3H-2-Methylimidazo[4,5-c]pyridylmethyl)phenylsulphonyl-L-leucine i-propyl ester,
    (B) N-4-(1H-2-Methylimidazo[4,5-c]pyridylmethyl)phenylsulphonyl-L-leucine i-propyl ester,
39. (A) N-4-(3H-2-Methylimidazo[4,5-c]pyridylmethyl)phenylsulphonyl-L-leucine n-butyl ester,
    (B) N-4-(1H-2-Methylimidazo[4,5-c]pyridylmethyl)phenylsulphonyl-L-leucine n-butyl ester,
40. (A) N-4-(3H-2-Methylimidazo[4,5-c]pyridylmethyl)phenylsulphonyl-L-leucine 1-methylpropyl ester,
    (B) N-4-(1H-2-Methylimidazo[4,5-c]pyridylmethyl)phenylsulphonyl-L-leucine 1-methylpropyl ester,
41. (A) N-4-(3H-2-Methylimidazo[4,5-c]pyridylmethyl)phenylsulphonyl-L-leucine benzyl ester,
    (B) N-4-(1H-2-Methylimidazo[4,5-c]pyridylmethyl)phenylsulphonyl-L-leucine benzyl ester,
42. (A) N-4-(3H-2-Methylimidazo[4,5-c]pyridylmethyl)phenylsulphonyl-L-leucine 2-ethoxyethyl ester,
    (B) N-4-(1H-2-Methylimidazo[4,5-c]pyridylmethyl)phenylsulphonyl-L-leucine 2-ethoxyethyl ester,
43. (A) N-4-(3H-2-Methylimidazo[4,5-c]pyridylmethyl)phenylsulphonyl-L-leucine 2-benzoxyethyl ester,
    (B) N-4-(1H-2-Methylimidazo[4,5-c]pyridylmethyl)phenylsulphonyl-L-leucine 2-benzoxyethyl ester,
44. (A) N-4-(3H-2-Methylimidazo[4,5-c]pyridylmethyl)phenylsulphonyl-L-leucine 1-methyl-2-methoxyethyl ester,
    (B) N-4-(1H-2-Methylimidazo[4,5-c]pyridylmethyl)phenylsulphonyl-L-leucine 1-methyl-2-methoxyethyl ester,
45. (A) N-4-(3H-2-Methylimidazo[4,5-c]pyridylmethyl)phenylsulphonyl-L-leucine 2-(2-ethoxyethoxy)ethyl ester,
    (B) N-4-(1H-2-Methylimidazo[4,5-c]pyridylmethyl)phenylsulphonyl-L-leucine 2-(2-ethoxyethoxy)ethyl ester,
46. (A) N-4-(3H-2-Methylimidazo[4,5-c]pyridylmethyl)phenylsulphonyl-D,L-allylglycine ethyl ester,
    (B) N-4-(1H-2-Methylimidazo[4.,5-c]pyridylmethyl)phenylsulphonyl-D,L-allylglycine ethyl ester,
47. (A) N-4-(3H-2-Methylimidazo[4,5-c]pyridylmethyl)phenylsulphonyl-L-methionine ethyl ester,
    (B) N-4-(1H-2-Methylimidazo[4,5-c]pyridylmethyl)phenylsulphonyl-L-methionine ethyl ester,
48. (A) N-4-(1H-2-Methyl-5-fluorobenzimidazolylmethyl)phenylsulphonyl-L-leucine methyl ester,
    (B) N-4-(1H-2-Methyl-6-fluorobenzimidazolylmethyl)phenylsulphonyl-L-leucine methyl ester,
49. (A) N-4-(1H-2-Methyl-5-fluorobenzimidazolylmethyl)phenylsulphonyl-L-leucine ethyl ester,
    (B) N-4-(1H-2-Methyl-6-fluorobenzimidazolylmethyl)phenylsulphonyl-L-leucine ethyl ester,
50. N-4-(1H-2-Methylbenzimidazolylmethyl)phenylsulphonyl-2-keto-3-amino-4-methylpentane,
51. (A) N-4-(3H-2-Methylimidazo[4,5-c]pyridylmethyl)phenylsulphonyl-2-keto-3-amino-4-methylpentane,
    (B) N-4-(1H-2-Methylimidazo[4,5-c]pyridylmethyl)phenylsulphonyl-2-keto-3-amino-4-methylpentane,
52. N-Methyl-N-4-(1H-2-methylbenzimidazolylmethyl)phenylsulphonyl-L-leucine methyl ester,
53. (A) N-Methyl-N-4-(3H-2-methylimidazo[4,5-c]pyridylmethyl)phenylsulphonyl-L-leucine ethyl ester,
    (B) N-Methyl-N-4-(1H-2-methylimidazo[4,5-c]pyridylmethyl)phenylsulphonyl-L-leucine ethyl ester,
54. N-Methyl-N-4-(1H-2-methylbenzimidazolylmethyl)phenylsulphonyl-L,-leucine ethyl ester,
55. (A) N-Methyl-N-4-(3H-imidazo[4,5-c]pyridylmethyl)phenylsulphonyl-L-leucine ethyl ester, (B) N-Methyl-N-4-(1H-imidazo[4,5-c]pyridylmethyl)phenylsulphonyl-L-leucine ethyl ester, 56. (A) N-Methyl-N-4-(3H-2-methylimidazo[4,5-c]pyridylmethyl)phenylsulphonyl-L-leucine i-propyl ester,
 (B) N-Methyl-N-4-(1H-2-methylimidazo[4,5-c]pyridylmethyl)phenylsulphonyl-L-leucine i-propyl ester, 57. (A) N-Methyl-N-4-(3H-2-methylimidazo[4,5-c]pyridylmethyl)phenylsulphonyl-L-leucine n-butyl ester,
 (B) N-Methyl-N-4-(1H-2-methylimidazo[4,5-c]pyridylmethyl)phenylsulphonyl-L-leucine n-butyl ester, 58. (A) N-Methyl-N-4-(3H-2-methylimidazo[4,5-c]pyridylmethyl)phenylsulphonyl-L-leucine benzyl ester,
 (B) N-Methyl-N-4-(1H-2-methylimidazo[4,5-c]pyridylmethyl)phenylsulphonyl-L-leucine benzyl ester, 59. (A) N-Allyl-N-4-(3H-imidazo[4,5-c]pyridylmethyl)phenylsulphonyl-L-leucine ethyl ester,
 (B) N-Allyl-N-4-(1H-imidazo[4,5-c]pyridylmethyl)phenylsulphonyl-L-leucine ethyl ester, 60. (A) N-Allyl-N-4-(3H-2-methylimidazo[4,5-c]pyridylmethyl)phenylsulphonyl-L-leucine ethyl ester,
 (B) N-Allyl-N-4-(1H-2-methylimidazo[4,5-c]pyridylmethyl)phenylsulphonyl-L-leucine ethyl ester, 61. (A) N-Methyl-N-4-(3H-2-methylimidazo[4,5-c]pyridylmethyl)phenylsulphonyl-D,L-allylglycine methyl ester,
 (B) N-Methyl-N-4-(1H-2-methylimidazo[4,5-c]pyridylmethyl)phenylsulphonyl-D,L-allylglycine methyl ester, 62. (A) N-Methyl-N-4-(3H-2-methylimidazo[4,5-c]pyridylmethyl)phenylsulphonyl-D,L-allylglycine ethyl ester,
 (B) N-Methyl-N-4-(1H-2-methylimidazo[4,5-c]pyridylmethyl)phenylsulphonyl-D,L-allylglycine ethyl ester, 63. (A) N-Methyl-N-4-(3H-2-methylimidazo[4,5-c]pyridylmethyl)phenylsulphonyl-L-isoleucine allyl ester,
 (B) N-methyl-N-4-(1H-2-methylimidazo[4,5-c]pyridylmethyl)phenylsulphonyl-L-isoleucine allyl ester, 64. (A) N-Methyl-N-4-(3H-2-methylimidazo[4,5-c]pyridylmethyl)phenylsulphonyl-L-leucine morpholinoamide,
 (B) N-Methyl-N-4-(1H-2-methylimidazo[4,5-c]pyridylmethyl)phenylsulphonyl-L-leucine morpholinoamide, 65. N-Propyl-N-4-(3H-imidazo[4,5-c]pyridylmethyl)phenylsulphonyl-L-leucine ethyl ester, 66. N-Propyl-N-4-(3H-2-methylimidazo[4,5-c]pyridylmethyl)phenylsulphonyl-L-leucine ethyl ester, 67. N-Propyl-N-4-(1H-2-methylimidazo[4,5-c]pyridylmethyl)phenylsulphonyl-L-leucine ethyl ester, 68. (A) N-Methyl-N-4-(3H-2-methylimidazo[4,5-c]pyridylmethyl)phenylsulphonyl-2-keto-3-amino-4-methylpentane,
 (B) N-Methyl-N-4-(1H-2-methylimidazo[4,5-c]pyridylmethyl)phenylsulphonyl-2-keto-3-amino-4-methylpentane, 69. (A) N-t-Butoxycarbonylmethyl-N-4-(3H-2-methylimidazo[4,5-c]pyridylmethyl)phenylsulphonyl-L-leucine ethyl ester, (B) N-t-Butoxycarbonylmethyl-N-4-(1H-2-methylimidazo[4,5-c]pyridylmethyl)phenylsulphonyl-L-leucine ethyl ester, 70. (A) N-Ethoxycarbonylmethyl-N-4-(3H-2-methylimidazo[4,5-c]pyridylmethyl)phenylsulphonyl-L-leucine ethyl ester,
 (B) N-Ethoxycarbonylmethyl-N-4-(1H-2-methylimidazo[4,5-c]pyridylmethyl)phenylsulphonyl-L-leucine ethyl ester, 71. (A) N-Methoxycarbonylmethyl-N-4-(3H-2-methylimidazo[4,5-c]pyridylmethyl)phenylsulphonyl-L-leucine ethyl ester,
 (B) N-Methoxycarbonylmethyl-N-4-(1H-2-methylimidazo[4,5-c]pyridylmethyl)phenylsulphonyl-L-leucine ethyl ester, 72. (A) N-Methyl-N-3-chloro-4-(3H-2-methylimidazo[4,5-c]pyridylmethyl)phenylsulphonyl-L-leucine ethyl ester,
 (B) N-Methyl-N-3-chloro-4-(1H-2-methylimidazo[4,5-c]pyridylmethyl)phenylsulphonyl-L-leucine ethyl ester, 73. N-Methyl-N-4-(1H-2-ethylimidazo[4,5-c]pyridylmethyl)phenylsulphonyl-L-leucine ethyl ester, 74. N-Methyl-N-4-(1H-2-n-pentylimidazo[4,5-c]pyridylmethyl)phenylsulphonyl-L-leucine ethyl ester, 75. N-Acetyl-N-4-(3H-2-methylimidazo[4,5-c]pyridylmethyl)phenylsulphonyl-L-leucine ethyl ester, 76. (A) N-Ethoxycarbonyl-N-4-(3H-2-methylimidazo[4,5-c]pyridylmethyl)phenylsulphonyl-L-leucine ethyl ester,
 (B) N-Ethoxycarbonyl-N-4-(1H-2-methylimidazo[4,5-c]pyridylmethyl)phenylsulphonyl-L-leucine ethyl ester, 77. N-Methyl-N-4-(1H-2-methylimidazo[4,5-c]pyridylmethyl)phenylsulphonyl-L-leucine octadecyl ester.

Compounds of general formula 1 may be prepared by any suitable method known in the art and/or by the following process, which itself forms part of the invention.

According to a second aspect of the invention, there is provided a process for preparing a compound of general formula I as defined above, the process comprising:

(a) treating an imidazole derivative represented by general formula II

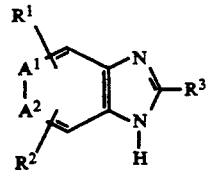

II wherein $A^1$, $A^2$, $R^1$, $R^2$ and $R^3$ are as defined in general formula I, with a suitable base (e.g. sodium hydride, potassium hydride, sodium bis(trimethylsilyl)amide, or potassium hydroxide), followed by a compound of general formula III

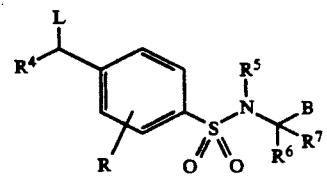

III wherein R, R⁴, R⁵, R⁶, R⁷, and B are as defined in general formula I, and L is chloro, bromo, iodo, methanesulphonyloxy, p-toluenesulphonyloxy or trifluoromethanesulphonyloxy; or (b) treating a substituted diamino compound of general formula I

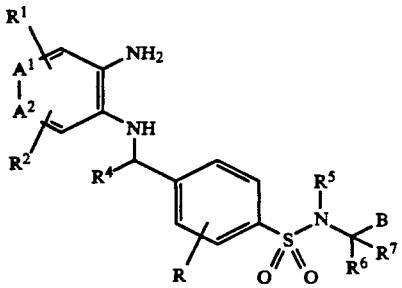

wherein $A^1$, $A^2$, R, $R^1$, $R^2$, $R^4$, $R^5$, $R^6$, $R^7$, and B are as defined in general formula I, with a carboxylic acid of general formula V $$R^3CO_2H \qquad V$$

wherein $R^3$ is as defined in general formula I, or a suitable derivative thereof; and (c) optionally after step (a) or step (b) converting, in one or a plurality of steps, a compound of general formula I into another compound of general formula I.

The reaction of step (a) can for preference be conducted in an aprotic solvent (e.g. tetrahydrofuran, N,N-dimethylformamide or acetonitrile) to yield compounds of general formula I. In the case where an unsymmetrically substituted imidazole derivative is used the reaction can yield an isomeric mixture, which is separated by chromatography to yield compounds of general formula I.

In step (b), derivatives of carboxylic acids of general formula V, which are suitable substrates for the reaction include acid halides of general formula VI $$R^3CO_2X \qquad VI$$

wherein $R^3$ is as defined in general formula I and X is fluoride, chloride, bromide or iodide, acid anhydrides of general formula VII $$(R^3CO)_2O \qquad VI$$

wherein $R^3$ is as defined in general formula I, trialkylorthoesters of general formula VIII

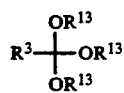 VIII wherein $R^3$ is as defined in general formula I and $R^{13}$ is —$C_1$-$C_6$ alkyl, or imino ether salts of general formula IX

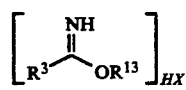 IX wherein $R^3$ is as defined in general formula I, $R^{13}$ is —$C_1$-$C_6$ alkyl and X is fluoride, chloride, bromide, or iodide. Carboxylic acids of general formula V, acid halides of general formula VI, acid anhydrides of general formula VII, trialkylorthoesters of general formula VIII and imino ether salts of general formula IX are available in the art or can be prepared by methods analogous to those known in the art.

By means of step (c) compounds of general formula I wherein B is a —$CONR^{11}R^{12}$ group wherein $R^{11}$ and $R^{12}$ are as defined for general formula I, may be prepared by the following methods;

i) by treatment of a compound of general formula I wherein B is a —$CO_2R^{10}$ group wherein $R^{10}$ is a benzyl group with hydrogen in the presence of a noble metal catalyst (e.g. 10% palladium on charcoal) to give a carboxylic acid which is then treated with an amine of general formula $HNR^{11}R^{12}$ in the presence of a coupling reagent (e.g. 1,3-dicyclohexylcarbodiimide);

ii) by treatment of a compound of general formula I wherein B is a —$CO_2R^{10}$ group wherein $R^{10}$ is lower alkyl with a dimethylaluminium amide of general formula X $$(Me)_2AlNR^{11}R^{12} \qquad X$$

wherein $R^{11}$ and $R^{12}$ are as defined in general formula I, which is prepared in situ from trimethylaluminium and an amine of general formula $HNR^{11}R^{12}$.

Also by means of step (c) certain compounds of general formula I wherein B is a —$CO_2R^{10}$ group wherein $R^{10}$ is as defined in general formula I, may be prepared by base catalysed hydrolysis to give a compound of general formula I wherein B is a —$CO_2H$ group which is subsequently esterified with an alcohol of general formula $HOR^{10}$ in the presence of a coupling reagent (e.g. 1,3-dicyclohexylcarbodiimide).

Also by means of step (c) certain compounds of general formula I wherein B is a —$CO_2R^{10}$ group wherein $R^{10}$ is as defined in general formula I or a $CONR^{11}R^{12}$ group wherein $R^{11}$ and $R^{12}$ are as defined in general formula I but are not hydrogen atoms, may be prepared by treatment of a compound of general formula I wherein $R^5$ is hydrogen with base followed by an electrophile of general formula XI $$LR^5 \qquad XI$$

wherein $R^5$ is as defined in general formula I but is not a hydrogen atom, a phenyl or a substituted phenyl group, and L is chloro, bromo, iodo, methanesulphonyloxy, p-toluenesulphonyloxy or trifluoromethanesulphonyloxy. Electrophiles of general formula VII are available in the art or can be prepared by procedures known to those skilled in the art.

Also by means of step (c) certain compounds of general formula I wherein $R^5$ is as defined in general formula I but is not a hydrogen atom, B is a —$CO_2R^{10}$ group wherein $R^{10}$ is as defined in general formula I or a —$CONR^{11}R^{12}$ group wherein $R^{11}$ and $R^{12}$ are as defined in general formula I but are not hydrogen atoms, can be prepared by treatment of a compound of general formula I wherein $R^4$ is a hydrogen atom with a suitable base (e.g. sodium bis(trimethylsilyl)amide) in an aprotic solvent (e.g. tetrahydrofuran) followed by an electrophile of the general formula $LR^4$ wherein $R^4$ is —$C_1$-$C_6$ alkyl, —$C_3$-$C_6$ alkenyl, —$C_3$-$C_6$ alkynyl, —$CO_2C_1$-$C_6$ alkyl, —($C_1$-$C_6$ alkyl)$SC_1$-$C_6$ alkyl, —($C_1$-$C_6$ alkyl)$OC_1$-$C_6$ alkoxy or —($C_1$-$C_6$ alkyl)phenyl and L is chloro, bromo, iodo, methanesulphonyloxy, p- toluenesulphonyloxy or trifluoromethanesulphonyloxy or by a $C_1$-$C_6$ alkyl disulphide or phenyl disulphide electrophile Electrophiles of the general formula $LR^4$ and disulphide electrophiles are available in the art or can be prepared by methods analogous to those known in the art.

Imidazole derivatives of general formula II may be prepared by a number of methods. The first method involves treatment of a 1,2-diamine of general formula XII

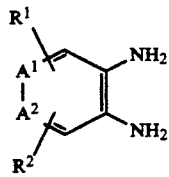

XII wherein $A^1$, $A^2$, $R^1$ and $R^2$ are as defined in general formula I, with a carboxylic acid of general formula V, an acid halide of general formula VI, an acid anhydride of general formula VII, a trialkylorthoester of general formula VIII or an imino ether salt of general formula IX.

1,2—Diamines of general formula XII are available in the art or may be prepared by the reduction of a 1,2-nitroamine of general formula XIII

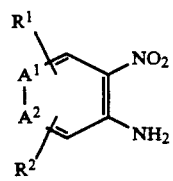

XIII wherein $A^1$, $A^2$, $R^1$ and $R^2$ are as in general formula I, for example in the presence of hydrogen and a catalyst such as palladium or platinum.

1,2-Nitroamines of general formula XIII are available in the art or can be prepared by methods analogous to those known in the art.

In a second method imidazole derivatives of general formula II may be prepared by the treatment of an 1,2-nitroamide of general formula XIV

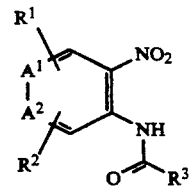

XIV wherein $A^1$, $A^2$, $R^1$, $R^2$ and $R^3$ are as defined in general formula I, with a suitable reducing agent (e.g. tin in acetic acid).

1,2-Nitroamides of general formula XIV may be prepared by the treatment of a 1,2-nitroamine of general formula XIII with an acid chloride of general formula VI wherein $R^3$ is as defined in general formula I, in an aprotic solvent and in the presence of a suitable base such as, for example, triethylamine. Alternatively, the reaction may be conducted utilising an acid anhydride of general formula VII wherein $R^3$ is as defined in general formula I.

Another procedure for preparing 1,2-nitroamides of general formula XIV involves reaction of a 1,2-nitroamine of general formula XIII with a carboxylic acid of general formula V, wherein $R^3$ is as defined in general formula I, in the presence of a coupling reagent (e.g. 1,3-dicyclohexylcarbodiimide).

Compounds of general formula III may be prepared by treatment of an amine of general formula XV

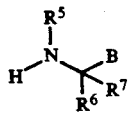

XV wherein $R^5$, $R^6$, $R^7$ and B are as defined in general formula I, with a sulphonyl halide of general formula XVI

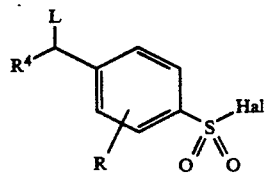

XVI wherein R and $R^4$ is as defined in general formula I, L is chloro, bromo, iodo, methanesulphonyloxy, p-toluenesulphonyloxy or trifluoromethanesulphonyloxy and Hal is a halide (e.g. fluoro, chloro or bromo), in the presence of a suitable base (e.g. triethylamine). Amines of general formula XV and sulphonyl halides of general formula XVI are known in the art or may be prepared by methods known in the art.

Substituted 1,2-diamines of general formula IV may be prepared by the reduction of a substituted 1,2-nitroamine of general formula XVII

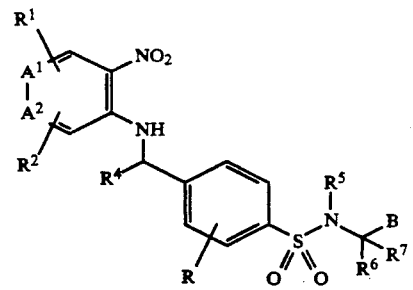

XVII wherein $A^1$, $A^2$, R, $R^1$, $R^2$, $R^4$, $R^5$, $R^6$, $R^7$, and B are as defined in general formula I, for example in the presence of hydrogen and a catalyst such as palladium or platinum.

Substituted 1,2-nitroamines of general formula XVII may be prepared by a number of methods. The first of these methods involves the treatment of a nitro compound of general formula XVIII

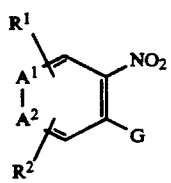

XVIII wherein $A^1$, $A^2$, $R^1$, and $R^2$ are as defined in general formula I and G is halo or $-OC_1-C_6$ alkyl, is treated with an amino compound of general formula XIX

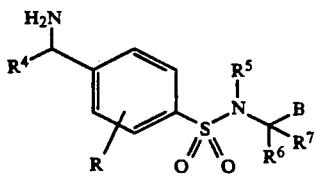

XIX wherein R, $R^4$, $R^5$, $R^6$, $R^7$ and B are as defined in general formula I. Nitro compounds of general formula XVIII are available in the art or can be prepared by methods analogous to those known in the art. Amino compounds of general formula XIX can be prepared by treatment of a compound of general formula III with hexamethylenetetramine followed by treatment with ethanolic hydrochloric acid or by sequential treatment of a compound of general formula III with sodium azide followed by either triphenylphosphine or hydrogenation over a suitable catalyst.

A second procedure for the preparation of substituted 1,2-nitroamines of general formula XVII involves the reduction of an imino nitro compound of general formula XX

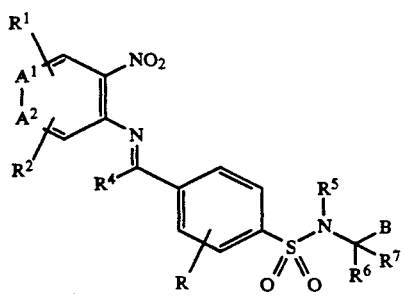

XX wherein $A^1$, $^2$, R, $R^1$, $R^2$, $R^4$, $R^5$, $R^6$, $R^7$ and B are as defined in general formula I, for example by the action of sodium cyanoborohydride.

The imino nitro compounds of general formula XX may be prepared by treating a 1,2-nitroamine of general formula XIII with a substituted carbonyl derivative of general formula XXI

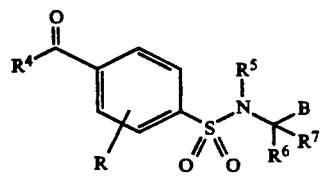

XXI wherein R, $R^5$, $R^6$, $R^7$ and B are as defined in general formula I and $R^4$ is as defined in general formula I but is not a $C_1-C_6$ alkylthio group. Substituted carbonyl derivatives of general formula XXI may be prepared by treatment of a compound of general formula III with an oxidising agent (e.g. dimethyl sulphoxide).

Alternatively substituted 1,2-nitroamines of general formula XVII in which $R^4$ is hydrogen may be prepared by the reduction of a 1,2-nitroamide of general formula XXII

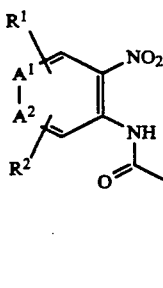

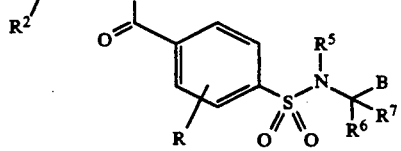

XXII wherein $A^1$, $A^2$, R, $R^1$, $R^2$, $R^5$, $R^6$, $R^7$ and B areas defined in general formula I, with a suitable metal hydride reducing agent such as for example lithium aluminium hydride.

The 1,2-nitroamides of general formula XXII may be prepared by the coupling of a 1,2-nitroamine of general formula XIII with an acid chloride of general formula XXIII

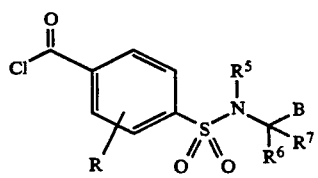

XXIII wherein R, $R^5$, $R^6$, $R^7$ and B are as defined in general formula I, in an aprotic solvent and in the presence of a suitable base such as, for example, triethylamine Alternatively, the reaction may be conducted utilising an acid anhydride of general formula XXIV

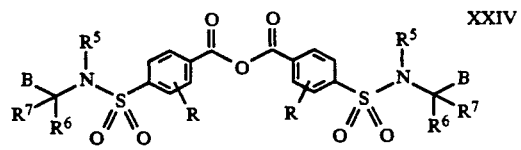

XXIV wherein R, $R^5$, $R^6$, $R^7$ and B are as defined in general formula I. Another procedure for preparing 1,2-nitroamides of general formula XXII involves reaction of a 1,2-nitroamine of general formula XIII with a carboxylic acid of general formula XXV

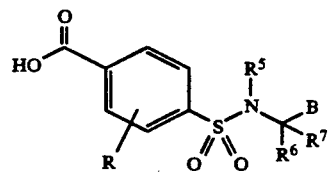

XXV wherein R, $R^5$, $R^6$, $R^7$ and B are as defined in general formula I, in the presence of a coupling reagent (e.g. 1,3-dicyclohexylcarbodiimide). Acid chlorides of general formula XXIII, acid anhydrides of general formula XXIV and carboxylic acids of general formula XXV may be prepared from carbonyl derivatives of general formula XXI wherein $R^4$ is hydrogen by procedures known to those skilled in the art.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, III and IV, XVII are valuable intermediates in the preparation of compounds of general formula I, as are other novel compounds specifically or generically disclosed herein. According to a third aspect of the invention, there is therefore provided a compound of general formula II. According to a fourth aspect of the invention, there is provided a compound of general formula III, According to a fifth aspect of the invention, there is provided a compound of general formula IV. According to a sixth aspect of the invention, there is provided a compound of general formula XVII.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient In addition to the treatment of warm blooded animals such as mice. rats, horses, cattle, pigs, sheep, dogs, cats, etc., the compounds of the invention are effective in the treatment of humans.

According to a seventh aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immunecomplex deposition and smooth muscle contractions.

According to an eighth aspect of the invention there is provided the use of a compound of general formula I in the preparation of an agent for the treatment of PAF-mediated diseases, and/or the treatment of inflammatory disorders; such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiplesclerosis, cerebral, myocardial and renal ischemia and any other condition in which PAF is implicated.

Compounds of general formula (I.) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a ninth aspect of the invention there is provided a pharmaceutical or veterinary formulation comprising a compound of general formula I and a pharmaceutically and/or veterinarily acceptable carrier One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc., The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions Such excipients are suspending agents, for example sodium carboxymethylcellulose , methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or bucal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents.

Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Pharmacological Example 1. The ability of compounds of general formula I to reverse the hypotension caused by an infusion of PAF in rats was measured according to Pharmacology Example 2.

The following examples illustrate the invention, but are not intended to limit the scope in any way.

The following abbreviations have been used in the

EXAMPLES

DCM—Dichloromethane
DIPE—Diisopropylether
DMF—N,N—Dimethylformamide
NBS—N-Bromosuccinimide
THF—Tetrahydrofuran Unless otherwise stated $^1$H NMR and $^{13}$C NMR spectra were recorded on a Bruker AC-250 spectrometer at 250 MHz and 62.9 MHz respectively using $CDCl_3$ as a solvent and internal reference and are reported as delta ppm from TMS.

EXAMPLE 1

N-4-(1H-2-Methylbenzimidazolylmethyl)phenylsulphonylglycine methyl ester

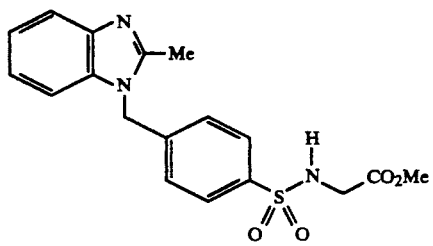

(a) 4-Bromomethylphenylsulphonylchloride

To a solution of p-toluenesulphonyl chloride (50 g, 0.26 mol) in benzene (150 ml) and NBS (46.7 g, 0.26 mol) heated at reflux was added 2,2'-azobis(2-methylpropionitrile) (100 mg). The mixture was heated at reflux for 12 h and allowed to cool to room temperature. The white precipitate of succinimide that formed was separated and discarded The filtrate was taken up in DCM (200 ml) and washed with water (3×100 ml) followed by brine (100 ml) and dried over anhydrous sodium sulphate. Filtration, concentration and subsequent crystallisation (from DIPE) gave in two crops 4-bromomethylphenylsulphonylchloride (46.3 g, 66%) as a white crystalline solid.

m.p. 75°-76° C.

delta$_H$ 8.02 (2H, d, J 8.5 Hz), 7.64 (2H, d, J 8.5 Hz), 4.52 (2H, s).

(b) N-4-Bromomethylphenylsulphonyl-glycine methyl ester

To a solution of triethylamine (13.3 ml, 0.096 mol) in dry THF (150 ml) was added powdered glycine methyl ester hydrochloride (6.0 g, 0.048 mol) in one portion. The mixture was stirred at room temperature for 0.5 h and powdered 4-bromomethylphenylsulphonyl chloride (12.9 g, 0.048 mol) added in one portion. The mixture was stirred overnight at room temperature. Saturated ammonium chloride (100 ml) was added and the mixture extracted with ethyl acetate (3×100 ml), the organics dried over anhydrous sodium sulphate, filtered and evaporated. The resulting oil was chromatographed (silica: 1:2 hexane:ethyl acetate) to give N-4-bromomethylphenylsulphonylglycine methyl ester (4.6 g, 28%) as a pale yellow oil.

delta$_H$ 7.80 (2H, d), 7.44 (2H, d), 5.66-5.60 (1H, m), 4.43 (2H, s), 3.79 (2H, d), 3.58 (3H, s).

(c) N-4-(1H-2-Methylbenzimidazolylmethyl)phenylsulphonylglycine methyl ester

Sodium hydride (60% dispersion in oil) (204 mg, 5.1 mmol) was added to a stirred solution of 2-methylbenzimidazole (637 mg, 4.8 mmol) in dry THF (25 ml) under argon at room temperature. After 1 h a solution of N-4-bromomethylphenylsulphonylglycine methyl ester (820 mg, 2.6 mmol) in dry THF (8 ml) was added. The mixture was stirred for 8 h and saturated ammonium chloride (60 ml) was added and the product extracted with ethyl acetate (3×60 ml). The combined organic layers were washed with water (2×50 ml), dried over anhydrous sodium sulphate, filtered and the solvent removed. Chromatography (silica: 5% methanol in chloroform) gave N-4-(1H-2-methylbenzimidazolylmethyl)phenyl-sulphonylglycine methyl ester (193 mg, 20%) as a white crystalline solid.

m.p. 135° C.

Analysis calculated for $C_{18}H_{19}N_3SO_4.0.9$ $H_2O$ Requires C 55.49 H 5.38 N 10.78.

Found C 55.48 H 5.05 N 10.70.

i.r. (KBr) 1740, 1325, 1150 cm$^{-1}$. delta$_H$ 7.82-7.68 (3H, m), 7.30-7.14 (5H, m), 5.65-5.50 (1H, m), 5.37 (2H, s), 3.78 (2H, d, J 5.2 Hz), 3.59 (3H, s), 2.56 (3H, s).

EXAMPLE 2

N-4-(1H-2-Methylbenzimidazolylmethyl)phenylsulphonyl-2,2-dimethylglycine methyl ester

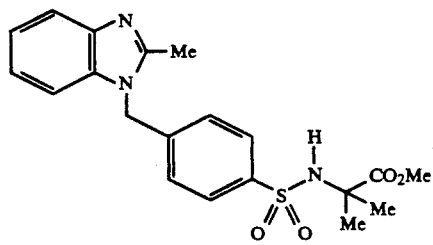

(a) 2,2-Dimethylglycine methyl ester hydrochloride

To a stirred solution of 2,2-dimethylglycine (10.0 g, 0.097 mol) in methanol (200 ml) was added trimethylsilyl chloride (37 ml, 0.29 mol). After stirring at room temperature for 14 h. The mixture was evaporated to dryness to give crude 2,2-dimethylglycine methyl ester hydrochloride as a white solid which was used directly in the next step.

delta$_H$ ($CD_3OD$) 4.80 (2H, br s), 3.81 (3H, s), 1.49 (6H, s).

(b) N-4-(1H-2-Methylbenzimidazolylmethyl)phenylsulphonyl-2,2-dimethylglycine methyl ester N-4-(1H-2-Methylbenzimidazolylmethyl)phenylsulphonyl-2,2-dimethylglycine methyl ester was prepared by the method of Example 1 starting from crude 2,2-dimethylglycine methyl ester hydrochloride.

White crystalline solid (20% yield for last step after chromatography (silica: 5% methanol in chloroform)): m.p. 200° C. (dec.)

Analysis calculated for $C_{20}H_{23}N_3SO_4$ Requires C 58.26 H 5.92 N 10.19. Found C 58.21 H 5.71 N 9.93.

i.r. (KBr) 1735, 1325, 1145 cm$^{-1}$.

delta$_H$ 7.85-7.72 (3H, m), 7.31-7.10 (5H, m), 5.39 (3H, br s), 3.64 (3H, s), 2.57 (3H, s), 1.43 (6H, s).

EXAMPLE 3

N-4-(1H-2-Methylbenzimidazolylmethyl)phenylsulphonyl-1-aminocyclohexanecarboxylic acid methyl ester

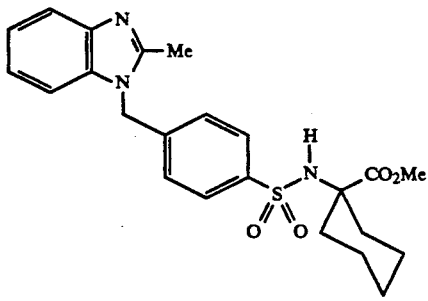

N-4-(1H-2-Methylbenzimidazolylmethyl)phenylsulphonyl-1-aminocyclohexanecarboxylic acid methyl ester was prepared by the method of Example 2 starting from 1-aminocyclohexanecarboxylic acid.

White crystalline solid (26% yield for last step after chromatography (silica; 5% methanol in chloroform)): m.p. 226° C. (sub.)

Analysis calculated for $C_{23}H_{27}N_3SO_4.0.9\ H_2O$ Requires C 60.35 H 6.34 N 9.18. Found C 60.29 H 5.98 N 9.10.

i.r (KBr) 1735, 1325, 1160 cm$^{-1}$.

delta$_H$ 7.84–7.73 (3H, m), 7.32–7.13 (5H, m), 5.40 (2H, s), 4.80 (1H, s), 3.49 (3H, s), 2.57 (3H, s), 1.90–1.78 (4H, m), 1.50–1.23 (6H, m).

EXAMPLE 4

N-4-(1H-2-Methylbenzimidazolylmethyl)phenylsulphonyl-L-2-phenylglycine methyl ester

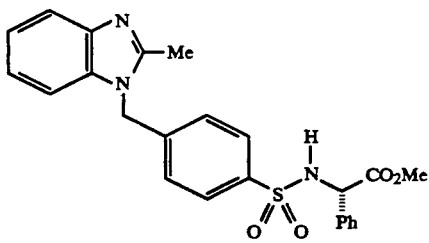

N-4-(1H-2-Methylbenzimidazolylmethyl)phenylsulphonyl-L-2-phenylglycine methyl ester was prepared by the method of Example 2 starting from L-2-phenylglycine.

White crystalline solid (42% yield for last step after chromatography (silica: 5% methanol in chloroform)): m.p. 50° C.

Analysis calculated for $C_{24}H_{23}N_3SO_4.0.8\ H_2O$ Requires C 62.13 H 5.34 N 9.06. Found C 62.19 H 5.26 N 8.81.

i.r. (KBr) 1740, 1325, 1160 cm$^{-1}$. delta$_H$ 7.79–7.73 (1H, m), 7.65–7.58 (2H, m), 7.32–6.98 (10H, m), 5.83 (1H, d, J 7.0 Hz), 5.32 (2H, s), 5.08 (1H, d, J 7.0 Hz), 3.55 (3H, s), 2.56 (3H, s).

EXAMPLE 5

N-4-(1H-2-Methylbenzimidazolylmethyl)phenylsulphonyl-L-valine methyl ester

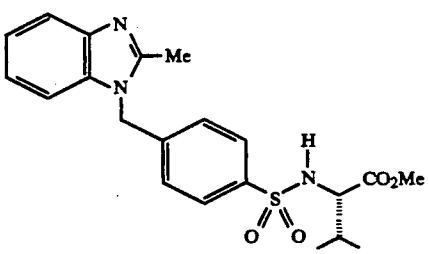

(a) N-4-Bromomethylphenylsulphonyl-L-valine methyl ester

To a stirred solution of L-valine methyl ester (2.2 g, 0.019 mol) and triethylamine (3.2 ml, 0.023 mol) in dry THF (75 ml) was added 4-bromomethylphenylsulphonyl chloride (5.5 g, 0.020 mol) in one portion. The mixture was stirred overnight at room temperature. The solvent was removed under reduced pressure, the residue dissolved in ethyl acetate (150 ml), washed with water (2×80 ml) and brine (80 ml), dried over anhydrous sodium sulphate, filtered and evaporated. Chromatography (silica: 1:2 hexane:ethyl acetate) gave N-4-bromomethylphenylsulphonyl-L-valine methyl ester (4.1 g, 76%) as a pale yellow oil.

delta$_H$ 7.83 (2H, d, J 8.4 Hz), 7.52 (2H, d, J 8.3 Hz), 5.05 (1H, d, J 10.1 Hz), 4.63 (2H, s), 3.76 (1H, m), 3.44 (3H, s), 2.06 (1H, m), 0 97 (3H, d, J 6 6 Hz), 0.89 (3H, d, J 6.6 Hz).

(b) N-4-(1H-2-Methylbenzimidazolylmethyl)phenylsulphonyl-L-valine methyl ester

Sodium bis(trimethylsilyl)amide (1M solution in THF: 15.5 ml, 0.015 mol) was added to a stirred solution of 2-methylbenzimidazole (1.86 g, 0.014 mol) in dry THF (80 ml) under argon at room temperature. After 10 min a solution of N-4-bromomethylphenylsulphonyl-L-valine methyl ester (4.0 g, 0.014 mol) in THF (25 ml) was added. The mixture was stirred overnight and the solvent removed under reduced pressure. The residue was partitioned between DCM (200 ml) and water (60 ml). The organics were dried over anhydrous sodium sulphate filtered and evaporated. Chromatography (silica: 3% methanol in DCM) followed by crystallisation from ethyl acetate gave N-4-(1H-2-methylbenzimidazolylmethyl)phenylsulphonyl-L-valine methyl ester (0.48 g, 8%) as a white crystalline solid.

m.p. 189° C.

Analysis calculated for $C_{21}H_{25}N_3SO_4$ Requires C 60.70 H 6.06 N 10.11. Found C 60.50 H 6.11 N 9.88.

delta$_H$ 8.20 (1H, br d), 7 72 (2H, d, J 8.4 Hz), 7.56 (1H, m), 7.33 (1H, m), 7.19 (4H, m), 5.52 (2H, s), 3.57 (1H, d, J 6.4 Hz), 3.16 (3H, s), 2.54 (3H, s), 1.91 (1H, m), 0.84 (3H, d, J 6.7 Hz), 0.83 (3H, d, J 6.8 Hz).

EXAMPLE 6

N-4-(1H-2-Methylbenzimidazolylmethyl)phenylsulphonyl-L-isoleucine methyl ester

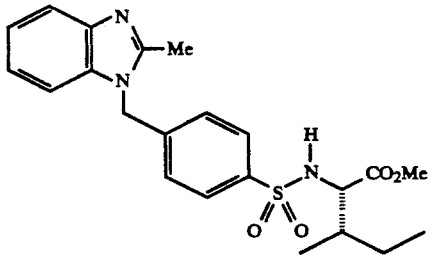

N-4-(1H-2-Methylbenzimidazolylmethyl)phenylsulphonyl-L-isoleucine methyl ester was prepared by the method of Example 2 starting from L-isoleucine.

White crystalline solid (20% yield for last step after chromatography (silica: 5% methanol in chloroform)): m.p. 197° C.

Analysis calculated for $C_{22}H_{27}N_3SO_4$ Requires C 61.52 H 6.34 N 9.78. Found C 61.16 N 6.31 N 9.73.

i.r. (KBr) 2960, 1735, 1325, 1165 $cm^{-1}$.

$delta_H$ 7.81–7.72 (3H, m), 7.33–7.10 (5H, m), 5.39 (2H, s), 5.14 (1H, d, J 10.0 Hz), 3.77 (1H, dd, J 10.0, 5.4 Hz), 3.33 (3H, s), 2.58 (3H, s), 1.82–1.70 (1H, m), 1.24–1.04 (2H, m), 0.95–0.80 (6H, m).

EXAMPLE 7

N-4-(1H-2-Methylbenzimidazolylmethyl)phenylsulphonyl-L-leucine methyl ester

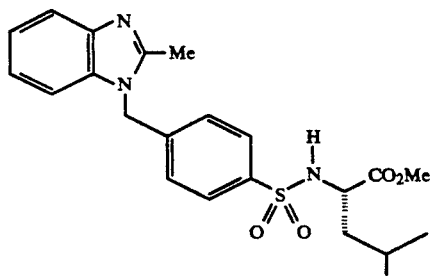

N-4-(1H-2-Methylbenzimidazolylmethyl)phenylsulphonyl-L-leucine methyl ester was prepared by the method of Example 5 starting from L-leucine methyl ester.

White crystalline solid (8% yield for last step after chromatography (silica: 3% methanol in DCM) and crystallisation from ethyl acetate/hexane) m.p. 201.5°–203° C.

Analysis calculated for $C_{22}H_{27}N_3SO_4$ Requires C 61.52 H 6.34 N 9.78. Found C 61.16 H 6.31 N 9.64.

i.r. (CHCl$_3$) 3360, 1740, 1350, 1160 $cm^{-1}$.

$delta_H$ 7.80–7.74 (3H, m), 7.31–7.08 (5H, m), 5.39 (2H, s), 5.08 (1H, d, J 10.0 Hz), 3.92 (1H, dt, J 10.0, 7.3 Hz) 3.34 (3H, s), 2.5S (3H, s), 1.82–1.67 (1H, m), 1.50 (2H, t, J 7.3 Hz), 0.88 (3H, d, J 6.6 Hz), 0.S5 (3H, d, J 6.5 Hz).

EXAMPLE 8

N-4-(1H-2-Methylbenzimidazolylmethyl)phenylsulphonyl—D-leucine methyl ester

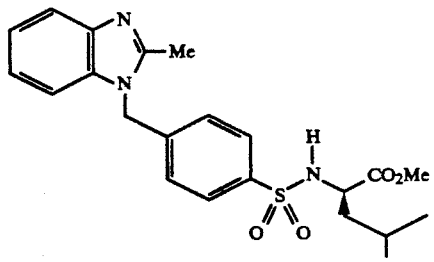

N-4-(1H-2-Methylbenzimidazolylmethyl)phenylsulphonyl—D-leucine methyl ester was prepared by the method of Example 5 starting from D-leucine methyl ester.

White crystalline solid (6% yield for last step after chromatography (silica: 3% methanol in DCM) and crystallisation from ethyl acetate) m.p. 204.5°–206.5° C.

Analysis calculated for $C_{22}H_{27}N_3SO_4$ Requires C 61.51 H 6.34 N 9.78. Found C 61.55 H 6.38 N 9.73.

$delta_H$ 7.80–7 74 (3H, m), 7.31–7.08 (5H, m), 5.39 (2H, s), 5.08. (1H, d, J 10.0 Hz), 3.92 (1H, dt, J 10 0, 7 3 Hz), 3.34 (3H, s), 2.58 (3H, s), 1.82–1.67 (1H, m), 1.50 (2H, t, J 7.3 Hz), 0.88 (3H, d, J 6.6 Hz), 0.85 (3H, d, J 6.5 Hz).

EXAMPLE 9

1H-2-Methylbenzimidazolylmethyl)phenylsulphonyl-L-norleucine methyl ester

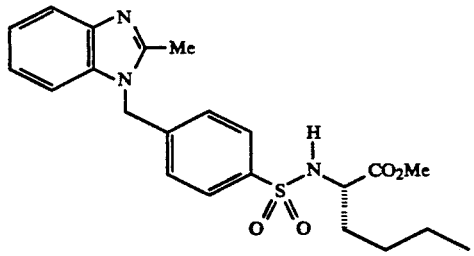

N-4-(1H-2-Methylbenzimidazolylmethyl)phenylsulphonyl-L-norleucine methyl ester was prepared by the method of Example 2 starting from L-norleucine.

White crystalline solid (10% yield for last step after chromatography (silica: 5% methanol in DCM) and crystallisation from ethyl acetate): m.p. 172° C.

Analysis calculated for $C_{22}H_{27}N_3SO_4$ Requires C 61.52 H 6.34 N 9.78. Found C 61.49 H 6.23 N 10.01.

i r. (KBr) 1750, 1330, 1160 $cm^{-1}$.

$delta_H$ 7.80–7.65 (3H, m), 7.30–7.06 (5H, m), 5.70 (1H, br d, J 8.4 Hz), 5.34 (2H, s), 3.95–3.80 (1H, m), 3.37 (3H, s), 2.55 (3H, s), 1.75–1.50 (2H, m), 1.32–1.16 (4H, m), 0.81 (3H, t, J 6.8 Hz).

EXAMPLE 10

N-4-(1H-2-Methylbenzimidazolylmethyl)phenylsulphonyl-L-phenylalanine methyl ester

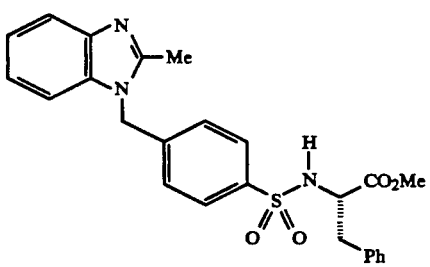

N-4-(1H-2-Methylbenzimidazolylmethyl)phenylsulphonyl-L-phenylalanine methyl ester was prepared by the method of Example 5 starting from L-phenylalanine methyl ester.

White crystalline solid (27% yield for last step after chromatography (silica: 2% methanol in DCM)): m.p. 126° C.

Analysis calculated for $C_{25}H_{25}N_3O_4S$ Requires C 64.77 H 5.44 N 9.07. Found C 64.60 H 5.51 N 9.04.

i.r. (KBr) 1735, 1340, 1150 cm$^{-1}$.

delta$_H$ 7.80–7.63 (3H, m), 7.34–6.99 (10H, m), 5.37 (2H, s), 5.04 (1H, d, J 9.2 Hz), 4.24–4.13 (1H, m), 3.45 (3H, s), 3.04 (1H, dd, J 13.8, 5.8 Hz), 2.98 (1H, dd, J 13.8, 6.3 Hz), 2.57 (3H, s).

EXAMPLE 11

N-4-(1H-2-Methylbenzimidazolylmethyl)phenylsulphonyl-O-methyl-L-tyrosine methyl ester

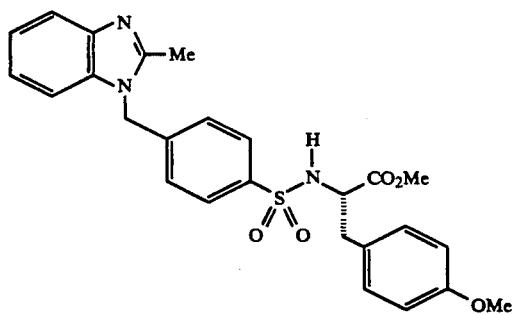

(a) N-Benzyloxycarbonyl-O-methyl-L-tyrosine

N-Benzyloxycarbonyl-L-tyrosine (31.5 g, 0.1 mol) was dissolved in aqueous sodium hydroxide (10 g in 100 ml H$_2$O) and dimethylsulphate (10.5 ml, 0.11 mol) added dropwise to the stirred solution. The reaction was stirred overnight, additional dimethylsulphate (2 ml) added in one portion and the reaction stirred for a further 48 hours. 2M Hydrochloric acid was added until a white precipitate formed. This was filtered off, taken up in ethyl acetate, washed with brine and dried over anhydrous sodium sulphate, filtered and evaporated. The residue was crystallised from ethyl acetate to give N-benzyloxycarbonyl-O-methyl-L-tyrosine (5.8 g, 18%) as a white crystalline solid.

m.p. 106°-b 108° C.

delta$_H$ 7.26–6.96 (7H, m), 6.98 (2H, d, J 8.0 Hz), 5.61 (1H, s), 5.00 (1H, br d), 4.77 (1H, br d), 4.40 (1H, br m), 3.63 (3H, s), 3.09 (1H, br m), 2.84 (1H, br m).

(b) O-Methyl-L-tyrosine

N-Benzyloxycarbonyl-O-methyl-L-tyrosine (5.7g, 17.3 mmol) was dissolved in ethanol (50 ml) and the solution added to a suspension of 10% palladium on charcoal (100 mg) in cyclohexene (10 ml). The reaction was then heated at reflux for 1 h, allowed to cool to ambient temperature, filtered, and the filtrate concentrated to give O-methyl-L-tyrosine (1.4 g, 43%) as a white solid which was used directly in the next step.

(c) O-Methyl-L-tyrosine methyl ester

A solution of O-methyl-L-tyrosine (1.44 g, 7.4 mmol) in methanol (30 ml) was stirred at 0° C. and thionyl chloride (1 ml, 13.4 mmol) added dropwise. After stirring for 15 min. at ambient temperature the reaction was heated at reflux for 2 h. After cooling the solvent was evaporated to give crude O-methyl-L-tyrosine methyl ester hydrochloride salt as a yellow solid This was partitioned between saturated aqueous sodium hydrogen carbonate (80 ml) and ethyl acetate (150 ml), and the aqueous layer back extracted with ethyl acetate (2×80 ml). The combined organics were dried over anhydrous sodium sulphate, filtered and concentrated to give O-methyl-L-tyrosine methyl ester as a yellow oil.

delta$_H$ 7.07 (2H, d, J 8.5 Hz), 6.80 (2H, d, J 8.5 Hz), 3.75 (3H, s), 3.68 (3H, s), 3.67 (1H, m), 2.99 (1H, dd, J 13.6, 5.2 Hz), 2.79 (1H, dd, J 13.6, 7.7 Hz), 1.85 (2H, br s).

(d) N-4-(1H-2-Methylbenzimidazolylmethyl)phenylsulphonyl-O-methyl-L-tyrosine methyl ester N-4-(1H-2-Methylbenzimidazolylmethyl)phenylsulphonyl-O-methyl-L-tyrosine methyl ester was prepared from O-methyl-L-tyrosine methyl ester by a similar procedure to that used in Example 5.

White crystalline solid (4% yield for last step after chromatography (silica: 3% methanol in DCM)): m.p. 168°–170° C.

delta$_H$ 7.75–7.60 (3H, m), 7.27–7.04 (7H, m), 6.70 (2H, d, J 6.8 Hz), 5.70 (1H, br d), 5.32 (2H, s), 4.15 (1H, m), 3.71 (3H, s), 3.41 (3H, s), 2.93 (2H, dd, J 6.4, 3.5 Hz), 2.54 (3H, s).

EXAMPLE 12

N-4-(1H-2-Methylbenzimidazolylmethyl)phenylsulphonyl-O-benzyl-L-serine methyl ester

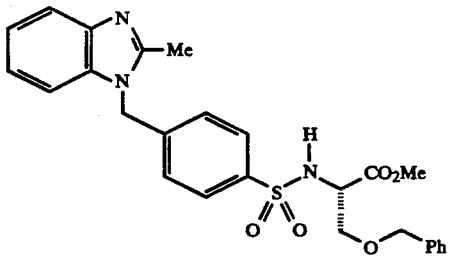

N-4-(1H-2-Methylbenzimidazolylmethyl)phenylsulphonyl-O-benzyl-L-serine methyl ester was prepared by the method of Example 5 starting from O-benzyl-L-serine methyl ester.

White crystalline solid (7% yield for last step after chromatography (silica: 1% methanol in DCM)): m.p. 125° C. Analysis calculated for $C_{26}H_{27}N_3SO_4.0.6H_2O$ Requires C 61.91 H 5.64 N 8.33. Found C 61.87 H 5.52 N 8.27.

i.r. (KBr) 1745, 1325, 1160 cm$^{-1}$.

delta$_H$ 7.80–7.70 (3H, m), 7.31–7.04 (10H, m), 5.70–5.60 (1H, m), 5.36 (2H, s), 4.42 (2H, dd, J 12.1 Hz), 4.18–4.06 (1H, m), 3.76 (1H, dd, J 9.5, 3.4 Hz), 3.60 (1H, dd, J 9.5, 3.5 Hz), 3.49 (3H, s), 2.55 (3H, s).

EXAMPLE 13

N-4-(1H-2-Methylbenzimidazolylmethyl)phenylsulphonyl-L-methionine methyl ester

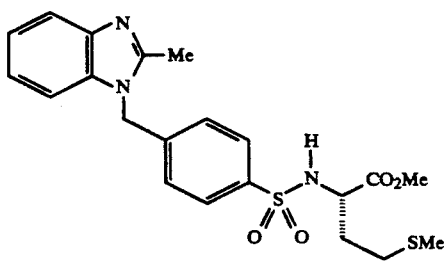

N-4-(1H-2-Methylbenzimidazolylmethyl)phenylsulphonyl-L-methionine methyl ester was prepared by the method of Example 1 starting from L-methionine methyl ester hydrochloride.

White crystalline solid (4% yield for last step after chromatography (silica: 5% methanol in chloroform)): m.p. 144° C. (dec.)

Analysis calculated for $C_{21}H_{25}N_3S_2O_4 \cdot 1.0\ H_2O$ Requires C 54.17 H 5.85 N 9.03. Found C 54.16 H 5.53 N 8.8.

i.r (KBr) 1740, 1325, 1115 cm$^{-1}$.

delta$_H$ 7.86–7.71 (3H, m), 7.30–7.12 (5H, m), 5.57 (1H, d, J 9.1 Hz), 5.38 (2H, s), 4.07 (1H, m), 3.45 (3H, s), 2.58 (3H, s), 2.61–2.41 (2H, m), 2.03 (3H, s), 2.03–1.80 (2H, m).

EXAMPLE 14

N-4-(1H-2-Methylbenzimidazolylmethyl)phenylsulphonyl-L-leucine ethyl ester

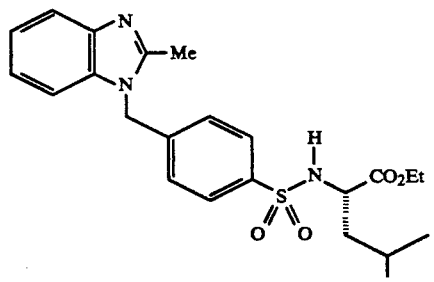

N-4-(1H-2-Methylbenzimidazolylmethyl)phenylsulphonyl-L-leucine ethyl ester was prepared by the procedures of Example 11 Step (c) and Step (d) starting from L-leucine and ethanol.

White crystalline solid (2% yield for last step after chromatography (silica: 3% methanol in DCM) and crystallisation from ethyl acetate/hexane) m.p. 205.5°–207° C.

Analysis calculated for $C_{23}H_{29}N_3SO_4$ Requires C 62.28 H 6.59 N 9.47. Found C 62.09 H 6.59 N 9.34.

delta$_H$ 7.79 (2H, d, J 8.5 Hz), 7.76 (1H, d, J 1.1 Hz), 7.20 (5H, m), 5.38 (2H, s), 5.11 (1H, d, J 10.0 Hz), 3.89 (1H, dt, J 10.0, 7.2 Hz), 3.75 (2H, dq, J 7.3, 3.5 Hz), 2.58 (3H, s), 1.75 (1H, m), 1.46 (2H, t, J 7.2 Hz), 0.97 (3H, t, J 7.2 Hz), 0.88 (3H, d, J 6.8 Hz), 0.86 (3H, d, J 6.8 Hz).

EXAMPLE 15

N-4-(1H-2-Methylbenzimidazolylmethyl)phenylsulphonyl-L-phenylalanine ethyl ester

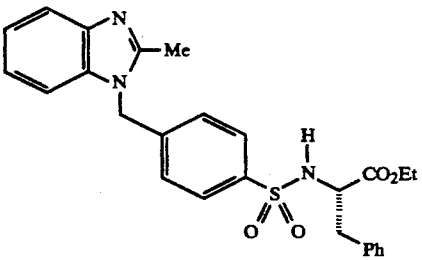

N-4-(1H-2-Methylbenzimidazolylmethyl)phenylsulphonyl-L-phenylalanine ethyl ester was prepared by the procedures of Example 11 Step (c) and Step (d) starting from L-phenylalanine and ethanol.

White crystalline solid (5% yield after chromatography (silica: 3% methanol in DCM) and crystallisation from ethyl acetate/hexane): m.p. 219°–220.5° C.

Analysis calculated for $C_{26}H_{27}N_3SO_4 \cdot 0.5H_2O$ Requires C 64.18 H 5.80 N 8.64. Found C 64.26 H 5.67 N 8.57.

delta$_H$ 7.75 (1H, dd, J 7.0, 1.3 Hz), 7.67 (2H, d, J 8.4 Hz), 7.16 (10H, m), 5.35 (2H, s), 5.25 (1H, d, J 9.3 Hz), 4.16 (1H, dt, J 9.2, 6.2 Hz), 3.81 (2H, dq, J 7.2, 4.3 Hz), 2.98 (2H, d, J 6.3 Hz), 2.56 (3H, s), 1.00 (3H, t, J 7.1 Hz).

EXAMPLE 16

N-4-(1H-2-Methylbenzimidazolylmethyl)phenylsulphonyl-L-methionine ethyl ester

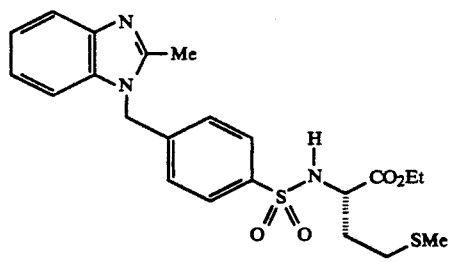

N-4-(1H-2-Methylbenzimidazolylmethyl)phenylsulphonyl-L-methionine ethyl ester was prepared by the method of Example 1 starting from L-methionine ethyl ester hydrochloride.

White crystalline solid (13% yield for last step after chromatography (silica 5% methanol in chloroform)): m.p. 78° C.

i.r. (KBr) 1740, 1320, 1155 cm$^{-1}$.

delta$_H$ 7.80–7.70 (3H, m), 7.27–7.10 (5H, m), 5.80 (1H, d, J 9.0 Hz), 5.35 (2H, s), 4.02 (1H, m), 3.93–3.78 (2H, m), 2.55 (3H, s), 2.60–2.42 (2H, m), 2.01 (3H, s), 2.03–1.78 (2H, m), 1.02 (3H, t, J 7.2 Hz).

EXAMPLE 17

N-4-(1H-2-Methylbenzimidazolylmethyl)phenylsulphonyl-L-aspartic acid diethyl ester

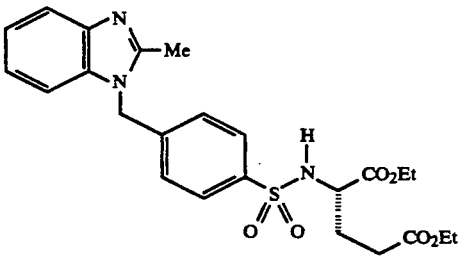

N-4-(1H-2-Methylbenzimidazolylmethyl)phenylsulphonyl-L-aspartic acid diethyl ester was prepared by the method of Example 1 starting from L-aspartic acid diethyl ester hydrochloride.

White crystalline solid (13% yield for last step after chromatography (silica 5% methanol in chloroform)): m.p. 140° C.

Analysis calculated for $C_{24}H_{29}N_3SO_6$ Requires C 59.12 H 6.00 N 8.62. Found C 58.94 H 5 98 N 8.50.

delta$_H$ 7.78–7.69 (3H, m), 7.30–7.11 (5H, m), 5.72 (1H, d, J 9.3 Hz), 5.35 (2H, s), 4.10 (2H, q, J 7.2 Hz), 4.00–3.73 (3H, m), 2.55 (3H, s), 2.48–2.38 (2H, m), 2.18–2.02 (1H, m), 1.93–1.78 (1H, m), 1.23 (3H, t, J 7.2 Hz), 0.99 (3H, t, J 7.2 Hz).

EXAMPLE 18

N-4-(1H-2-Methylbenzimidazolylmethyl)phenylsulphonyl-L-leucine isopropyl ester

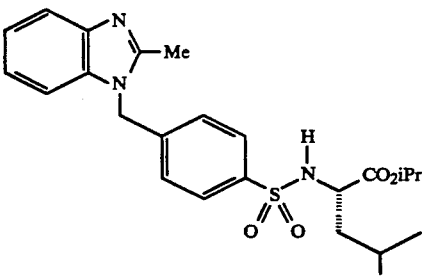

N-4-(1H-2-Methylbenzimidazolylmethyl)phenylsulphonyl-L-leucine isopropyl ester was prepared by the procedures of Example 11 Step (c) and Step (d) starting from L-leucine and isopropanol.

White crystalline solid (11% yield for last step after chromatography (silica: 3% methanol in DCM) and crystallisation from ethyl acetate/hexane): m.p. 191°–192° C.

Analysis calculate for $C_{24}H_{31}N_3SO_4$ Requires C 62.75 H 6.85 N 9.23. Found C 62.73 H 6.81 N 9.23.

delta$_H$ 7.82–7.70 (3H, m), 7.30–7.10 (5H, m), 5.37 (2H, s), 5.13 (1H, d, J 10.0 Hz), 4.62–4.51 (1H, m), 3.86 (1H, dt, J 10.0, 7.4 Hz), 2.57 (3H, s), 1.84–1.72 (1H, m), 1.44 (2H, t, J 7.4 Hz), 1.03 (3H, d, J 6.3 Hz), 0.93–0.81 (9H, m).

EXAMPLE 19

N-4-(1H-2-Methylbenzimidazolylmethyl)phenylsulphonyl-L-leucine n-butyl ester

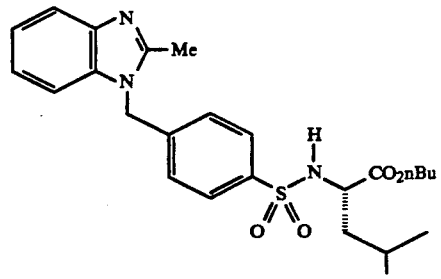

N-4-(1H-2-Methylbenzimidazolylmethyl)phenylsulphonyl-L-leucine n-butyl ester was prepared by the method of Example 11 Step (c) and Step (d) starting from L-leucine and n-butanol.

White solid (43% yield for last step after chromatography (silica: 3% methanol in DCM)): m.p. 111°–113° C.

i.r. (CHCl$_3$) 3020, 1735, 1345, 1185 cm$^{-1}$.

delta$_H$ 7.78–7.70 (3H, m), 7.25–7.11 (5H, m), 5.36 (2H, s), 5.01 (1H, d, J 9.9 Hz), 3.88 (1H, m), 3.77–3.58 (2H, m), 2.54 (3H, s), 1.73 (1H, m), 1.46–1.10 (6H, m), 0.88–0.79 (9H, m).

Delta$_C$ 172.13, 151.47, 145.39, 140.67, 139.77, 128.03, 126.77, 122.71, 122.52, 119.33, 109.02, 65.32, 54.46, 46.66, 42.36, 30.23, 24.29, 22.67, 21.40, 16.93, 13.63.

EXAMPLE 20

N-4-(1H-2-Methylbenzimidazolylmethyl)phenylsulphonyl-L-alanine tert-butyl ester

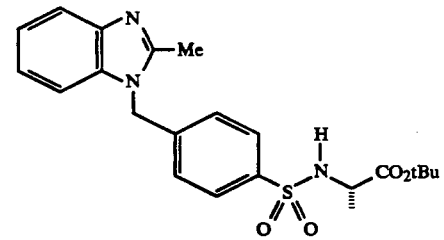

N-4-(1H-2-Methylbenzimidazolylmethyl)phenylsulphonyl-L-alanine tert-butyl ester was prepared by the method of Example 1 starting from L-alanine tert-butyl ester hydrochloride.

White crystalline solid (6% yield for last step after chromatography (silica: 5% methanol in DCM): m.p. 81° C.

i.r. (KBr) 1735, 1325, 1160 cm$^{-1}$.

delta$_H$ 7.83–7.72 (3H, m), 7.33–7.11 (5H, m), 5.40 (2H, s), 5.37 (1H, d, 14.3 Hz), 3.86 (1H, dt, J 14.3, 7.2 Hz), 2.56 (3H, s), 1.34 (3H, d, J 7.2 Hz) 1.25 (s, 9H).

delta$_C$ 169.73, 151.37, 141.51, 140.50, 140.17, 134.79, 128.02, 126.77, 122.98, 122.82, 119.10, 109.16, 51.99, 46.66, 27.66, 18.63, 12.24.

EXAMPLE 21

N-4-(1H-2-Methylbenzimidazolylmethyl)phenylsulphonyl-L-phenylalanine tert-butyl ester

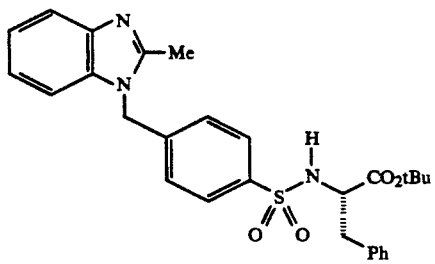

N-4-(1H-2-Methylbenzimidazolylmethyl)phenylsulphonyl-L-phenylalanine tert-butyl ester was prepared by the method of Example 5 starting from L-phenylalanine tert-butyl ester.

White crystalline solid (7% yield for last step after chromatography (silica: 3% methanol in DCM) and crystallisation from ethyl acetate/hexane) m.p. 165.5°–166.5° C.

Analysis calculated for $C_{28}H_{31}N_3SO_4$ Requires C 66.51 H 6.18 N 8.31. Found C 66.16 H 6.22 N 8.29.

i.r. ($CDCl_3$) 3040, 1740, 1345, 1160 $cm^{-1}$.

$delta_H$ 7.72 (3H, m), 7.19 (10H, m), 5.35 (2H, s), 5.18 (1H, d, J 9.3 Hz), 4.07 (1H, dt, J 9.3, 6.2 Hz), 2.99 (2H, d, J 6.1 Hz), 2.55 (3H, s), 1.17 (9H, s).

EXAMPLE 22

N-4-(1H-2-Methylbenzimidazolylmethyl)phenylsulphonyl-L-leucine benzyl ester

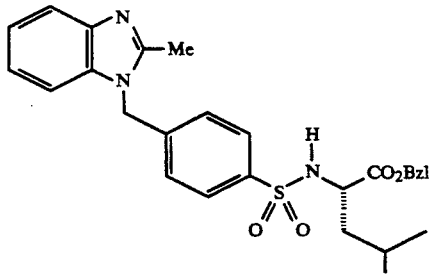

N-4-(1H-2-Methylbenzimidazolylmethyl)phenylsulphonyl-L-leucine benzyl ester was prepared by the method of Example 5 starting from L-leucine benzyl ester.

White crystalline solid (4% yield for last step after chromatography (silica: 3% methanol in DCM) and crystallisation from ethyl acetate/hexane): m.p. 130.5°–133° C.

Analysis calculated for $C_{28}H_{31}N_3SO_4.0.2H_2O$ Requires C 66.04 N 6.22 N 8.25. Found C 66 02 H 6.21 N 8.19.

$delta_H$ 7.75 (3H, m), 7.22 (10H, m), 5.37 (2H, s), 5.03 (1H, d, J 10.1 Hz), 4.81 (1H, d, J 12.3 Hz), 4.72 (1H, d, J 12.2 Hz), 3.98 (1H, dt, J 10.1, 7.4 Hz), 2.56 (3H, s), 1.74 (1H, m), 1.48 (2H, t, J 7.3 Hz), 0.87 (3H, d, J 6.6 Hz), 0.84 (3H, d, J 6.7 Hz).

EXAMPLE 23

N-4-(1H-2-Methylbenzimidazolylmethyl)phenylsulphonyl-L-phenylalanine benzyl ester

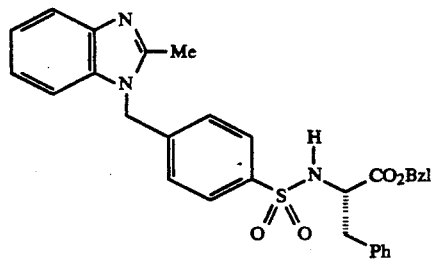

N-4-(1H-2-Methylbenzimidazolylmethyl)phenylsulphonyl-L-phenylalanine benzyl ester was prepared by the procedures of Example 11 Step (c) and Step (d) starting from L-phenylalanine and benzyl alcohol.

White crystalline solid (3% yield for last step after chromatography (silica: 3% methanol in DCM) and crystallisation from ethyl acetate/hexane): m.p. 114° C.

Analysis calculated for $C_{31}H_{29}N_3SO_4$ Requires C 68.29 H 5.54 N 7.96. Found C 68.77 H 5.43 N 7.74.

$delta_H$ 7.75 (1H, dd, J 6.8, 1.4 Hz), 7.66 (2H, m), 7.21 (15H, m), 5.35 (2H, s), 5.13 (1H, d, J 9.27 Hz), 4.83 (2H, dd, J 12.1, 7.4 Hz), 4.24 (1H, dt, J 9.3, 6.0 Hz), 3.02 (2H, ', J 6.0 Hz), 2.56 (3H, s).

EXAMPLE 24

N-4-(1H-2-Methylbenzimidazolylmethyl)phenylsulphonyl-L-isoleucine methylamide

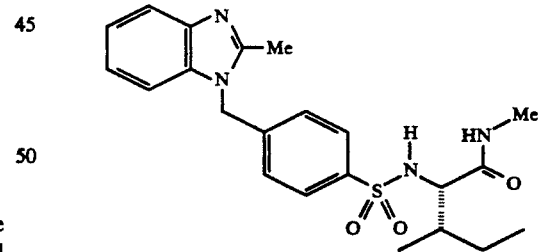

N-4-(1H-2-Methylbenzimidazolylmethyl)phenylsulphonyl-L-isoleucine methylamide was prepared by the method of Example 5 starting from L-isoleucine methylamide.

Colourless oil (0.3% yield for last step after chromatography (silica: 1% methanol in DCM)).

$delta_H$ 7.84–7.70 (3H, m), 7.38–7.12 (6H, m), 5.37 (2H, s), 5.36–5.24 (1H, m), 3.84–3.74 (1H, m), 3.33 (3H, s), 2.57 (3H, s), 1.84–1.70 (1H, m), 1.46–1.04 (2H, m), 0.98–0.80 (6H, m).

EXAMPLE 25

N-4-(1H-2-Methylbenzimidazolylmethyl)phenylsulphonyl-L-phenylalanine methylamide

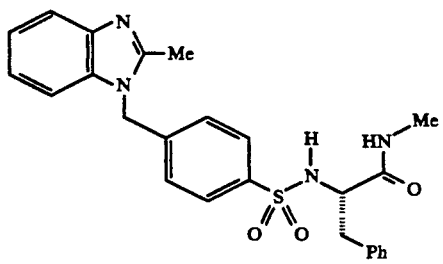

(a) N-Benzyloxycarbonyl-L-phenylalanine methylamide

To a stirred solution of N-benzyloxycarbonyl-L-phenylalanine p-nitrophenyl ester (5.0 g, 11.9 mmol) in DCM at 0° C. was slowly added a/solution of 8M methylamine (1.5 ml, 11.9 mmol) in ethanol. The reaction immediately turned bright yellow and was stirred for 0.5 h. The reaction was diluted with DCM (50 ml), washed with 10% sodium carbonate (1×50 ml), brine (2×50 ml) and dried over anhydrous magnesium sulphate. Filtration and evaporation gave a white residue which was crystallised from ethyl acetate/hexane to give N-benzyloxycarbonyl-L-phenylalanine methylamide (3.0 g, 81%) as a white crystalline solid.

m.p. 153°-154° C.

delta$_H$ 7.38-7.17 (10H, m), 5.62 (1H, br s), 5 32 (1H, br s), 5.09 (2H, s), 4.35 (1H, dd, J 14.4, 7.5 Hz), 3.12-2.99 (2H, m), 2.72 (3H, d, J 4.9 Hz).

(b) L-Phenylalanine methylamide

L-Phenylalanine methylamide was prepared following the method of Example Step (b) starting from N-benzyloxycarbonyl-L-phenylalanine methylamide.

Brown-red solid (1.6 g, 97%).

delta$_H$ 7.36-7.21 (6H, m), 3.61 (1H, dd, J 9.5, 4.0 Hz), 3.30 (1H, dd, J 13.7, 4.0 Hz), 2.82 (3H, d, J 5.0 Hz), 2.68 (1H, dd, J 13.7, 9.5 Hz), 1.48 (2H, br s).

(c) N-4-(1H-2-Methylbenzimidazolylmethyl)phenylsulphonyl-L-phenylalanine methylamide N-4-(1H-2-Methylbenzimidazolylmethyl)phenylsulphonyl-L-phenylalanine methylamide was prepared from L-phenylalanine methylamide by a similar procedure to that used in Example 5.

White Crystalline solid (3% yield for last step after chromatography (silica: 5% methanol in DCM) and crystallisation from ethyl acetate/hexane): m.p. 204° C.

i.r. (CHCl$_3$) 3450, 1760, 1345, 1165 cm$^{-1}$.

delta$_H$ 77 (1H, br d), 7.56 (2H, br d), 7.32-7.06 (8H, m), 6.89 (2H, m), 6.05 (1H, br d), 5.39 (2H, s), 5.01 (1H, br d), 3.78 (1H, dd, J 13.5, 6.7 Hz), 2.91 (2H, m), 2.68 (3H, d, J 4.9 Hz), 2.60 (3H, s).

EXAMPLE 26

N-4-(1H-2-Methylbenzimidazolylmethyl)phenylsulphonyl-L-phenylalanine 2-pyridylamide

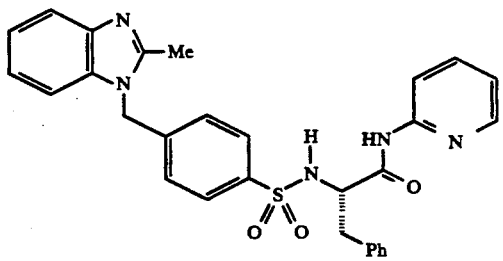

N-4-(1H-2-Methylbenzimidazolylmethyl)phenylsulphonyl-L-phenylalanine 2-pyridylamide was prepared following the method of Example 25 starting from N-benzyloxycarbonyl-L-phenylalanine p-nitrophenyl ester and 2-aminopyridine.

White crystalline solid (7% yield for last step after chromatography (silica 5% methanol in DCM)): m.p. 205°-207° C.

i.r. (KBr) 1675, 1330, 1160 cm$^{-1}$.

delta$_H$ 8.58 (1H, br s), 8.26 (1H, br d), 8.06 (1H, br d), 6.92-7.78 (15H, m), 5.55 (1H, br d), 5.30 (2H, s), 4.04 (1H, br d), 3.05 (2H, m), 2.51 (3H, s).

EXAMPLE 27

N-4-(1H-2-Methylbenzimidazolylmethyl)phenylsulphonyl-L-phenylalanine morpholinoamide

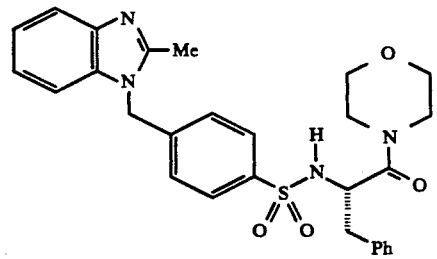

(a) N-tert-Butoxycarbonyl-L-phenylalanine morpholinoamide

N-tert-Butoxycarbonyl-L-phenylalanine morpholinoamide was prepared following the procedure of Example 25 Step (a) starting from N-tert-butoxycarbonyl-L-phenylalanine p-nitrophenyl ester and morpholine.

delta$_H$ 7.33-7.18 (5H, m), 5.48 (1H, d J 8.6 Hz), 4.83-4.74 (1H, m), 3.61-3.20 (6H, m), 3.05-2.80 (4H, m), 1.41 (9H, s).

(b) L-Phenylalanine morpholinoamide

Trifluoroacetic acid (2.5 ml) was added to a stirred solution of N-tert-butoxycarbonyl-L-phenylalanine p-nitrophenyl ester (1.0 g, 3.0 mmol) in DCM (20 ml) at 0° C. After 10 min the mixture was allowed to warm up to room temperature, stirred for 2.5 h and concentrated. The residue was dissolved in methanol (100 ml) and treated with basic AMBERLITE resin (IR-45), stirred for 10 min, filtered and concentrated. (The Word AMBERLITE is a trade mark.) Crystallisation from ethyl acetate gave L-phenylalanine morpholinoamide as a white crystalline solid.

delta$_H$ 7.40–7.12 (5H, m), 4.60 (2H, s), 4.30–2.87 (11H, m).

(c) N-4-(1H-2-Methylbenzimidazolylmethyl)phenylsulphonyl-L-phenylalanine morpholinoamide N-4-(1H-2-Methylbenzimidazolylmethyl)phenylsulphonyl-L-phenylalanine morpholinoamide was prepared by the method of Example 5 starting from L-phenylalanine morpholinoamide.

White crystalline solid (9% yield for last step after chromatography (silica: 1% methanol in DCM)): m.p. 90° C.

i.r. (KBr) 1635, 1325, 1115 cm$^{-1}$.

delta$_H$ 7.80–7.64 (3H, m), 7.30–7.03 (10H, m), 6.28 (1H, d, J 9.6 Hz), 5.34 (2H, s), 4.40–4.30 (1H, m), 3.40–2.51 (10H, m), 2.57 (3H, s).

delta$_C$ 168.78, 151.44, 142.17, 140.81, 140.08, 135.23, 134.79, 129.42, 128.65, 127.74, 127.37, 126.62, 122.70, 122.52, 119.25, 109.02, 53.09, 46.51, 45.57, 41.97, 40.73.

EXAMPLE 28

N-4-(1H-2-Methylbenzimidazolylmethyl)phenylsulphonyl-L-leucine pyrrolidinoamide

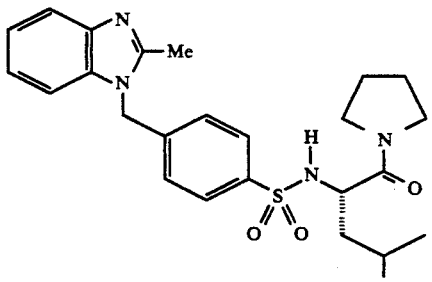

N-4-(1H-2-Methylbenzimidazolylmethyl)phenylsulphonyl-L-leucine pyrrolidinoamide was prepared by the method of Example 5 Step (a) and Example 1 Step (c) starting from L-leucine pyrrolidinoamide.

White crystalline solid (6% yield for last step after chromatography (silica: 5% methanol in DCM)): m.p. 126° C.

i.r. (CDCl$_3$) 1635, 1340, 1160 cm$^{-1}$.

delta$_H$ 7.80–7.70 (3H, m), 7.30–7.10 (5H, m), 5.56 (1H, d, J 9.9 Hz), 5.39–5.30 (2H, m), 4.00–3.83 (1H, m), 3.20–3.02 (3H, m), 2.78–2.60 (1H, m), 2.58 (3H, s), 2.00–1.10 (7H, m), 0.95–0.83 (6H, m).

delta$_C$ 169.29, 151.43, 142.71, 140.86, 139.82, 135.01, 128.00, 126.55, 122.58, 122.41, 119.48, 108.88, 53.12, 46.58, 45.88, 45.73, 42.03, 25.79, 24.07, 23.79, 23.28, 21.09.

EXAMPLE 29

N-4-(1H-2-Methylbenzimidazolylmethyl)phenylsulphonyl-L-prolinyl methyl ester

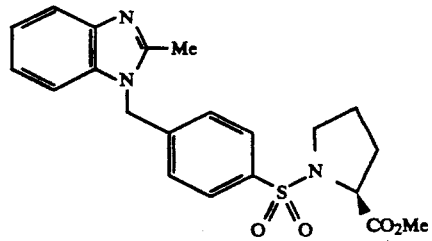

N-4-(1H-2-Methylbenzimidazolylmethyl)phenylsulphonyl-L-prolinyl methyl ester was prepared following the procedure of Example 1 starting from L-prolinyl methyl ester hydrochloride.

Colourless viscous oil (30% yield for last step after chromatography (silica: 5% methanol in chloroform)).

delta$_H$ 7.83–7.70 (3H, m), 7.31–7.12 (5H, m), 5.37 (2H, s), 4.31 (1H, dd, J 7 7, 4.0 Hz), 3.65 (3H, s), 3.48–3.24 (2H, m), 2.55 (3H, s), 2.12–1.72 (4H, m).

delta$_C$ 172.32, 151.56, 142.55, 140.92, 138.30, 129.40, 128.12, 126.74, 122.51, 122.29, 119.26, 109.02, 60.25, 52.27, 48.20, 46.54, 30.80, 24.56.

EXAMPLE 30

N-4-(1H-2-Methylbenzimidazolylmethyl)phenylsulphonyl-L-prolinyl benzyl ester

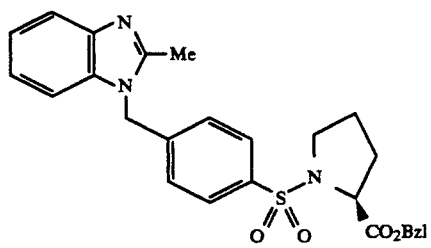

N-4-(1H-2-Methylbenzimidazolylmethyl)phenylsulphonyl-L-prolinyl benzyl ester was prepared following the procedure of Example 1 starting from L-prolinyl benzyl ester hydrochloride.

Colourless viscous oil (13% yield for last step after chromatography (silica: 5% methanol in chloroform)).

delta$_H$ 7.82–7.73 (3H, m), 7.36–7.08 (10H, m), 5.35 (2H, s), 5.10 (2H, s), 4.40 (1H, dd, J 8.0, 3.8 Hz), 3.47–3.26 (2H, m), 2.55 (3H, s), 2.17–1.76 (4H, m).

delta$_C$ 171.67, 151.54, 142.64, 140.89, 138.41, 135.29, 135.13, 128.50, 128.31, 128.17, 128.03, 126.68, 122.49, 122.28, 119.32, 109.02, 66.98, 60.35, 48.17, 46.54, 30.83, 24.60.

EXAMPLE 31

(A)

N-4-(3H-Imidazo[4,5-c]pyridylmethyl)phenylsulphonyl-L-leucine methyl ester and (B)

N-4-(1H-imidazo[4,5-c]pyridylmethyl)phenylsulphonyl-L-leucine methyl ester

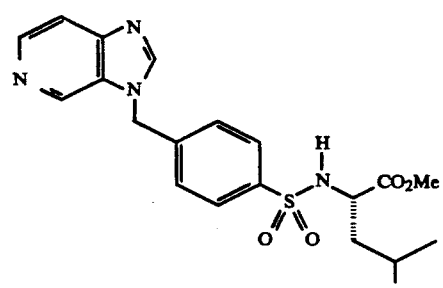

A

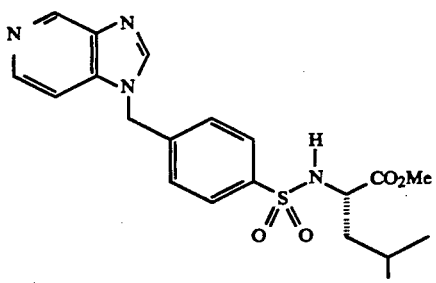

N-4-(3H-Imidazo[4,5-c]pyridylmethyl)phenylsulphonyl-L-leucine methyl ester and N-4-(1H-imidazo[4,5-c]pyridylmethyl)phenylsulphonyl-L-leucine methyl ester were prepared by the method of Example 7 employing in the final step imidazo[4,5-c]pyridine in lieu of 2-methylbenzimidazole and using 1:1 DMF:THF as solvent. Chromatography (silica: 8% methanol in DCM) gave N-4-(3H-imidazo[4,5-c]pyridylmethyl)phenylsulphonyl-L-leucine methyl ester (regioisomer A) which eluted first followed by N-4-(1H-imidazo[4,5-c]pyridylmethyl)phenylsulphonyl-L-leucine methyl ester (regioisomer B).

Regioisomer (A): Orange amorphous solid (3% yield for last step after chromatography).

i.r. (CHCl$_3$) 3020, 1740, 1420, 1190 cm$^{-1}$.

delta$_H$ 8.71 (1H, br s), 8.48 (1H, br d), 8.13 (1H, s), 7.74–7.82 (3H, m), 7.31 (2H, d, J 8.4 Hz), 6.00 (1H, br s), 5.52 (2H, s), 3.93 (1H, br m), 3.34 (3H, s), 1.74 (1H, m), 1.49 (2H, dd, J 7.3, 6.2 Hz), 0.87 (3H, d, J 6.9 Hz), 0.84 (3H, d, J 7.2 Hz).

Regioisomer (B): White amorphous solid (10% yield).

i.r. (CHCl$_3$) 3015, 1740, 1420, 1185 cm$^{-1}$.

delta$_H$ 9.14 (1H, br s), 8.40 (1H, br d), 8.06 (1H, s), 7.78 (2H, d, J 8.4 Hz), 7.25 (2H, d, J 8.4 Hz), 7.17 (1H, d, J 5.5 Hz), 6.08 (1H, br s), 5.45 (2H, s), 3.93 (1H, br d), 3.33 (3H, s), 1.73 (1H, m), 1.48 (2H, dd, J 7.3, 7.0 Hz), 0.86 (3H, d, J 6.7 Hz), 0.82 (3H, d, J 6.5 Hz).

EXAMPLE 32

(A) N-4-(3H-2-Methylimidazo[4,5-c]pyridylmethyl)phenylsulphonyl-L-leucine methyl ester and (B) N-4-(1H-2-methylimidazo[4,5-c]pyridylmethyl)phenylsulphonyl-L-leucine methyl ester

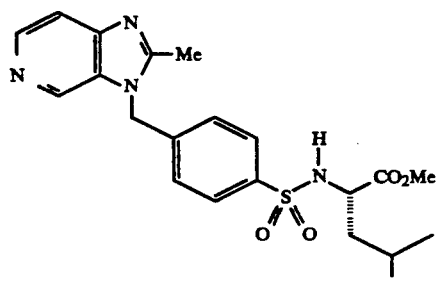

N-4-(3H-2-Methylimidazo[4,5-c]pyridylmethyl)phenylsulphonyl-L-leucine methyl ester and N-4-(1H-2-methylimidazo[4,5-c]pyridylmethyl)phenylsulphonyl-L-leucine methyl ester were prepared by the method of Example 7 employing in the final step 2-methylimidazo[4,5-c]pyridine in lieu of 2-methylbenzimidazole and using 1:1 DMF:THF as solvent. Chromatography (silica: 2% methanol in DCM) gave N-4-(3H-2-methylimidazo[4,5-c]pyridylmethyl)phenylsulphonyl-L-leucine methyl ester regioisomer A) which eluted first followed by N-4-(1H-2-methylimidazo[4,5-c]pyridylmethyl)phenylsulphonyl-L-leucine methyl ester (regioisomer B) which was crystallised from chloroform/hexane.

Regioisomer (A): White crystalline solid; m.p. 198° C. (dec.).

Analysis calculated for C$_{21}$H$_{26}$N$_4$O$_4$S Requires C 58.58 H 6.09 N 13.02. Found C 58.56 H 6.09 N 12.95.

i.r. (CDCl$_3$) 2960, 2240, 1735, 1345, 1160 cm$^{-1}$.

delta$_H$ 8.85 (1H, br s), 8.46 (1H, d, J 7.9 Hz), 7.83 (2H, d, J 8.3 Hz), 7.76 (1H, d, J 5.6 Hz), 7.21 (2H, d, J 8.3 Hz), 5.56 (2H, s), 5.31 (1H, d, J 10.1 Hz), 3.93 (1H, m), 3.42 (3H, s), 2.67 (3H, s), 1.74 (1H, m), 1.50 (2H, dd, J 7.3, 7.0 Hz), 0.89 (3H, d, J 6.7 Hz), 0.86 (3H, d, J 6.5 Hz).

Regioisomer (B): White crystalline solid (93 mg, 3% yield): m.p. 190° C. (dec.).

Analysis calculated for C$_{21}$H$_{26}$N$_4$O$_4$S.0.75CHCl$_3$ Requires C 50.23 H 5.18 N 10.77. Found C 50 38 H 5.29 N 10.61.

i.r. (CDCl$_3$) 1725, 1375, 1160 cm$^{-1}$.

delta$_H$ 9.06 (1H, s), 8.39 (1H, d, J 5.6 Hz), 7.80 (2H, d, J 8.4 Hz), 7.20–7.10 (3H, m), 5.40 (2H, s), 5.04 (1H, d, J 9.6 Hz), 4.00–3.90 (1H, m), 3.3S (3H, s), 2.61 (3H, s), 1.80–1.67 (1H, m), 1.48 (2H, t, J 7.2 Hz), 0.8S (3H, d, J 6.6 Hz), 0.86 (3H, d, 6.4 Hz).

EXAMPLE 33

(A) N-4-(3H-Imidazo[4,5-c]pyridylmethyl)phenylsulphonyl-L-phenylalanine methyl ester and (B) N-4-(1H-imidazo[4,5-c]pyridylmethyl)phenylsulphonyl-L-phenylalanine methyl ester

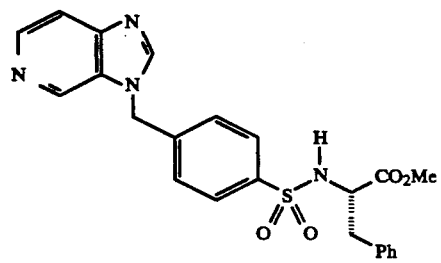

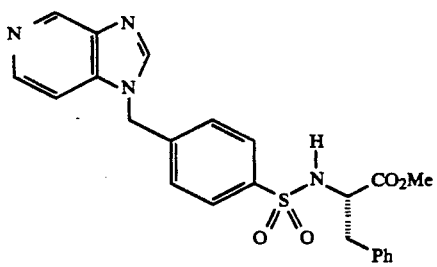

(A) N-4-(3H-Imidazo[4,5-pyridylmethyl)phenylsulphonyl-L-phenylalanine methyl ester and (B) N-4-(1H-imidazo[4,5-c]pyridylmethyl)phenylsulphonyl-L-phenylalanine methyl ester were prepared by the method of Example 10. In the final step imidazo[4,5-c]pyridine was employed in lieu of 2-methylbenzimidazole.

Regioisomer (A): Pale yellow crystalline solid (0.5% yield for last step after chromatography (silica: 5% methanol in DCM)): m.p. 136° C. (dec.)

i.r. (CDCl$_3$) 1740, 1340, 1155 cm$^{-1}$.

delta$_H$ 8.71 (1H, s), 8.47 (1H, br d, J 5.6 Hz), 8.11 (1H, s), 7.76 (1H, d, J 5.5 Hz), 7.75-7.64 (2H, m), 7.30-7.00 (7H, m), 5.82-5.62 (1H, m), 5.49 (2H, s), 4.24-4.14 (1H, m), 3.46 (3H, s), 3.13-2.91 (2H, m).

Regioisomer (B): White crystalline solid (0.6% yield).

delta$_H$ 9.17 (1H, s), 8.43 (1H, d, J 5.5 Hz), 8.05 (1H, s), 7.75-7.64 (2H, m), 7.25-7.00 (8H, m), 5.44 (2H, s), 4.26-4.18 (1H, m), 3.46 (3H, s), 3.12-2.94 (2H, m).

EXAMPLE 34

(A) N-4-(3H-Imidazo[4,5-c]pyridylmethyl)phenylsulphonyl-O-benzyl-L-serine methyl ester and (B) N-4-(1H-imidazo[4,5-c]pyridylmethyl)phenylsulphonyl-O-benzyl-L-serine methyl ester

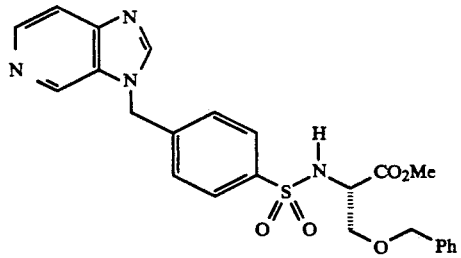

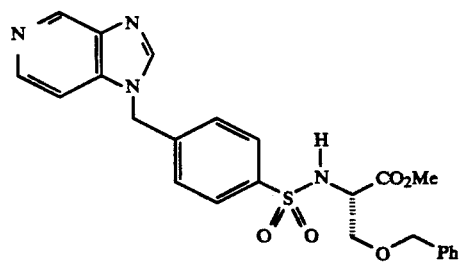

(A) N-4-(3H-Imidazo[4,5-c]pyridylmethyl)phenylsulphonyl-L-phenylalanine methyl ester and (B) N-4-(1H-imidazo[4,5-c]pyridylmethyl)phenylsulphonyl-L-phenylalanine methyl ester were prepared by the method of Example 12. In the final step imidazo[4,5-c]pyridine was employed in lieu of 2-methylbenzimidazole.

Regioisomer (A): White crystalline solid (5% yield for last step after chromatography (silica: 2% methanol in DCM)): m.p. 160° C.

i.r. (CDCl$_3$) 1750, 1340, 1160 cm$^{-1}$.

delta$_H$ 8.69 (1H, s), 8.48 (1H, d, J 5.6 Hz), 8.08 (1H, s), 7.84-7.75 (3H, m), 7.38-7.14 (7H, m), 6.10 (1H, br s), 5.48 (2H, s), 4.46 (1H, d, J 12.0 Hz), 4.39 (1H, d, J 12.0 Hz), 4.20-4.10 (1H, m), 4.19-4.10 (1H, br s), 3.79 (1H, dd, J 9.3, 3.4 Hz), 3.63 (1H, dd, J 9.3, 3.5 Hz), 3.51 (3H, s).

Regioisomer (B): White crystalline solid (3% yield): m.p. 156° C.

i.r. (KBr) 1740, 1335, 1160 cm$^{-1}$.

delta$_H$ 9.16 (1H, s), 8.40 (1H, d, J 5.6 Hz), 8.03 (1H, s), 7.79 (2H, d, J 8.4 Hz), 7.33-7.12 (8H, m), 6.22 (1H, br s), 5.41 (2H, s), 4.41 (2H, dd, J 12, 12 Hz), 3.79 (1H, dd, J 9.4, 3.4 Hz), 3.62 (1H, dd, J 9.4, 3.5 Hz), 3.48 (3H, s).

EXAMPLE 35

(A) N-4-(3H-2-Methylimidazo[4,5-c]pyridylmethyl)phenylsulphonyl-L-leucine ethyl ester and (B) N-4-(1H-2-methylimidazo[4,5-c]pyridylmethyl)phenylsulphonyl-L-leucine ethyl ester

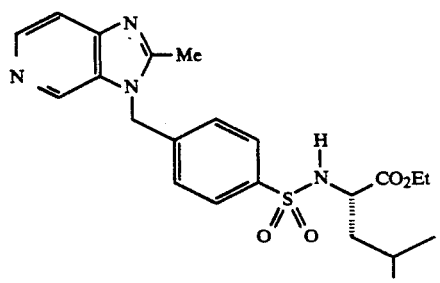

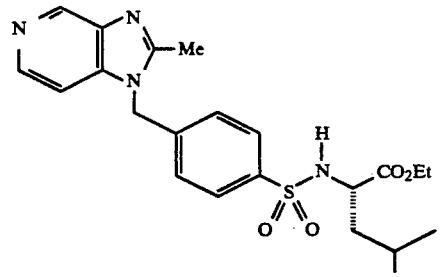

(a) N-4-Bromomethylphenylsulphonyl-L-leucine ethyl ester

L-leucine ethyl ester hydrochloride (1) (75.0 g. 0.403 mol) was suspended in THF (300 ml) at 0° C., and triethylamine (67 ml, 0.484 mol) added slowly. After stirring for 15 min. a solution of 4-bromomethylsulphonyl chloride (108.4 g, 0.403 mol) in dry THF (100 ml) was added via cannular. The reaction mixture was allowed to stir overnight at ambient temperature. The solvent was removed under low pressure and the organics were extracted into ethyl acetate (200 ml) and washed with water (100 ml) and brine (100 ml). The organic portion was dried over anhydrous magnesium sulphate, filtered and the solvent evaporated under low pressure. The product was recrystallised from DIPE (500 ml) to give N-4-bromomethylphenylsulphonyl-L-leucine ethyl ester (134 g, 85%) as a white crystalline solid.

[a]D20 +21.8 (c 2.2, DCM).

i.r. (DCM) 3325, 1735, 1340, 1160 cm$^{-1}$.

delta$_H$ 7.84 (2H, d, J 8.3 Hz), 7.52 (2H, d, J 8.3 Hz), 5.06 (1H, d, J 10.1 Hz), 4.61 (2H, s), 3.97-3.82 (3H, m), 1.85-1.79 (1H, m), 1.49 (2H, t, J 7.1 Hz), 1.08 (3H, t, J 7.1 Hz), 0.92 (3H, d, J 6.7 Hz), 0.91 (3H, d, J 6.5 Hz).

(b) (A) N-4-(3H-2-Methylimidazo[4,5-c]pyridylmethyl)phenylsulphonyl-L-leucine ethyl ester and (B) N-4-(1H-2-methylimidazo[4,5-c]pyridylmethyl)phenylsulphonyl-L-leucine ethyl ester A stirred mixture of 2-methylimidazo[4,5-c]pyridine (3.52 g, 26 mmol), potassium hydroxide (1.48 g, 26 mmol) and tris(2-(2-methoxyethoxy)ethyl)amine (3 drops) in dry acetonitrile (200 ml) was heated at 100° C. for 3 h under argon. The temperature was reduced to 40° C. and a solution of N-4-bromomethylphenylsulphonyl-L-leucine ethyl ester (10.0 g, 26 mmol) in dry acetonitrile (50 ml) was added. The mixture was stirred at 40° C. overnight The solvent was removed and the residue filtered through a short pad of silica (eluent: 10% methanol in DCM) to remove unreacted starting materials Chromatography (silica 6% methanol in DCM) gave N-4-(3H-2-methylimidazo[4,5-c]pyridylmethyl)phenylsulphonyl-L-leucine ethyl ester (regioisomer A) which eluted first followed by N-4-(1H-2-methylimidazo[4,5-c]pyridylmethyl)phenylsulphonyl-L-leucine ethyl ester (regioisomer B).

Regioisomer (A): White crystalline solid from ethyl acetate (0.58 g, 5% yield): m.p. 193° C. (dec.).

Analysis calculated for $C_{22}H_{28}N_4O_4S$ Requires C 59.44 H 6.35 N 12.60. Found C 59.22 H 6.27 N 12.56.

i.r. (CHCl$_3$) 3015, 1735, 1420, 1185 cm$^{-1}$.

delta$_H$ 8.71 (1H, s), 8.30 (1H, d, J 5.6 Hz), 7.76 (2H, d, J 8.4 Hz), 7.60 (1H, d, J 5.5 Hz), 7.30 (2H, d, J 8.4 Hz), 5.66 (2H, s), 3.82-3.74 (1H, m), 3.59 (2H, q, J 7.2 Hz), 2.65 (3H, s), 1.90-1.74 (1H, m), 1.43-1.31 (2H, m), 0.88 (3H, t, J 7.0 Hz), 0.82 (3H, d, J 6.7 Hz), 0.75 (3H, d, J 6.5 Hz).

Regioisomer (B): White crystalline solid from ethyl acetate (0.59 g, 5% yield): m.p. 173° C. (dec.).

Analysis calculated for $C_{22}H_{28}N_4O_4S$ Requires C 59.44 H 6.35 N 12.60. Found C 59.41 H 6.36 N 12.57.

i.r. (CHCl$_3$) 3005, 1735, 1415, 1170 cm$^{-1}$.

delta$_H$ 8.99 (1H, s), 8.33 (1H, d, J 5.0 Hz), 7.73 (2H, d, J 8.4 Hz), 7.12-7.07 (3H,.m), 6.50 (1H, d, J 9.4 Hz), 5.35 (2H, s), 3.94-3.68 (3H, m), 2.56 (3H, s), 1.72 (1H, m), 1.45 (2H, dd, J 7.4, 5.7 Hz), 0.95 (3H, t, J 7.1 Hz), 0.83 (3H, d, J 6.8 Hz), 0.80 (3H, d, J 6.7 Hz).

EXAMPLES 36–47

The compounds of Examples 36–47 were prepared by the method of Example 1 Step (c) starting from the appropriate N-4-bromomethylphenylsulphonylamino acid ester and utilising 2-methylimidazo[4,5-c]pyridine in lieu of 2-methylbenzimidazole and 1:3 DMF/THF as solvent. The N-4-bromomethylphenylsulphonylamino acid esters were prepared by the method of Example 1 Step (b) from the appropriate amino acid ester hydrochloride or p-toluenesulphonate salts. If not available commercially the amino acid ester salts were prepared from the appropriate amino acid and alcohol according to the method of Example 2 Step (a).

36 (A) N-4-(3H-2-Methylimidazo[4,5-c]pyridylmethyl)phenylsulphonyl-L-leucine n-propyl ester and (B) N-4-(1H-2-methylimidazo[4,5-c]pyridylmethyl)phenylsulphonyl-L-leucine n-propyl ester

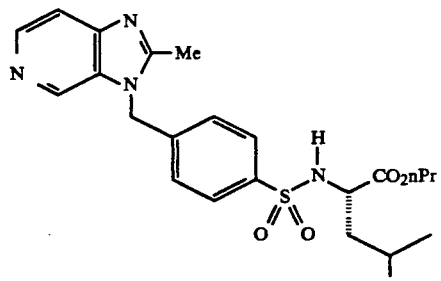

A

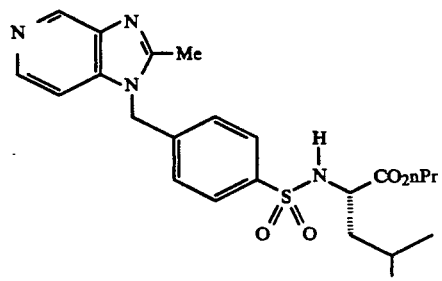

B

Regioisomers (A) and (B) were separated by chromatography (silica: 7% methanol in DCM).

Regioisomer (B): White crystalline (4% yield for last step after chromatography and crystallisation from ethyl acetate): m.p. 159° C.

Analysis calculated for $C_{23}H_3N_4O_4S$ Requires C 60.24 H 6.60 N 12.22. Found C 60.09 H 6.62 N 12.17.

i.r. (KBr) 1735, 1150 cm$^{-1}$.

delta$_H$ 9.04 (1H, s), 8.38 (1H, d, J 5.5 Hz), 7.79 (2H, d, J 8.3 Hz), 7.13 (3H, m), 5.50 (1H, d, J 9.9 Hz), 5.38 (2H, s), 3.93 (1H, m), 3.75-3.61 (2H, m), 2.59 (3H, s), 1.76 (1H, m), 1.53-1.36 (4H, m), 0.95-0.73 (9H, m).

37. (A) N-4-(3H-2-Methylimidazo[4,5-c]pyridylmethyl)phenylsulphonyl-L-leucine allyl ester and (B) N-4-(1H-2-methylimidazo[4,5-c]pyridylmethyl)phenylsulphonyl-L-leucine allyl ester

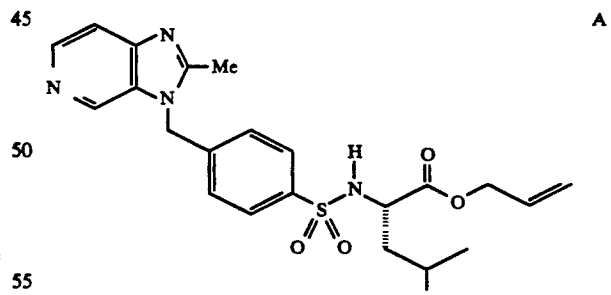

A

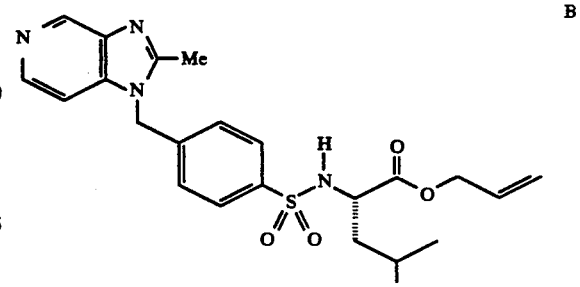

B

Regioisomer (A): White crystalline solid (5% yield for last step after chromatography (silica: 8% methanol in DCM) and crystallisation from ethyl acetate): m.p. 173° C.

Analysis calculated for $C_{23}H_{28}N_4O_4S.0.2H_2O$ Requires C 59.57 H 6.26 N 12.08. Found C 59.87 H 6.16 N 11.95.

i.r. (KBr) 1740 cm$^{-1}$.

delta$_H$ 8.62 (1H, s), 8.46 (1H, d, J 5.3 Hz), 7.82 (2H, d, J 8.4 Hz), 7.66 (1H, d, J 5.6 Hz), 7.14 (2H, d, J 8.3 Hz), 5.73–5.58 (1H, m), 5.46 (2H, s), 5.35–5.25 (1H, m), 5.21–5.08 (2H, m), 4.26 (2H, t, J 6.8 Hz), 3.96 (1H, m), 2.62 (3H, s), 1.85–1.65 (1H, m), 1.50 (2H, t, J 7.2 Hz), 0.83 (3H, d, J 6.6 Hz), 0.74 (3H, d, J 6.8 Hz).

Regioisomer (B): White crystalline solid from ethyl acetate (5% yield): m.p. 158° C.

Analysis calculated for $C_{23}H_{28}N_4O_4S.0.2H_2O$ Requires C 60.03 H 6.22 N 12.18. Found C 60.04 H 6.19 N 12.08.

i.r (KBr) 1735, 1150 cm$^{-1}$.

delta$_H$ 9.02 (1H, s), 8.36 (1H, d, J 4.8 Hz), 7.76 (2H, d, J 8.3 Hz), 7.11 (3H, m), 6.21 (1H, s), 5.70–5.55 (1H,.m), 5.37 (2H, s), 5.16–5.09 (2H, m), 4.23 (2H, t, J 5.6 Hz), 3.95 (1H, m), 2.58 (3H, s), 1.74 (1H, m), 1.48 (2H, t, J 7.0 Hz), 0.85 (3H, d, J 6.6 Hz), 0.81 (3H, d, J 6.5 Hz).

38. (A) N-4-(3H-2-Methylimidazo[4,5-c]pyridylmethyl)phenylsulphonyl-L-leucine i-propyl ester and (B) N-4-(1H-2-methylimidazo[4,5-c]pyridylmethyl)phenylsulphonyl-L-leucine i-propyl ester

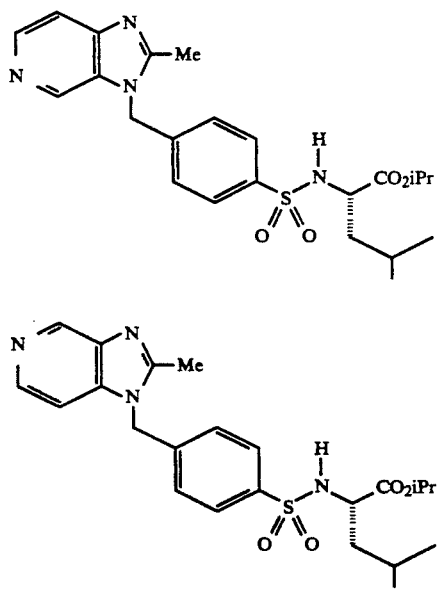

Regioisomer (A): White crystalline solid (4% yield for last step after chromatography (silica: 4% methanol in DCM)): m.p.194°–195° C. i.r. (CDCl$_3$) 2970, 1730, 1340, 1165 cm$^{-1}$.

delta$_H$ 8.66 (1H, s), 8.45 (1H, s), 7.82 (2H, d, J 8.4 Hz), 7.67 (1H, d, J 5.6 Hz), 7.18 (2H, d, J 8.4 Hz), 5.46 (2H, s), 5.35 (1H, d, J 9.9 Hz), 4.63 (1H, m), 3.88 (1H, m), 2.61 (3H, s), 1.78 (1H, m), 1.45 (2H, t, J 7.1 Hz), 1.05 (3H, d, J 6.3 Hz), 0.90 (3H, d, J 6.3 Hz), 0.89 (3H, d, J 6.3 Hz), 0.87 (3H, d, J 6.3 Hz).

delta$_C$ 171.58, 154.99, 147.88, 142.37, 140.46, 139.87, 132.13, 128.16, 126.78, 114.16, 69.26, 54.51, 46.99, 42.29, 24.26, 22.69, 21.32, 13.91.

Regioisomer (B): White crystalline solid (4% yield): m.p. 172° C.

Analysis calculated for $C_{23}H_{30}N_4SO_4.0.2H_2O$ Requires C 59.77 H 6.63 N 12.12. Found C 59.85 H 6.72 N 11.76.

i.r. (CHCl$_3$) 3020, 1740, 1350, 1230 cm$^{-1}$.

delta$_H$ 9.03 (1H, s), 8.38 (1H, d, J 5.5 Hz), 7.79 (2H, d, J 8.3 Hz), 7.15–7.11 (3H, m), 6.31 (1H, d, J 6.9 Hz), 5.37 (2H, s), 4.59 (1H, m), 3.86 (1H, m), 2.58 (3H, s), 1.77 (1H, m), 1.44 (2H, t, J 7.1 Hz), 1.03 (3H, d, J 6.3 Hz), 0.89–0.84 (9H, m).

39. (A) N-4-(3H-2-Methylimidazo[4,5-c]pyridylmethyl)phenylsulphonyl-L-leucine n-butyl ester and (B) N-4-(1H-2-methylimidazo[4,5-c]pyridylmethyl)phenylsulphonyl-L-leucine n-butyl ester

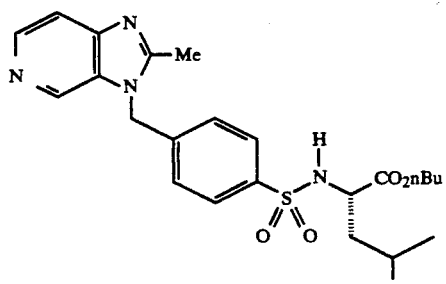

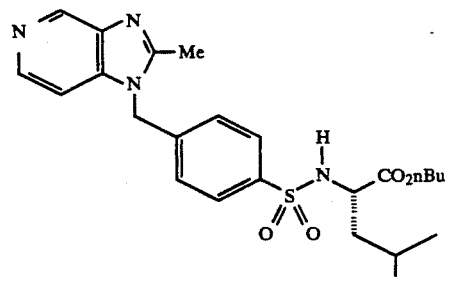

Regioisomer (A): White crystalline solid (2% yield for last step after chromatography (silica: 4% methanol in DCM) and crystallisation from ethyl acetate):

delta$_H$ 8.68 (1H, s), 8.43 (1H, s), 7.78 (2H, d, J 8.2 Hz), 7.65 (1H, m), 7.15 (2H, d, J 8.2 Hz), 5.89 (1H, d, J, 9.3 Hz), 5.47 (2H, s), 3.95–3.64 (3H, m), 2.61 (3H, s), 1.75–1.65 (1H, m), 1.53–1.34.(4H, m), 1.28–1.14 (2H, m), 0.98–0.78 (9H, m).

Regioisomer (B): White crystalline solid from ethyl acetate (2% yield):

delta$_H$ 9.05 (1H, s), 8.39 (1H, s), 7.79 (2H, d, J 8.2 Hz), 7.18–7.11 (3H, m), 5.75 (1H, s), 5.38 (2H, s), 3.91 (1H, m), 3.64–3.62 (2H, m), 2.58 (3H, s), 1.74 (1H, m), 1.50–1.34 (4H, m), 1.27–1.14 (2H, m), 0.88–0.65 (9H, m).

40. (A).N-4-(3H-2-Methylimidazo[4,5-c]pyridylmethyl)phenylsulphonyl-L-leucine 1-methylpropyl ester and (B) N-4-(1H-2methylimidazo[4,5-c]pyridylmethyl)phenylsulphonyl-L-leucine 1methylpropyl ester

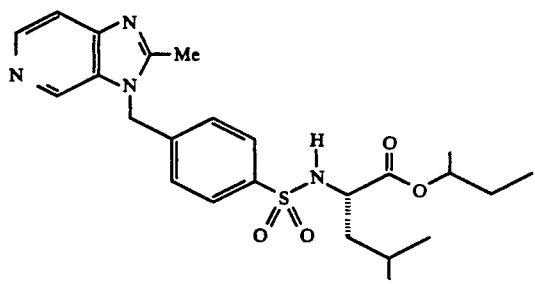

A

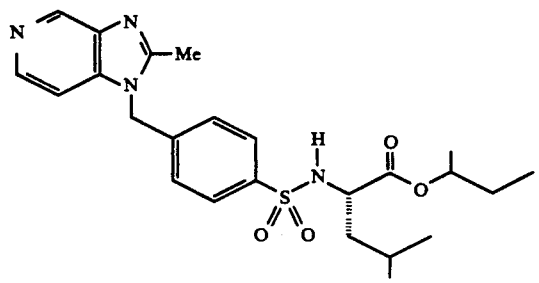

B

Regioisomer (A): White crystalline solid (1.5% yield for last step crystallisation from ethyl acetate): m.p. 130° C.

Analysis calculated for C₂₄H₃₂N₄O₄S Requires C 60.99 H 6.83 N 11.86. Found C 60.75 H 6.80 N 11.95.

i.r (KBr) 1735 cm⁻¹.

delta$_H$ 8.62 (1H, s), 8.47 (1H, d, J 5.6 Hz), 7.83 (2H, d, J 7.2 Hz), 7.66 (1H, d, J 5.7 Hz), 7.19 (2H, d, J 6.9 Hz), 5.45 (2H, s), 5.16 (1H, m), 4.52 (1H, m), 3.89 (1H, m), 2.61 (3H, s), 1.84–1.63 (1H, m), 1.50–1.26 (4H, m), 1.04–0.61 (12H, m).

Regioisomer (B): White crystalline solid from ethyl acetate (1% Yield): m.p. 165° C.

Analysis calculated for C₂₄H₃₂N₄O₄S.0.2H₂O Requires C 60.53 H 6.86 N 11.77. Found C 60.66 H 6.78 N 11.73.

i.r. (KBr) 1730, 1320, 1145 cm⁻¹.

delta$_H$ 9.00 (1H, s), 8.33 (1H, d, J 5.5 Hz), 7.73 (2H, d, J 8.3 Hz), 7.09 (3H, m), 6.47 (1H, d, J 8.2 Hz), 5.34 (2H, s), 4.45 (1H, m), 3.85 (1H, m), 2.54 (3H, s), 1.74 (1H, m), 1.50–1.19 (4H, m), 0.98–0.57 (12H, m).

41. (A) N-4-(3H-2-Methylimidazo[4,5-c]pyridylmethyl)phenylsulphonyl-L-leucine benzyl ester and (B) N-4-(1H-2-methylimidazo[4,5-c]pyridylmethyl)phenylsulphonyl-L-leucine benzyl ester

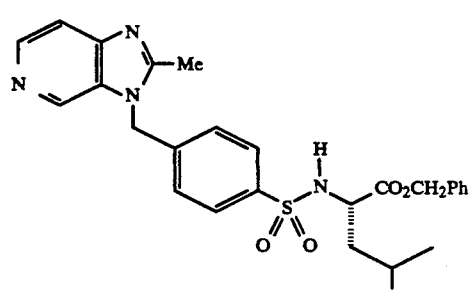

A

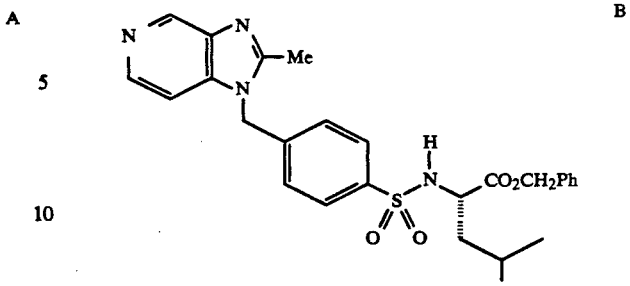

B

Regioisomer (A): Yellow crystalline solid (4% yield for last step after chromatography (silica: 5% methanol in DCM)): m.p. 108°–110° C.

Analysis calculated for C₂₇H₃₀N₄SO₄.0.4H₂O Requires C 63.11 H 6.04 N 10.90. Found C 63.18 H 5.99 N 10.84.

i.r. (CHCl₃) 2960, 1740, 1340, 1170 cm⁻¹.

delta$_H$ 8.61 (1H, s), 8 40 (1H, d, J 5.1 Hz), 7.74 (2H, d, J 8.4 Hz), 7.61 (1H, d, J 5.4 Hz), 7.32–7.20 (3H, m), 7.14–7.07 (4H, m), 6.31 (1H, d, J 8.4 Hz), 5.38 (2H, s), 4.83 (1H, d, J 12.a Hz), 4.76 (1H, d, J 12.4 Hz), 4.00 (1H, m), 2.57 (3H, s), 1.72 (1H, m), 1.48 (2H, t, J 7.1 Hz), 0.83 (3H, d, J 6.8 Hz), 0.80 (3H, d, J 6.7 Hz).

Regioisomer (B): White crystalline solid (4% yield): m.p. 180°–181° C.

Analysis calculated for C₂₇H₃₀N₄SO₄.0.2H₂O Requires C 63.34 H 6.02 N 10.94. Found C 63.42 H 5.98 N 10.95.

i.r. (CHCl₃) 2960, 1740, 1340, 1140 cm⁻¹.

delta$_H$ 9.03 (1H, s), 8.36 (1H, d, J 5.1 Hz), 7.78 (2H, d, J 8.5 Hz), 7.34–7.26 (3H, m), 7.19–7.13 (3H, m), 7.12 (2H, d, J 8.4 Hz), 5.52 (1H, d, J 9.9 Hz), 5.35 (2H, s), 4.84 (1H, d, J 12.3 Hz), 4.78 (1H, d, J 12.2 Hz), 4.00 (1H, dt, J 9.8, 7.3 Hz), 2.57 (3H, s), 1.74 (1H, m), 1.49 (2H, t, J 7.1 Hz), 0.86 (3H, d, J 6.6 Hz), 0.83 (3H, d, J 6.5 Hz).

42. (A) N-4-(3H-2-Methylimidazo[4,5-c]pyridylmethyl)phenylsulphonyl-L-leucine 2-ethoxyethyl ester and (B) N-4-(1H-2methylimidazo[4,5-c]pyridylmethyl)phenylsulphonyl-L-leucine 2ethoxyethyl ester

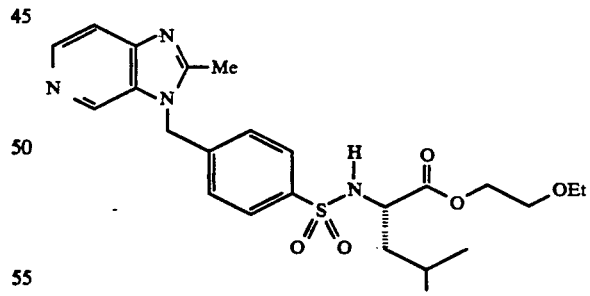

A

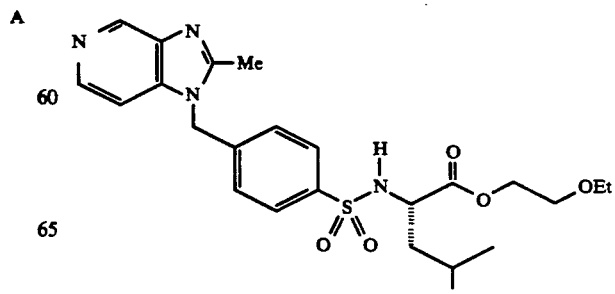

B

Regioisomer (A): Yellow crystalline solid (8% yield for last step after chromatography (silica: 6% methanol in DCM)): m.p. 98° C.

Analysis calculated for $C_{24}H_{32}N_4O_5S.0.8H_2O$ Requires C 57.31 H 6.73 N 11.14. Found C 57.30 H 6.46 N 10.97.

$delta_H$ 8.80 (1H, s), 8.60 (1H, s), 7.78 (2H, d, J 8.3 Hz), 7.69 (1H, d, J 4.8 Hz), 7.18 (2H, d, J 8.4 Hz), 6.12 (1H, d, J 9.7 Hz), 5.51 (2H, s), 4.00-3.87 (2H, m), 3.7S (1H, m), 3.44-3.30 (4H, m), 2.63 (3H, s), 1.77 (1H, m), 1.49 (2H, t, J 7.1 Hz), 1.11 (3H, t, J 7.0 Hz), 0.86 (3H, d, J 6.6 Hz), 0.82 (3H, d, J 6.5 Hz).

Regioisomer (B): White crystalline solid (S% yield): m.p. 176° C.

Analysis calculated for $C_{24}H_{32}N_4O_5S.10H_2O$ Requires C 56.90 H 6.76 N 11.06. Found C 56.63 H 6.38 N 10.8.

i.r. $(CHCl_3)$ 3010, 1725, 1340, 1100 cm$^{-1}$.

$delta_H$ 9.02 (1H, s), 8.37 (1H, d, J 4.6 Hz), 7.77 (2H, d, J 8.4 Hz), 7.17-7.11 (3H, m), 5.98 (1H, d, J 9.8 Hz), 5.38 (2H, s), 4.00-3.84 (2H, m), 3.74 (1H, m), 3.43-3.30 (4H, m), 2.58 (3H, s), 1.75 (1H,-m), 1.48 (2H, t, J 7.1 Hz), 1.10 (3H, t, J 7.0 Hz), 0.86 (3H, d, J 6.7 Hz), 0.82 (3H, d, J 6.5 Hz).

43. (A) N-4-(3H-2-Methylimidazo[4,5-c]pyridylmethyl)phenylsulphonyl-L-leucine 2-benzoxyethyl ester and (B) N-4-(1H-2methylimidazo[4,5-c]pyridylmethyl)-phenylsulphonyl-L-leucine 2-benzoxyethyl ester

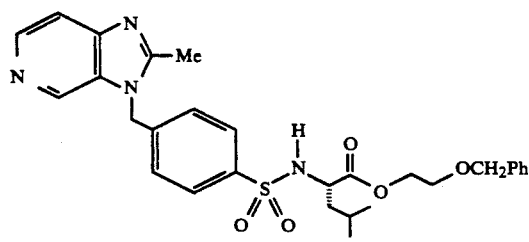

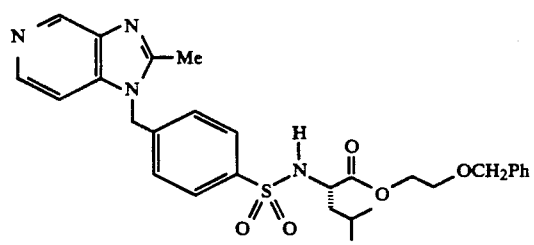

Regioisomers (A) and (B) were separated by chromatography (silica: 5% methanol in DCM).

Regioisomer (B): Colourless oil (2% yield for last step after chromatography).

i.r. $(CDCl_3)$ 2960, 1735, 1340, 1155 cm$^{-1}$.

$delta_H$ 9.05 (1H, s), 8.37 (1H, d, J 5.5 Hz), 7.75 (2H, d, J 8.3 Hz), 7.40-7.25 (5H, m), 7.14-7.04 (3H, m), 5.32 (2H, s), 5.15 (1H, br d, J 9.7 Hz), 4.43 (2H, dd, J 13.0, 12.2 Hz), 4.04-3.73 (3H, m), 3.50-3.36 (2H, m), 2.57 (3H, s), 1.78-1.62 (1H, m), 1.60-1.42 (2H, m), 0.88 (3H, d, J 6.7 Hz), 0.86 (3H, d, J 6.7 Hz).

$delta_C$ 172.00, 153.21, 145.52, 142.15, 140.04, 139.90, 137.60, 132.25, 128.49, 128.19, 127.92, 127.71, 126.69, 104.61, 73.11, 67.35, 64.43, 54.46, 46.84, 42.27, 24.28, 22.68, 21.34.

44. (A) N-4-(3H-2-Methylimidazo[4,5-c]pyridylmethyl)phenylsulphonyl-L-leucine 1-methyl-2-methoxyethyl ester and (B) N-4-(1H-2-methylimidazo[4,5-c]pyridylmethyl)phenylsulphonyl-L-leucine 1-methyl-2-methoxyethyl ester

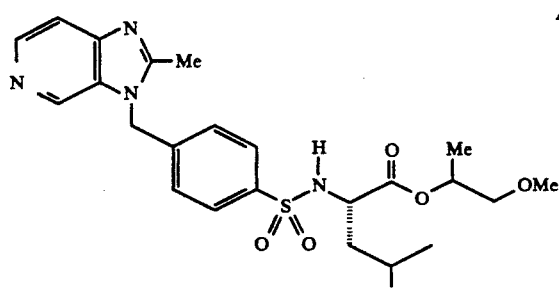

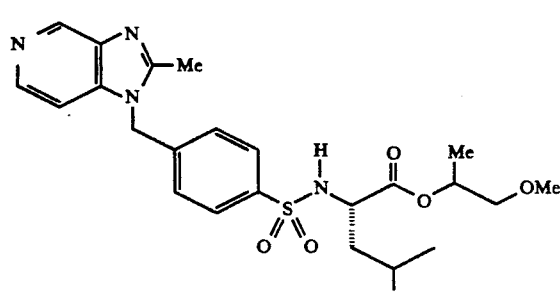

Regioisomers (A) and (B) were separated by chromatography (silica: 6% methanol in DCM).

Regioisomer (B): White crystalline solid (2% yield for last step after chromatography) m.p. 148°-150° C.

Analysis calculated for $C_{24}H_{32}N_4SO_5$ Requires C 58.99 H 6.61 N 11.47. Found C 58.95 H 6.71 N 11.0.

i.r. $(CHCl_3)$ 3015, 1735, 1340, 1115 cm$^{-1}$.

$delta_H$ 9.02 (1H, s), 8.37 (1H, d, J 5.5 Hz), 7.80-7.75 (2H, m), 7.12 (3H, br d, J 7.9 Hz), 5.83 (0.5H, d, J 9.4 Hz), 5.74 (0.5H, d, J 9.8 Hz), 5.36 (2H, s), 4.71 (0.5H, m), 4.59 (0.5H, m), 3.92 (1H, m), 3.24 (3H, s), 3.19-3.06 (2H, m), 2.58 (3H, s), 1.78 (1H, m), 1.48 (2H, t, J 7.1 Hz), 0.98 (1.5H, d, J 6.4 Hz), 0.89-0.84 (7.5H, m).

45. (A) N-4-(3H-2-Methylimidazo[4,5-c]pyridylmethyl)phenylsulphonyl-L-leucine 2-(2-ethoxyethoxy)ethyl ester and (B) N-4-(1H-2-methylimidazo[4,5-c]pyridylmethyl)phenylsulphonyl-L-leucine 2-(2-ethoxyethoxy)ethyl ester

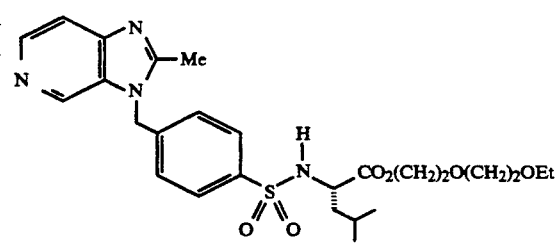

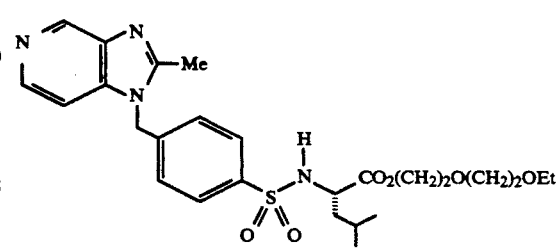

Regioisomer (A): Colourless oil (2% yield for last step after chromatography (silica: 4% methanol in DCM)).

i.r. (CHCl$_3$) 2080, 1735, 1340, 1160 cm$^{-1}$.

delta$_H$ 8.62 (1H, s), 8.44 (1H, d, J 5.5 Hz), 7.82 (2H, d, J 8.5 Hz), 7.64 (1H, d, J 5.5 Hz), 7.20 (2H, d, J 8.5 Hz), 5.46 (2H, s), 5.41 (1H, br s), 3.98–3.75 (3H, m), 3.53–3.38 (8H, m), 2.62 (3H, s), 1.77 (1H, m), 1.49 (2H, t, J 7.1 Hz), 1.18 (3H, t, J 7.0 Hz), 0.88 (3H, d, J 7.1 Hz), 0.86 (3H, d, J 7.0 Hz).

delta$_C$ 171.96, 155.03, 147.89, 142.38, 140.28, 139.85, 132.99, 132.27, 128.17, 126.92, 114.12, 70.44, 69.64, 68.39, 66.60, 64.31, 63.60, 54.48, 42.11, 24.26, 22.65, 21.33, 15.10, 13.94.

Regioisomer (B): White crystalline solid (1% yield).

delta$_H$ 9.05 (1H, s), 8.39 (1H, d, J 5.4 Hz), 7.81 (2H, d, J 8.4 Hz), 7.19–7.15 (3H, m), 5.40 (2H, s), 5.34 (1H, d, J 10.0 Hz), 4.01–3.74 (3H, m), 3.64–3.44 (8H, m), 2.60 (3H, s), 1.77 (1H, m), 1.49 (2H, t, J 7.1 Hz), 1.19 (3H, t, J 7.0 Hz), 0.88 (3H, d, J 6.6 Hz), 0.86 (3H, d, J 6.6 Hz).

delta$_C$ 172.07, 153.54, 142.09, 142.02, 140.36, 140.26, 139.99, 128.15, 127.03, 104.83, 71.70, 70.62, 70.39, 69.78, 68.49, 66.74, 64.45, 54.62, 47.01, 42.29, 24.38, 22.78, 21.47, 15.24, 14.09.

46. (A) N-4-(3H-2-Methylimidazo[4,5-c]pyridylmethyl)phenylsulphonyl-D,L-allylglycine ethyl ester and (B) N-4-(1H-2methylimidazo[4,5-c]pyridylmethyl)-phenylsulphonyl-D,L-allylglycine ethyl ester

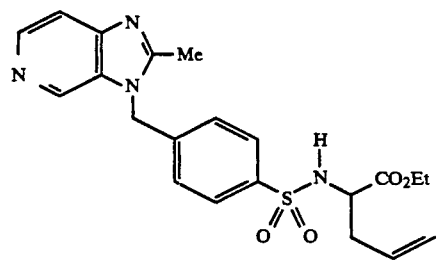

A

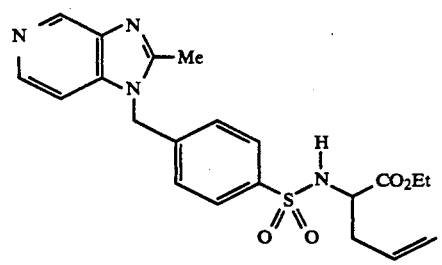

B

Regioisomer (A): Colourless oil (1.5% yield for last step after chromatography (silica: 2% methanol in DCM)).

delta$_H$ 8.62 (1H, s), 8.44 (1H, d, J 5.4 Hz), 7.80 (2H, d, J 8.1 Hz), 7.64 (1H, d, J 5.4 Hz), 7.17 (2H, d, J 8.1 Hz), 5.80–5.50 (2H, m), 5.45 (2H, s), 5.15–5.00 (2H, m), 4.20–3.80 (3H, m), 2.61 (3H, s), 2.46 (2H, t, J 6.5 Hz), 1.06 (3H, t, J 7.0 Hz).

Regioisomer (B): White crystalline solid (0.4% yield): m.p. 138° C.

i.r (CDCl$_3$) 1735, 1340, 1160 cm$^{-1}$.

delta$_H$ 9.05 (1H, s), 8.39 (1H, d, J 5.6 Hz), 7.80 (2H, d, J 8.2 Hz), 7.23–7.04 (3H, m), 5.70–5.45 (4H, m), 5.15–5.00 (2H, m), 4.10–3.80 (3H, m), 2.60 (3H, s), 2.47 (2H, t, J 6.3 Hz), 1.07 (3H, t, J 7.0 Hz).

47. (A) N-4-(3H-2-Methylimidazo[4,5-c]pyridylmethyl)phenylsulphonyl-L-methionine ethyl ester and (B) N-4-(1H-2-methylimidazo[4,5-c]pyridylmethyl)phenylsulphonyl-L-methionine ethyl ester

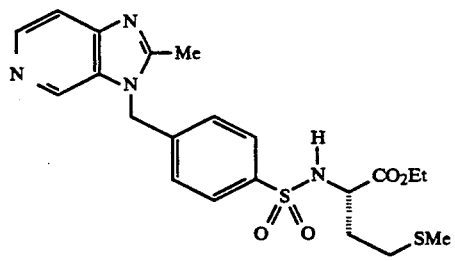

A

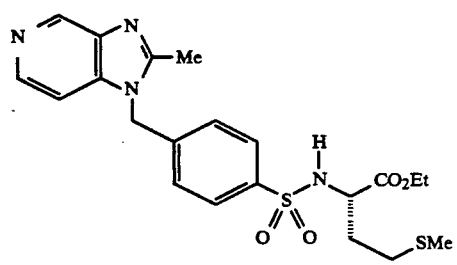

B

Regioisomer (A): Yellow crystalline solid (6% yield for last step after chromatography (silica: 5% methanol in DCM)): m.p. 187°–189° C.

Analysis calculated for C$_{21}$H$_{26}$N$_4$O$_4$S$_2$.1.00H$_2$O Requires C 52.48 H 5.87 N 11.66. Found C 52.50 H 5.50 N 11.29.

i.r. (CHCl$_3$) 3015, 1735, 1350, 1160 cm$^{-1}$.

delta$_H$ 8.62 (1H, s), 8.43 (1H, d, J 5.5 Hz), 7.78 (2H, d, J 8.4 Hz), 7.63 (1H, d, J 5.3 Hz), 7.16 (2H, d, J 8.4 Hz), 6.27 (1H, s), 5.44 (2H, s), 4.05 (1H, br s), 3.95–3.81 (2H, m), 2.60 (3H, s), 2.59–2.42 (2H, m), 2.01 (3H, s), 1.99–1.82 (2H, m), 1.02 (3H, t, J 7.2 Hz).

Regioisomer (B): Yellow crystalline solid (6% yield): m.p. 137°–138° C.

Analysis calculated for C$_{21}$H$_{26}$N$_4$O$_4$S$_2$ Requires C 53.69 H 5.75 N 11.93. Found C 53.70 H 5.63 N 11.79.

i.r. (CHCl$_3$) 3020, 1730, 1330, 1180 cm$^{-1}$.

delta$_H$ 9.06 (1H, s), 8.40 (1H, s), 7.83 (2H, d, J 8.4 Hz), 7.19–7.13 (3H, m), 5.48 (1H, d, J 9.0 Hz), 5.39 (2H, s), 4.06 (1H, m), 3.98–3.81 (2H, m), 2.60 (3H, s), 2.57–2.43 (2H, m), 2.05 (3H, s), 2.01–1.77 (2H, m), 1.06 (3H, t, J 7.1 Hz).

EXAMPLE 48

(A)
N-4-(1H-2-Methyl-5-fluorobenzimidazolylmethyl)-phenylsulphonyl-L-leucine methyl ester and (B) N-4-(1H-2-methyl-6-fluorobenzimidazolylmethyl)-phenylsulphonyl-L-leucine methyl ester

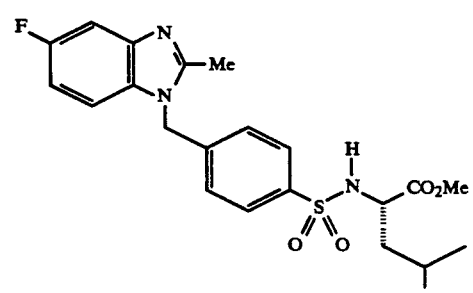

A

-continued

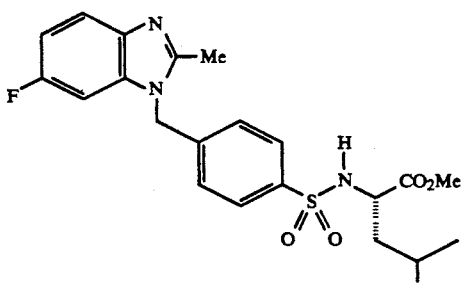

(a) 2-Methyl-5-fluorobenzimidazole

Ethyl acetimidate hydrochloride (37.1 g, 0.3 mol) was added to a stirred suspension of 4-fluoro-orthophenylenediamine (12.6 g, 0.1 mol) in ethanol (150 ml) at 0° C. The mixture was allowed to warm up to room temperature and stirred overnight. The solvent was removed under reduced pressure and the residue extracted into ethyl acetate (100 ml), washed with water (3×100 ml), dried over anhydrous magnesium sulphate, filtered and evaporated.

Crystallisation from ethyl acetate gave 2-methyl-5-fluorobenzimidazole (7.7 g, 51%) as a brown crystalline solid.

m.p. 177°–178° C.

delta$_H$ 7.46 (1H, dd, J 8.8, 4.7 Hz), 7.22 (1H, dd, J 8.9, 2.4 Hz), 6.98 (1H, ddd, J 9.7, 8.9, 2.4 Hz), 2.65 (3H, s).

(b) N-4-(1H-2-Methyl-5-fluorobenzimidazolylmethyl)phenylsulphonyl-L-leucine methyl ester and N-4-(1H-2-methyl-6-fluorobenzimidazolylmethyl)phenylsulphonyl-L-leucine methyl ester N-4-(1H-2-Methyl-5-fluorobenzimidazolylmethyl)-phenylsulphonyl-L-leucine methyl ester (A) and N-4-(1H-2-methyl-6-fluorobenzimidazolylmethyl)phenylsulphonyl-L-leucine methyl ester (B) were prepared by the method of Example 7 employing 2-methyl-5-fluorobenzimidazole in lieu of 2-methylbenzimidazole in the final step.

Regioisomers (A) and (B) were obtained as a mixture.

White crystalline solid (2% yield for last step after chromatography (silica: 4% methanol in DCM) and crystallisation from ethyl acetate): m.p. 196°–197° C.

Analysis calculated for C$_{22}$H$_{26}$FN$_3$O$_4$S Requires C 59.04 H 5.86 N 9.39. Found C 59.19 H 5.90 N 9.39.

delta$_H$ (CD$_3$OD) 7.74 (2H, dd, J 8.3, 1.6 Hz), 7.52 (0.6H, dd, J 8.8, 4.7 Hz), 7.35–7.22 (2.8H, m), 7.13 (0.6H, dd, J 8.9, 2.4 Hz), 6.97 (1H, m), 5.54 (0.8H, s), 5.51 (1.2H, s), 3.80 (1H, m), 3.23 (1.8H, s), 3.22 (1.2H, s), 2.55 (1.2H, s), 2.54 (1.8H, s), 1.60 (1H, m), 1.43–1.34 (2H, m), 0.82 (3H, d, J 6.6 Hz), 0.74 (3H, d, J 6.6 Hz).

EXAMPLE 49

(A) N-4-(1H-2-Methyl-5-fluorobenzimidazolylmethyl)-phenylsulphonyl-L-leucine ethyl ester and (B) N-4-(1H-2-methyl-6-fluorobenzimidazolylmethyl)-phenylsulphonyl-L-leucine ethyl ester

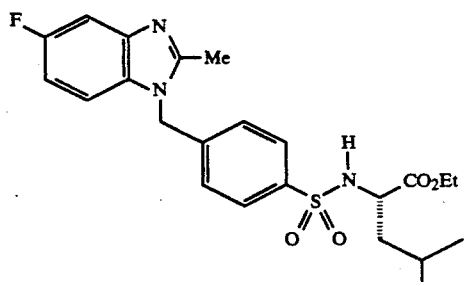

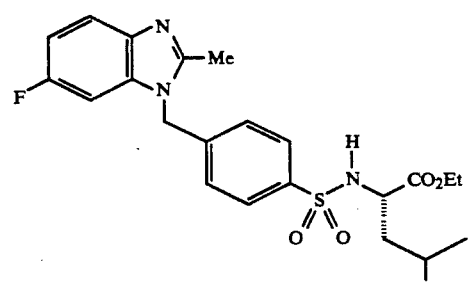

(A) N-4-(1H-2-methyl-5-fluorobenzimidazolylmethyl)phenylsulphonyl-L-leucine ethyl ester and (B) N-4-(1H-2-methyl-6-fluorobenzimidazolylmethyl)phenylsulphonyl-L-leucine ethyl ester were prepared by the method of Example 48 starting from L-leucine ethyl ester hydrochloride.

Regioisomers (A) and (B) were obtained as a 1:1 mixture.

White crystalline solid (14% yield for last step after chromatography (silica: 4% methanol in DCM)): m.p. 159°–161° C.

Analysis calculated for C$_{23}$H$_{28}$FN$_3$O$_4$S.0.2H$_2$O Requires C 59.39 H 6.15 N 9.03. Found C 59.36 H 6.11 N 9.01.

i.r. (CDCl$_3$) 2960, 1740, 1350, 1160 cm$^{-1}$.

delta$_H$ 7.79 (2H, dd, J 8.3, 1.5 Hz), 7.65 (0.5H, dd, J 8.8, 4.8 Hz), 7.41 (0.5H, dd, J 9.3, 2.3 Hz), 7.15 (2H, d, J 8.3 Hz), 7.07–6.91 (1.5H, m), 6.81 (0.5H, dd, J 8.5, 2.4 Hz), 5.36 (1H, s), 5.33 (1H, s), 5 15 (1H, m), 3.95–3.71 (3H, m), 2.57 (1.5H, s), 2.56 (1.5H, s), 1.77 (1H, m), 1.47 (2H, t, J 7.1 Hz), 1.03–0.97 (3H, m), 0.89 (3H, d, J 6.8 Hz), 0.86 (3H, d, J 6.7 Hz).

EXAMPLE 50

N-4-(1H-2-Methylbenzimidazolylmethyl)phenylsulphonyl-2-keto-3-amino-4-methylpentane

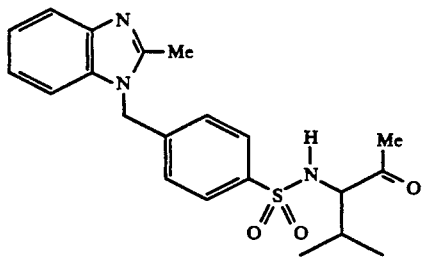

(a) N-Acetyl-2-keto-3-amino-4-methylpentane

A mixture of L-valine (25.0 g, 0.21 mol), acetic anhydride (60.5 ml, 0.64 mol), pyridine (52 ml, 0.64 mol) and 4-dimethylaminopyridine (2.0 g, 16.6 mmol) was heated at reflux overnight. The reaction mixture was allowed to cool to room temperature and methanol added with rapid stirring. The mixture was concentrated under reduced pressure to give an oil which was dissolved in diethyl ether (250 ml), washed with 2M hydrochloric acid (150 ml), saturated aqueous sodium hydrogen carbonate (150 ml) and brine (150 ml) dried over anhydrous magnesium sulphate, filtered and evaporated. Distillation under reduced pressure gave N-acetyl-2-keto-3-amino-4-methylpentane (6.3 g, 19%) as a viscous straw coloured oil (76°–78° C. @1.5 mmHg).

delta$_H$ 6.92 (1H, br d), 4.41 (1H, dd), 2.09 (1H, m), 2.03 (3H, s), 1.84 (3H, s), 0.80 (3H, d), 0.64 (3H, d).

(b) 2-Keto-3-amino-4-methylpentane hydrochloride

A mixture of N-acetyl-2-keto-3-amino-4-methylpentane (6.33 g, 40.3 mmol) and 6M hydrochloric acid (65 ml) was heated at reflux overnight. The reaction mixture was cooled to room temperature, ethanol (100 ml) was added and the mixture concentrated under reduced pressure The mixture was triturated with ether to give a precipitate which was collected by filtration. Crystallisation from acetone gave 2-keto-3-amino-4-methylpentane hydrochloride. (2.9 9, 63%) as a white crystalline solid.

m.p. 134°–135° C.

delta$_H$ 8.41 (3H, br s), 4.01 (1H, m), 3.72 (br s), 2.34 (1H, m), 2.24 (3H, s), 1.02 (3H, d), 0.87 (3H, s).

(c) N-4-(1H-2-Methylbenzimidazolylmethyl)phenylsulphonyl-2-keto-3-amino-4-methylpentane N-4-(1H-2-Methylbenzimidazolylmethyl)phenylsulphonyl-2-keto-3-amino-5-methylhexane was prepared by the method of Example 1 Step (b) and Step (c) starting from 2-keto-3-amino-4-methylpentane hydrochloride.

White crystalline solid (5% yield for last step after chromatography (silica: 5% methanol in DCM)): m.p. 140° C.

i.r. (CDCl$_3$) 1720, 1345, 1160 cm$^{-1}$.

delta$_H$ 7.72–7.62 (3H, m), 7.30–7.00 (5H, m), 5.76 (1H, d, J 8.8 Hz), 5.30 (2H, s), 3.75 (1H, dd, J 8.8, 3.8 Hz), 2.50 (3H, s), 2.12–2.00 (1H, m), 1.90 (3H, s), 0.95 (3H, d, J 6.7 Hz), 0.65 (3H, d, J 6.7 Hz).

delta$_C$ 2.05 41, 151.56, 142.48, 140.89, 139.53, 134.99, 127.77, 126.74, 122.42, 122.20, 119.19, 109.00, 66.95, 46.50, 29.82, 27.29, 19.74, 16.05.

EXAMPLE 51

(A) N-4-(3H-2-Methylimidazo[4,5-c]pyridylmethyl)phenylsulphonyl-2-keto-3-amino-4-methylpentane and (B) N-4-(1H-2-methylimidazo[4,5-c]pyridylmethyl)phenylsulphonyl-2-keto-3-amino-4-methylpentane

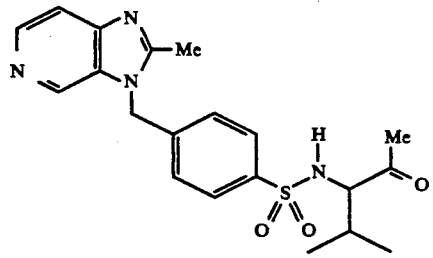

A

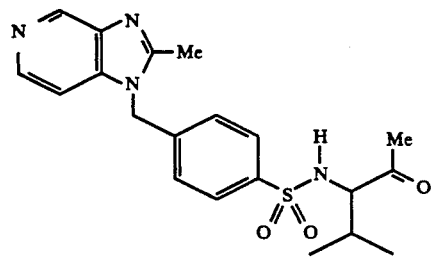

B (A) N-4-(3H-2-Methylimidazo[4,5-c]pyridylmethyl)phenylsulphonyl-2-keto-3-amino-4-methylpentane and (B) N-4-(1H-2methylimidazo[4,5-c]pyridylmethyl)phenylsulphonyl-2-keto-3-amino-4-methylpentane were prepared by the method of Example 50 employing 2-methylimidazo[4,5-c]pyridine in lieu of 2-methylbenzimidazole in the final step and obtained as a 1:1 mixture of regioisomers (A) and (B).

Orange viscous oil (4% yield for last step after chromatography (silica: 5% methanol in DCM)).

i.r. (CDCl$_3$) 1720, 1340, 1160 cm$^{31\ 1}$.

delta$_H$ 9.04 (0.5H, br s), 8.58 (0.5H, br s), 8.45 (0.5H, br d), 8.39 (0.5H, br d), 7.78 (2H, m), 7.20–7.07 (3H, m), 5.49–5.37 (3H, m), 3.89–3.77 (1H, m), 2.60 (1.5H, s), 2.57 (1.5H, s), 2.20–2.06 (1H, m), 1.94 (1.5H, s), 1.92 (1.5H, s), 1.04 (3H, dd), 0.70 (3H, d).

EXAMPLE 52

N-Methyl-N-4-(1H-2-methylbenzimidazolylmethyl)-phenylsulphonyl-L-leucine methyl ester

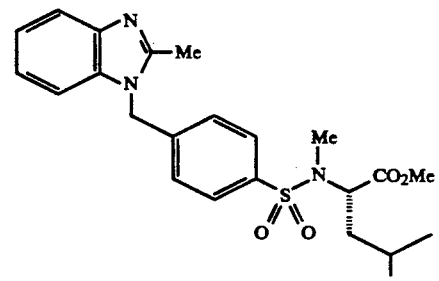

To a stirred solution of 4-(2-methylbenzimidazolylmethyl)phenylsulphonyl-L-leucine methyl ester (0.94 g, 2.2 mmol) in dry THF (50 ml) was added sodium hydride (60% dispersion in oil; 96 mg, 2.4 mmol) at room temperature under argon. After 1 h methyl iodide (0.41 ml, 6.6 mmol) was added and the reaction mixture stirred at room temperature overnight. The solvent was removed under reduced pressure and the residue extracted into ethyl acetate (100 ml), washed with water (100 ml) and brine (100 ml), dried over anhydrous magnesium sulphate, filtered and evaporated. Chromatography (silica: 4% methanol in DCM) gave N-methyl-N-4-(1H-2-methylbenzimidazolylmethyl)phenylsulphonyl-L-leucine methyl ester (220 mg, 23%) as a white crystalline solid.

m.p. 149° C.

Analysis calculated for $C_{23}H_{29}N_3O_4S.0.2H_2O$ Requires C 61.78 H 6.63 N 9.4. Found C 61.76 H 6.62 N 9.33.

i.r. $(CHCl_3)$ 3010, 1730, 1340, 1150 cm$^{-1}$.

delta$_H$ 7.68–7.62 (3H, m), 7.2–7.06 (5H, m), 5.27 (2H, s), 4.57 (1H, m), 3.28 (3H, s), 2.76 (3H, s), 2.48 (3H, s), 1.55–1.52 (3H, m), 0.89–0.86 (6H, m).

EXAMPLE 53

(A)
N-4-(3H-2-methylimidazo[4,5-c]pyridylmethyl)phenylsulphonyl-L-leucine ethyl ester and (B) N-methyl-N-4-(1H-2methylimidazo-4,5-c]pyridylmethyl)phenylsulphonyl-L-leucine ethyl ester

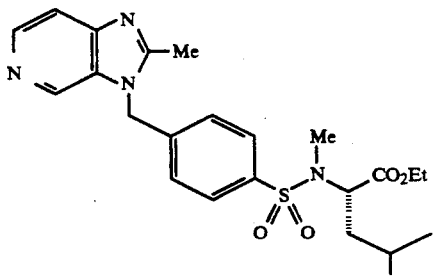

A

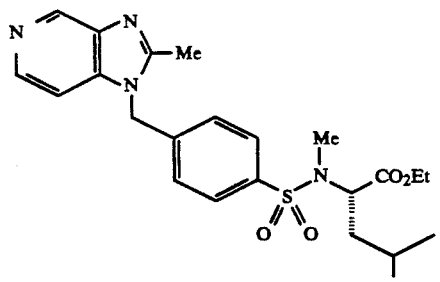

B (a) N-methyl-N-4-bromomethylphenylsulphonyl-L-leucine ethyl ester

N-4-Bromomethylphenylsulphonyl-L-leucine ethyl ester (2.0 g, 5.1 mmol) was dissolved in dry THF (30 ml) under argon and cooled to 0° C. Sodium hydride (60% dispersion in oil: 200 mg, 5.1 mmol) was added followed by methyl iodide (0.64 ml, 10.2 mmol) after a period of 5 mins. The reaction mixture was allowed to warm to room temperature and was stirred overnight. The reaction mixture extracted with ethyl acetate (2×50 ml). The combined organic extracts were washed with brine (50 ml), dried over anhydrous sodium sulphate, filtered and evaporated to give N-methyl-N-4-bromomethylphenylsulphonyl-L-leucine ethyl ester as an orange oil which was used directly in the next step without further purification.

(b) (A) N-Methyl-N-4-(3H-2-methylimidazo[4,5-c]pyridylmethyl)phenylsulphonyl-L-leucine ethyl ester and (B) N-methyl-N-4-(1H-2methylimidazo[4,5-c]pyridylmethyl)phenylsulphonyl-L-leucine ethyl ester 2-Methylimidazo[4,5-c]pyridine (1.00 g, 7.5 mmol) was dissolved in dry DMF (4 ml) and the mixture diluted with dry THF (50 ml) with stirring under argon. The solution was cooled to 0° C. and sodium hydride (60% dispersion in oil) (300 mg, 7.5 mmol) added. After 1 h a solution of N-methyl-N-4-bromomethylphenylsulphonyl-L-leucine ethyl ester (3.05 g, 7.5 mmol) in dry THF (10 ml) was added. The mixture was allowed to warm up to room temperature and stirred overnight. Saturated ammonium chloride (100 ml) was added and the product extracted using DCM (3×100 ml). The combined organic layers were washed with water (2×50 ml), dried over anhydrous sodium sulphate, filtered and the solvent removed. Chromatography (silica 4% methanol in DCM) gave N-methyl-N-4-(3H-2-methylimidazo[4,5-c]pyridylmethyl)phenylsulphonyl-L-leucine ethyl ester (regioisomer A) which eluted first followed by N-methyl-N-4-(1H-2-methylimidazo[4,5-c]pyridylmethyl)phenylsulphonyl-L-leucine ethyl ester (regioisomer B).

Regioisomer (A): Colourless oil (6% yield).

i.r. $(CDCl_3)$ 2210, 1725, 1330 cm$^{-1}$.

delta$_H$ 8.41 (1H, s), 8.22 (1H, d, J 5.6 Hz), 7.52 (2H, d, J 8.4 Hz), 7.42 (1H, d, J 6.1 Hz), 6.99 (2H, d, J 8.3 Hz), 5.28 (2H, s), 4.41 (1H, t, J 6.6 Hz), 3.59 (2H, q, J 7.1 Hz), 2.62 (3H, s), 2.42 (3H, s), 1.49–1.33 (3H, m), 0.80–0.63 (9H, m).

delta$_C$ 170.22, 154.70, 147.37, 141.80, 139.58, 138.64, 132.55, 131.99, 127.63, 126.33, 113.50, 60.41, 56.73, 46.57, 37.56, 29.37, 23.91, 22.56, 20.59, 13.48, 13.40.

Regioisomer (B): White crystalline solid from ethyl acetate (8% yield): m.p. 105° C.

Analysis calculated for $C_{23}H_{30}N_4O_4S$

Requires C 60.24 H 6.60 N 12.22. Found C 60.21 H 6.59 N 12.08.

i.r. (KBr) 2960, 1730, 1330, 1150 cm$^{-1}$.

$[\alpha]_D20$ −6.7 (c 2.0, $CDCl_3$).

delta$_H$ 9.03 (1H, s), 8.37 (1H, d, J 5.5 Hz), 7.76 (2H, d, J 8.4 Hz), 7.18–7.11 (3H, m), 5.39 (2H, s), 4.65–4.59 (1H, m), 3.83 (2H, q, J 7.1 Hz), 2.82, (3H, s), 2.59 (3H, s), 1.69–1.55 (3H, m), 1.02.(3H, t, J 7.1 Hz), 0.97 (3H, d, J 6.1 Hz), 0.95 (3H, d, J 6.2 Hz).

An alternative regioselective synthesis gives regioisomer (B) alone in an improved overall yield and involves the following steps.

(c) N-4-Azidomethylphenylsulphonyl-L-leucine ethyl ester

A solution of sodium azide (75.0 g, 1.054 mol) in water (150 ml) was added to a solution of the N-4-bromomethylphenylsulphonyl-L-leucine ethyl ester (89.0 g, 0.221 mol) in dichloromethane (150 ml). Benzyltriethylammonium chloride (10 g, 0.044 mol) was added and the heterogenous reaction mixture stirred vigorously for 60 h. The organic portion was separated, washed thoroughly with water, dried over anhydrous magnesium sulphate, filtered and concentrated to a golden oil, which crystallized on standing. The resulting white solid was freeze dried overnight to yield N-4-azidomethylphenylsulphonyl-L-leucine ethyl ester (78.2 g, 97%).

m.p. 75°–77° C.

Analysis calculated for $C_{15}H_{22}N_4O_4S$

Requires C 50.83 H 6.26 N 15.81. Found C 50.80 H 6.28 N 15.82.

i.r. (DCM) 2930, 2100, 1730, 1335, 1150 cm$^{-1}$.

$[\alpha]_D 25$ −16.4 (c 2.0, DCM).

delta$_{H(CDCl_3)}$ 7.86 (2H, d, J 8.4 Hz), 7.45 (2H, d, J 8.6 Hz), 5.13, (1H, d, J 10.0 Hz), 4.43 (2H, s), 3.98–3.84 (3H, m), 1.83–1.75 (1H, m), 1.49 (2H, dd, J 7.7, 6.7 Hz), 1.09 (3H, t, J 7.1 Hz), 0.91 (3H, d, J 6.7 Hz), 0.89 (3H, d, J 6.5 Hz).

(d) N-Methyl-N-4-azidomethylphenylsulphonyl-L-leucine ethyl ester

A 60% dispersion of sodium hydride in mineral oil (9.68 g, 0.242 mol) was added in portions to a solution of N-4-azidomethylphenylsulphonyl-L-leucine ethyl ester (78.0 g, 0.220 mol) in THF (200 ml) at 0° C. After stirring for 20 mins iodomethane (28 ml, 0.44 mol) was added slowly, and the reaction allowed to warm to ambient temperature overnight. Saturated ammonium chloride solution (ca. 15 ml) was added and the THF removed under reduced pressure. The resulting residue was taken up in dichloromethane, washed with saturated hydrogen carbonate solution then water, dried over anhydrous magnesium sulphate, filtered and concentrated to give N-methyl-N-4-azidomethylphenylsulphonyl-L-leucine ethyl ester as an orange oil (76.0 g, 94%).

Analysis calculated for $C_{16}H_{24}N_4O_4S$

Requires C 52.16 H 6.57 N 15.21. Found C 52.20 H 6.54 N 15.12.

i.r. (DCM) 2100, 1735, 1340, 1160 cm$^{-1}$.

$[\alpha]_D 20$ −15.3 (c 2.2, DCM).

delta$_{H(CDCl_3)}$ 7.83 (2H, dd, J 8.2, 1.6 Hz), 7.45 (2H, d, J 8.3 Hz), 4.71–4.65 (1H, m), 4.44 (2H, s), 3.96–3.86 (2H, m), 2.86 (3H, s), 1.67–1.58 (3H, m), 1.09 (3H, t, J 7.1 Hz), 0.99 (3H, d, J 5.0 Hz), 0.97 (3H, d, J 6.1 Hz).

(e) N-Methyl-N-4-aminomethylphenylsulphonyl-L-leucine ethyl ester

Triphenylphosphine (101.80 g, 0.388 mol) was added to a solution of N-methyl-N-4-azidomethylphenylsulphonyl-L-leucine ethyl ester (71.5 g, 0.194 mol) in a mixture of THF and water (4:1, 200 ml), and the reaction mixture stirred overnight at ambient temperature. The THF was removed under reduced pressure, and the product extracted with ethyl acetate, dried over anhydrous magnesium sulphate, filtered and concentrated to an orange oil. This was purified by chromatography over silica (1:2 EtOAc-hexane; EtOAc; 10% MeOH-EtOAc) to give N-methyl-N-4-aminomethylphenylsulphonyl-L-leucine ethyl ester (38 g, 58%) as a yellow oil.

delta$_{H(CDCl_3)}$ 7.76 (2H, dd, J 8.5, 1.7 Hz), 7.45 (2H, d, J 8.3 Hz), 4.71–4.65 (1H, m), 3.95 (2H, s), 3.95–3.85 (2H, m), 2.83 (3H, s), 1.95 (2H, br s), 1.68–1.57 (3H, m), 1.06 (3H, t, J 7.1 Hz), 0.97 (3H, d, J 5.4 Hz), 0.95 (3H, d, J 5.9 Hz).

(f) N-Methyl-N-4-(N′-3-nitropyrid-4-yl)aminomethylphenylsulphonyl-L-leucine ethyl ester 4-Chloro-3-nitropyridine (6.0 g, 38 mmol) was added to a stirred solution of N-methyl-N-4-aminomethylphenylsulphonyl-L-leucine ethyl ester (13.0 g, 38 mmol) and triethylamine (5.3 ml, 38 mmol) in chloroform (150 ml) at ambient temperature. The reaction mixture was stirred for 60 h, then washed with water, dried over anhydrous magnesium sulphate, filtered and the solvent removed under reduced pressure to leave a brown oil. This was purified by chromatography over silica (gradient elution 33% EtOAC-hexane, EtOAC) to give N-methyl-N-4-(N′-3-nitropyrid-4-yl)aminomethylphenylsulphonyl-L-leucine ethyl ester (10.9 g, 62%) as a yellow amorphous solid.

m.p. 71°–75° C.

i.r. (DCM) 3390, 1730, 1510, 1330 cm$^{-1}$.

$[\alpha]_D 25$ −13.8 (c 2.0, DCM).

delta$_{H(CDCl_3)}$ 9.00 (1H, s) 8.55 (1H, t, J 5.9 Hz), 8.04 (1H, d, J 6.1 Hz), 7.60 (2H, d, J 8.3 Hz), 7.32 (2H, d, J 8.3 Hz), 6.50 (1H, d, J 6.2 Hz), 4.57 (2H, d, J 5.9 Hz), 4.50–4.44 (1H, m), 3.75–3.62 (2H, m), 2.69 (3H, s), 1.45 (3H, br d), 0.86 (3H, t, J 7.1 Hz) 0.77 (6H, d, J 5.9 Hz).

(g) N-Methyl-N-4-(N′-3-aminopyrid-4-yl)aminomethylphenylsulphonyl-L-leucine ethyl ester A solution of N-methyl-N-4-(N′-3-nitropyrid-4-yl)aminomethylphenylsulphonyl-L-leucine ethyl ester (10.9 g, 0.023 mol) in ethanol (40 ml) was hydrogenated at 100 p.s.i. overnight in the presence of 10% palladium on charcoal (1.0 g). The catalyst was removed by filtration through GF/F filter paper, and the filtrate evaporated under reduced pressure to give N-methyl-N-4-(N′-3-aminopyrid-4-yl)aminomethylphenylsulphonyl-L-leucine ethyl ester (8.90 g, 87%) as a brown foam.

delta$_{H(CDCl_3)}$ 7.86 (1H, s) 7.83 (1H, s, J 5.5 Hz), 7.73 (2H, d, J 8.3 Hz), 7.41 (2H, d, J 8.3 Hz), 6.29 (1H, d, J 5.4 Hz), 5.04 (1H, m), 4.67–4.61 (1H, m), 4.44 (2H, d, J 5.6 Hz), 3.90–3.81 (2H, m), 2.84 (3H, s), 1.62–1 57 (5H, m), 1.04 (3H, t, J 7.1 Hz), 0.96 (3H, d, J 6.0 Hz), 0.95 (3H, d, J 6.1 Hz).

(h) N-Methyl-N-4-(1H-2-methylimidazo[4,5-c]pyridylmethyl)phenyl sulphonyl-L-leucine ethyl ester N-Methyl-N-4-(N′-3-aminopyrid-4-yl)aminomethylphenylsulphonyl-L-leucine ethyl ester (8.90 g, 20.5 mmol) was refluxed overnight in acetic anhydride (90 ml). The reaction mixture was allowed to cool, then methanol added cautiously until effervescence ceased. The volatiles were removed under reduced pressure and the residue partitioned between saturated sodium hydrogen carbonate solution and ethyl acetate. The organic portion was washed with saturated sodium hydrogen carbonate (×3), and water, dried over anhydrous sodium sulphate, filtered and concentrated to a brown oil. This was passed down a pad of silica (3% methanol in DCM) to remove baseline material, and the product further purified by medium pressure liquid chromatography (silica gel: 3% methanol in DCM plus trace of triethylamine) to give a pale yellow oil (5.12 g, 55%), which solidified slowly on standing. Recrystallisation from ethyl acetate/DIPE gave N-methyl-N-4-(1H-2-methylimidazo[4,5-c]pyridylmethyl)phenyl-sulphonyl-L-leucine ethyl ester as a white solid identical to that obtained above in step (b).

EXAMPLE 54

N-Methyl-N-4-(1H-2-methylbenzimidazolylmethyl)-phenylsulphonyl-L-leucine ethyl ester

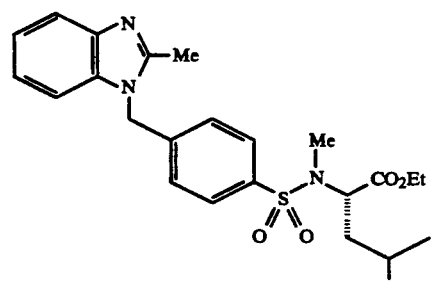

N-Methyl-N-4-(1H-2-methylbenzimidazolylmethyl)-phenylsulphonyl-L-leucine ethyl ester was prepared by the method of Example 53 Steps (a) and (b) employing 2-methylbenzimidazole in lieu of 2-methylimidazo[4,5-c]pyridine in Step (b).

White crystalline solid (22% yield for last step after chromatography (silica: 6% methanol in DCM)): m.p. 104° C.

Analysis calculated for $C_{24}H_{31}N_3O_4S$
Requires C 63.00 H 6.83 N 9.18 S 7.01. Found C 62.87 H 6.81 N 9.04 S 7.13.

i.r. (CHCl$_3$) 1760, 1340, 1145 cm$^{-1}$.

delta$_H$ 7.73 (3H, m,), 7.31–7.14 (5H, m), 5.39 (2H, s), 4.66–4.60 (1H, m), 3.80 (2H, q, J 7.1 Hz), 2.83 (3H, s), 2.58 (3H, s), 1.70–1.54 (3H, m), 1.01–0.93 (9H, m).

EXAMPLE 55

(A)
N-Methyl-N-4-(3H-imidazo[4,5-c]pyridylmethyl)-phenylsulphonyl-L-leucine ethyl ester and (B)
N-methyl-N-4-(1H-imidazo[4,5-c]pyridylmethyl)-phenylsulphonyl-L-leucine ethyl ester

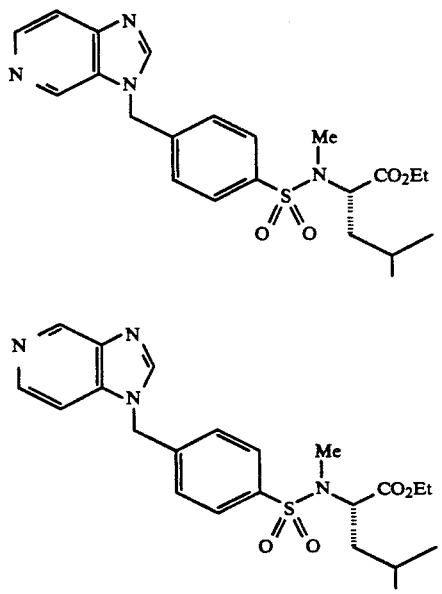

(A) N-Methyl-N-4-(3H-imidazo[4,5-c]pyridylmethyl)phenylsulphonyl-L-leucine ethyl ester and (B) N-methyl-N-4-(1H-imidazo[4,5-c]pyridylmethyl)phenylsulphonyl-L-leucine ethyl ester were prepared by the method of Example 53 Steps (a) and (b) employing imidazo[4,5-c]pyridine in lieu of 2-methylimidazo[4,5-c]pyridine in Step (b).

Regioisomer (A): White crystalline solid (7% yield for last step after chromatography (silica: 5% methanol in DCM)): m.p. 94° C.

Analysis calculated for $C_{22}H_{28}N_4O_4S.0.9H_2O$ Requires C 57.35 H 6.52 N 12.16 S 6.96. Found C 57.42 H 6.16 N 11.83 S 7.04.

i.r. (CHCl$_3$) 1730, 1335, 1150 cm$^{-1}$.

delta$_H$ 8.58 (1H, s,), 8.34 (1H, d, J 5.6 Hz), 8.06 (1H, s), 7.66–7.58 (3H, m), 7.19 (2H, d, J 8.4 Hz), 5.44 (2H, s), 4.55–4.46 (1H, m), 3.66 (2H, q, J 7.2 Hz), 2.71 (3H, s), 1.56–1.43 (3H, m), 0.90–0.76 (9H, m).

Regioisomer (B): White crystalline solid (9% yield): m.p. 133° C.

Analysis calculated for $C_{22}H_{28}N_4O_4S.0.2H_2O$ Requires C 58.96 H 6.39 N 12.50 S 7.07. Found C 59.00 H 6.31 N 12.47 S 7.07.

i.r. (CHCl$_3$) 1730, 1335, 1150 cm$^{-1}$.

delta$_H$ 8.99 (1H, s), 8.24 (1H, d, J 5.7 Hz), 7.98 (1H, s), 7.59 (2H, d, J 8.3 Hz), 7.18–7.05 (3H, m), 5.36 (2H, s), 4.52–4.43 (1H, m), 3.65 (2H, q, 7.1 Hz), 2.70 (3H, s), 1.58–1.39 (3H, m), 0.88–0.76 (9H, m).

EXAMPLES 56–63

The compounds of Examples 56–63 were prepared by the method of Example 53 Steps (a) and (b) starting from the appropriate 4-bromomethylphenylsulphonylamino acid derivative.

56. (A) N-Methyl-N-4-(3H-2-methylimidazo[4,5-c]pyridylmethyl)phenylsulphonyl-L-leucine i-propyl ester and (B) N-methyl-N-4-(1H2-methylimidazo[4,5-c]pyridylmethyl)phenylsulphonyl-L-leucine i-propyl ester

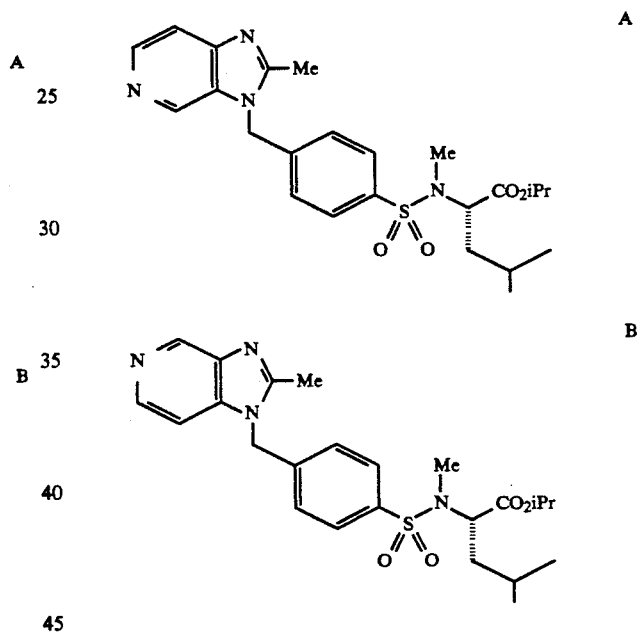

Regioisomer (A): White crystalline solid (7% yield for last step after chromatography (silica: 6% methanol in DCM)): m.p. 133°–135° C.

Analysis calculated for $C_{24}H_{32}N_4S.0.5H_2O$ Requires C 59.85 H 6.91 N 11.63. Found C 59.96 H 6.77 N 11.42.

i.r. (CHCl$_3$) 3020, 1740, 1340, 1190 cm$^{-1}$.

delta$_H$ 8.65 (1H, s), 8.41 (1H, s), 7.75 (2H, d, J 8.3 Hz), 7.64 (1H, d, J 5.0 Hz), 7.16 (2H, d, J 8.3 Hz), 5.46 (2H, s), 4.72–4.54 (2H, m), 2.80 (3H, s), 2.59 (3H, s), 1.63–1.52 (3H, m), 0.99–0.91 (12H, m).

Regioisomer (B): Yellow oil (7% yield).

Analysis calculated for $C_{24}H_{32}N_4O_4S.0.2H_2O$ Requires C 59.85 H 6.91 N 11.63. Found C 59.81 H 6.81 N 11.42.

i.r. (CDCl$_3$) 3010, 1760, 1170 cm$^{-1}$.

delta$_H$ 9.01 (1H, s), 8.35 (1H, d, J 5.3 Hz), 7.73 (2H, d, J 8.3 Hz), 7.11 (3H, br d, J 7.8 Hz), 5.36 (2H, s), 4.69–4.53 (2H, m), 2.81 (3H, s), 2.57 (3H, s), 1.63–1.52 (3H, m), 1.00–0.91 (12H, m).

57. (A) N-Methyl-N-4-(3H-2-methylimidazo[4,5-c]pyridylmethyl)phenylsulphonyl-L-leucine n-butyl ester and (B) N-methyl-N-4-(1H-2-methylimidazo[4,5- c]pyridylmethyl)phenylsulphonyl-L-leucine n-butyl ester

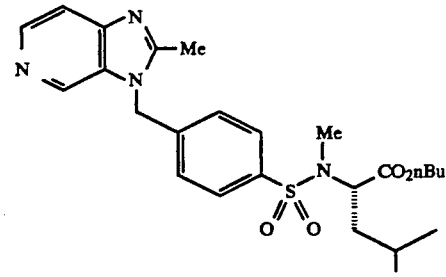

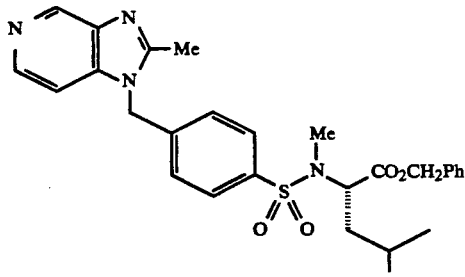

Regioisomer (A): Colourless oil (6% yield for last step after chromatography (silica: 4% methanol in DCM)):

Analysis calculated for C$_{25}$H$_{34}$N$_4$O$_4$S.0.3H$_2$O Requires C 61.03 H 7.09 N 11.39. Found C 60.94 H 7.01 N 11.10.

i.r. (CHCl$_3$) 1730, 1340, 1145 cm$^{-1}$.

delta$_H$ 8.56 (1H, s,), 8.38 (1H, d, J 5.5 Hz), 7.68 (2H, d, J 8.3 Hz), 7.57 (1H, d, J 5.4 Hz), 7.11 (2H, d, J 8.3 Hz), 5.40 (2H, s), 4.57 (1H, t, J 7.1 Hz), 3.68-3.78 (2H, m), 2.76 (3H, s), 2.54 (3H, s), 1.55 (3H, m), 1.35 (2H, m), 1.17 (2H, m), 0.88 (3H, d, J 6.1 Hz), 0.87 (3H, d, J 5.9 Hz), 0.78 (3H, t, J 7.2 Hz).

Regioisomer (B): Colourless oil (9% yield):

Analysis calculated for C$_{25}$H$_{34}$N$_4$O$_4$S.0.3H$_2$O Requires C 61.03 H 7.09 N 11.39 S 6.52. Found C 61.05 H 7.03 N 11.33 S 6.80.

i.r. (CHCl$_3$) 1730, 1335, 1145 cm$^{-1}$.

delta$_H$ 8.94 (1H, s), 8.28 (1H, d, J 5.6 Hz), 7.64 (2H, d, J 8.4 Hz), 7.09-7.04 (3H, m), 5.32 (2H, s), 4.55 (1H, m), 3.76-3.65 (2H, m), 2.75 (3H, s), 2.50 (3H, s), 1.53 (3H, m), 1.33 (2H, m), 1.15 (2H, m), 0.87 (6H, br d, J 4.6 Hz), 0.76 (3H, t, J 7.2 Hz).

58. (A) N-Methyl-N-4-(3H-2-methylimidazo[4,5-c]pyridylmethyl)phenylsulphonyl-L-leucine benzyl ester and (B) N-methyl-N-4-(1H-2methylimidazo[4,5-c]pyridylmethyl)phenylsulphonyl-L-leucine benzyl ester

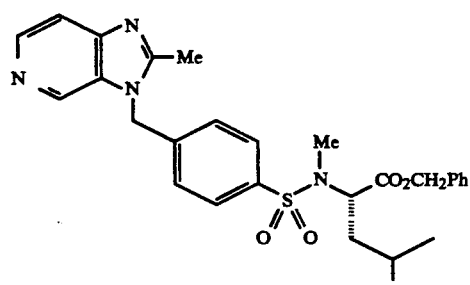

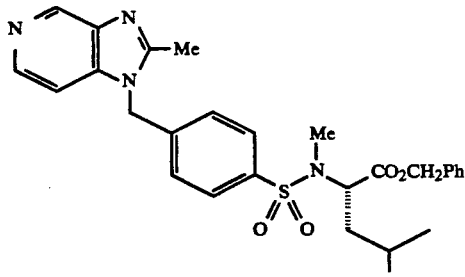

Regioisomer (A): Colourless oil (5% yield for last step after chromatography (silica: 5% methanol in DCM)):

i.r. (CDCl$_3$) 1735, 1340, 1150 cm$^{-1}$.

delta$_H$ 8.99 (1H, br s), 8.40 (1H, d, J 5.4 Hz), 7.76-7.65 (3H, m), 7.30-7.21 (3H, m), 7.20-7.12 (2H, m), 7.07 (2H, br d, J 8.3 Hz) 5.57 (2H, s), 4.89 (2H, s), 4.78-4.70 (1H, m), 2.78 (3H, s), 2.62 (3H, s), 1.68-1.57 (3H, m), 0.98-0.89 (6H, m).

Regioisomer (B): Pale yellow oil (2% yield):

Analysis calculated for C$_{28}$H$_{32}$N$_4$O$_4$S.1.6H$_2$O Requires C 61.21 H 6.46 N 10.20. Found C 61.10 H 6.06 N 10.15.

i.r. (CDCl$_3$) 1735, 1340, 1160 cm$^{-1}$.

delta$_H$ 9.06 (1H, br s), 8.38 (1H, d, J 5.0 Hz), 7.72 (2H, d, J 8.5 Hz), 7.33-7.25 (3H, m), 7.20-7.10 (3H, m), 7.04 (2H, d, J 8.3 Hz), 5.36 (2H, s), 4.88 (1H, d, J 12.5 Hz), 4.85 (1H, d, J 12.8 Hz), 4.80-4.70 (1H, m), 2.81 (3H, s), 2.58 (3H, s), 1.70-1.58 (3H, m), 1.00-0.90 (6H, m).

59. (A) N-Allyl-N-4-(3H-imidazo[4,5-c)pyridylmethyl)phenylsulphonyl-L-leucine ethyl ester and (B) N-allyl-N-4-(1H-imidazo-4,5-c]pyridylmethyl)phenylsulphonyl-L-leucine ethyl ester

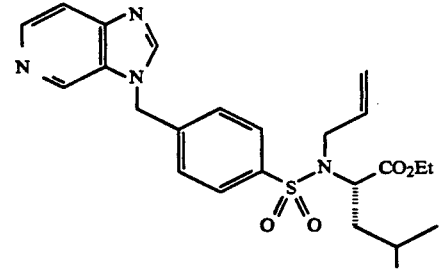

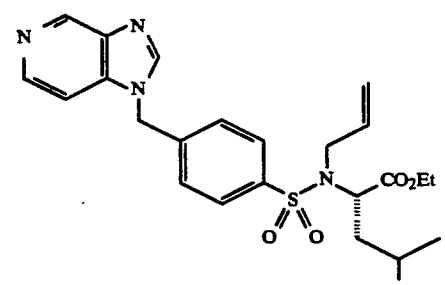

Regioisomer (A): White crystalline solid (9% yield for last step after chromatography (silica: 5-7% methanol in DCM) and crystallisation from ethyl acetate): m.p. 83°-84° C.

Analysis calculated for $C_{24}H_{30}N_4O_4S$ Requires C 61.26 H 6.43 N 11.91. Found C 60.92 H 6.45 N 11.76.

i.r. $(CHCl_3)$ 2960, 1730, 1340, 1150 cm$^{-1}$.

$delta_H$ 8.52 (1H, s), 8.29 (1H, d, J 5.5 Hz), 8.04 (1H, s), 7.59–7.54 (3H, m), 7.14 (2H, d, J 8.3 Hz), 5.76–5.60 (1H, m), 5.40 (2H, s), 5.03–4.90 (2H, m), 4.37 (1H, dd, J 9.3, 5.4 Hz), 3.71 (1H, dd, J 16.7, 5 4 Hz), 3.57–3.46 (3H, m), 1.54–1.41 (3H, m), 0.77 (3H, t, J 7.1 Hz), 0.75 (3H, d, J 7.1 Hz), 0.70 (3H, d, J 6.1 Hz).

Regioisomer (B): Yellow oil (15% yield)

i.r. $(CHCl_3)$ 2960, 1730, 1340, 1150 cm$^{-1}$.

$delta_H$ 8.85 (1H, s), 8.09 (1H, d, J 5.6 Hz), 7.92 (1H, s), 7.43 (2H, d, J 8.3 Hz), 7.02 (2H, d, J 8.3 Hz), 6.98 (1H, d, J 5.5 Hz), 5.67–5.51 (1H, m), 5.26 (2H, s), 4.95–4.81 (2H, m), 4.37 (1H, dd, J 9.3, 5.4 Hz), 3.79 (1H, dd, J 16.7, 5.4 Hz), 3.65–3.55 (3H, m), 1.44–1.32 (3H, m), 0.66 (3H, t, J 7.0 Hz), 0.65 (3H, d, J 6.9 Hz), 0.60 (3H, d, J 6.0 Hz).

$delta_C$ 170.30, 144.18, 142.47, 141.63, 140.38, 139.38, 139.20, 137.83, 134.75, 127.44, 126.89, 116.79, 104.95, 60.34, 57.53, 47.52, 38.21, 23.46, 21.93, 20.47, 13.17.

60. (A) N-Allyl-N-4-(3H-2-methylimidazo[4,5-c]pyridylmethyl)phenylsulphonyl-L-leucine ethyl ester and (B) N-allyl-N-4-(1H-2methylimidazo[4,5-c]pyridylmethyl)phenylsulphonyl-L-leucine ethyl ester

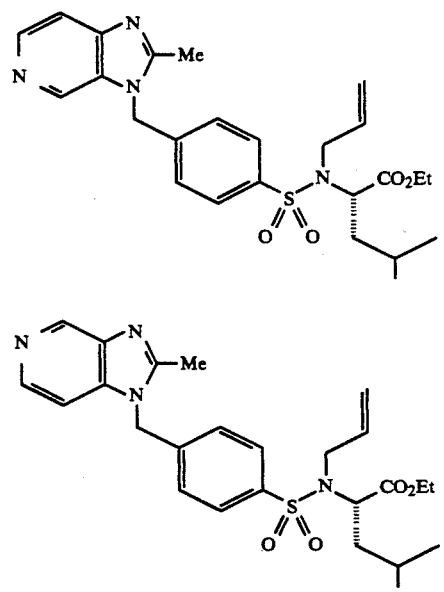

Regioisomer (A): Yellow oil (8% yield for last step after chromatography (silica: 6% methanol in DCM)):

i.r. $(CHCl_3)$ 2960, 1730, 1340, 1160 cm$^{-1}$.

$delta_H$ 8.48 (1H, s), 8.30 (1H, d, J 5.5 Hz), 7.62 (2H, d, J 8.4 Hz), 7.50 (1H, d, J 5.4 Hz), 7.04 (2H, d, J 8.4 Hz), 5.79–5.63 (1H, m), 5.34 (2H, s), 5.06–4.93 (2H, m), 4.41 (1H, dd, J 9.3, 5.3 Hz), 3.82 (1H, dd, J 16.7, 5.4 Hz), 3.73–3.59 (3H, m), 2.48 (3H, s), 1.57–1.42 (3H, m), 0.85 (3H, t, J 7.0 Hz), 0.79 (3H, d, J 6.1 Hz), 0.75 (3H, d, J 6.2 Hz).

$delta_C$ 170.56, 154.79, 147.43, 141.78, 139.64, 139.47, 132.59, 131.97, 127.83, 126.36, 116.99, 113.57, 60.57, 57.72, 47.76, 46.63, 38.47, 23.69, 22.16, 20.71, 13.55.

Regioisomer (B): White crystalline solid from ethyl acetate (12% yield): m.p. 132°–133° C.

i.r. $(CHCl_3)$ 2960, 1730, 1340, 1150 cm$^{-1}$.

$delta_H$ 8.97 (1H, s), 8.30 (1H, d, J 5.5 Hz), 7.69 (2H, d, J 8.4 Hz), 7.11–7.06 (3H, m), 5.87–5.71 (1H, m), 5.34 (2H, s), 5.14–5.01 (2H, m), 4.48 (1H, dd, J 9.4, 5.3 Hz), 3.89 (1H, dd, J 16.7, 5.4 Hz), 3.81–3.67 (3H, m), 2.53 (3H, s), 1.65–1.51 (3H, m), 0.95 (3H, t, J 7.2 Hz), 0.87 (3H, d, J 6.1 Hz), 0.82 (3H, d, J 6.3 Hz).

$delta_C$ 169.35, 151.96, 140.29, 140.03, 138.56, 138.24, 138.12, 133.82, 126.53, 125.22, 115.76, 103.36, 59.35, 56.53, 46.57, 45.20, 37.28, 22.51, 20.97, 19.51, 12.33.

61. (A) N-Methyl-N-4-(3H-2-methylimidazo[4,5-c]pyridylmethyl)phenylsulphonyl-D,L-allylglycine methyl ester and (B) N-methyl-N-4-(1H-2-methylimidazo[4,5-c]pyridylmethyl)phenylsulphonyl-D,L-allylglycine methyl ester

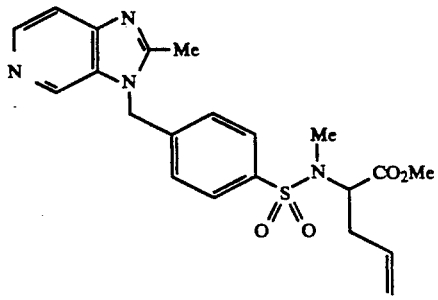

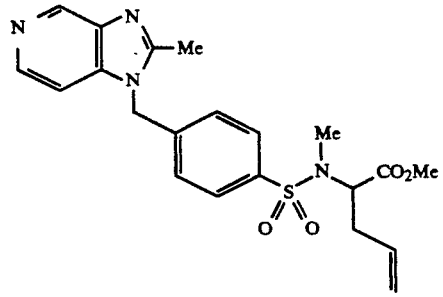

Regioisomer (A): Off-white crystalline solid (5% yield for last step after chromatography (silica: 5% methanol in DCM)): m.p. 142° C.

i.r. $(CDCl_3)$ 1740, 1340, 1155 cm$^{-1}$.

$delta_H$ 8.61 (1H, s), 8.43 (1H, d, J 5.5 Hz), 7.76 (2H, d, J 8.5 Hz), 7.63 (1H, d, J 5.4 Hz), 7.17 (2H, d, J 8.4 Hz), 5.76–5.58 (1H, m), 5.46 (2H, s), 5.18–5.03 (2H, m), 4.66 (1H, dd, J 9.9, 5.9 Hz), 3.45 (3H, s), 2.80 (3H, s), 2.72–2.56 (1H, m), 2.61 (3H, s), 2.45–2.29 (1H, m).

Regioisomer (B): Off-white crystalline solid (5% yield) m.p. 138° C.

Analysis calculated for $C_{21}H_{24}N_4O_4S$ Requires C 58.86 H 5.65 N 13.07. Found C 58.70 H 5.69 N 12.98.

i.r. $(CDCl_3)$ 1740, 1340, 1170 cm$^{-1}$.

$delta_H$ 9.03 (1H, s), 8.37 (1H, d, J 5.6 Hz), 7.76 (2H, d, J 8.4 Hz), 7.18–7.12 (3H, m), 5.76–5.58 (1H, m), 5.39 (2H, s), 5.18–5.04 (2H, m), 4.67 (1H, dd, J 9.8, 5.9 Hz), 3.46 (3H, s), 2.81 (3H, s), 2.72–2.54 (1H, m), 2.59 (3H, s), 2.46–2.30 (1H, m).

62. (A) N-Methyl-N-4-(3H-2-methylimidazo[4,5-c]pyridylmethyl)phenylsulphonyl-D,L-allylglycine ethyl ester and (B) N-methyl-N-4-(1H-2-methylimidazo[4,5-c]pyridylmethyl)phenylsulphonyl-D,L-allylglycine ethyl ester

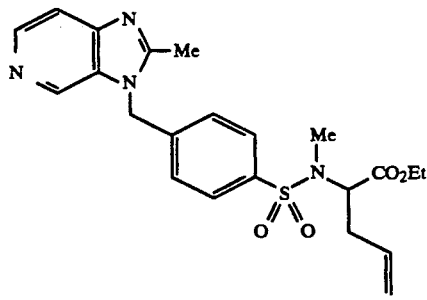

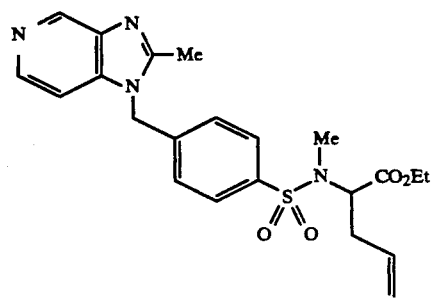

Regioisomer (A): Pale yellow oil (1% yield for last step after chromatography (silica: 5% methanol in DCM):

Analysis calculated for $C_{22}H_{26}N_4O_4S \cdot 1.3H_2O$ Requires C 56.71 H 6.19 N 12.02. Found C 56.80 H 5.87 N 11.66.

i.r. (CDCl$_3$) 1735 cm$^{-1}$.

delta$_H$ 8.76 (1H, br s), 8.45 (1H, d, J 5.3 Hz), 7.80 (2H, d, J 8.4 Hz), 7.71 (1H, d, J 5.6 Hz), 7.19 (2H, d, J 8.3 Hz), 5.80–5.60 (1H, m), 5.52 (2H, s), 5.20–5.05 (2H, m), 4.66 (1H, dd, J 9.8, 5.8 Hz), 3.93 (2H, q, J 7.1 Hz), 2.82 (3H, s), 2.74–2.60 (1H, m), 2.65 (3H, s), 2.50–2.32 (1H, m), 1.05 (3H, t, J 6.9 Hz).

Regioisomer (B): Pale yellow oil (1% yield):

Analysis calculated for $C_{22}H_{26}N_4O_4S \cdot 0.4H_2O$ Requires C 58.75 H 6.01 N 12.46. Found C 58.68 H 5.99 N 12.14.

i.r. (CDCl$_3$) 1730 cm$^{-1}$.

delta$_H$ 9.04 (1H, s), 8.38 (1H, d, J 5.6 Hz), 7.78 (2H, d, J 8.5 Hz), 7.20–7.12 (3H, m), 5.80–5.60 (1H, m), 5.41 (2H, s), 5.20–5.04 (2H, m), 4.67 (1H, dd, J 10.0, 5.8 Hz), 3.90 (2H, q, J 7.1 Hz), 2.82 (3H, s), 2.76–2.60 (1H, m), 2.61 (3H, s), 2.47–2.30 (1H, m), 1.04 (3H, t, J 7.3 Hz).

63. (A) N-Methyl-N-4-(3H-2-methylimidazo[4,5-c]pyridylmethyl)phenylsulphonyl-L-isoleucine allyl ester and (B) N-methyl-N-4-(1H-2-methylimidazo[4,5-c]pyridylmethyl)phenylsulphonyl-L-isoleucine allyl ester

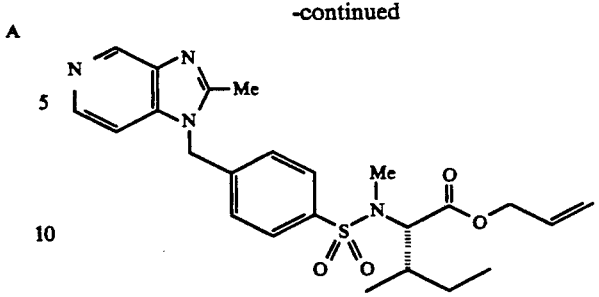

Regioisomer (A): Yellow oil (3% yield for last step after chromatography (silica: 5–7% methanol in DCM)):

i.r. (CDCl$_3$) 2950, 2220, 1735, 1610, 1400, 1340, 1150 cm$^{-1}$.

delta$_H$ 8.53 (1H, s), 8.36 (1H, d, J 5.5 Hz), 7.66 (2H, d, J 7.9 Hz), 7.56 (1H, d, J 5.5 Hz), 7.08 (2H, d, J 8.1 Hz), 5.61–5.45 (1H, m), 5.39 (2H, s), 5.07–4.98 (2H, m), 4.24–3.97 (3H, m), 2.78 (3H, s), 2.54 (3H, s), 1.92–1.72 (1H, m), 1.58–1.49 (1H, m), 1.16–0.95 (1H, m), 0.89–0.72 (6H, m).

delta$_C$ 169.44, 154.88, 147.68, 142.24, 139.73, 138.83, 132.82, 132.10, 130.93, 128.03, 126.52, 118.63, 113 94, 64.91, 63.13, 46.85, 33.50, 29.98, 24.75, 15.08, 13.80, 10.17.

Regioisomer (B) Yellow oil (3% yield):

i.r. (CDCl$_3$) 2950, 2220, 1735, 1610, 1340, 1150 cm$^{-1}$.

delta$_H$ 8.83 (1H, s), 8.17 (1H, d, J 5.0 Hz), 7.51 (2H, d, J 8.3 Hz), 7.00–6.93 (3H, m), 5.50–5.31 (1H, m), 5.24 (2H, s), 4.97–4.88 (2H, m), 4.12–4.02 (2H, m), 3.96–3.86 (1H; m), 2.68 (3H, s), 2.41 (3H, s), 1 82–1.62 (1H, m), 1.48–1.30 (1H, m), 1.06–0.86 (1H, m), 0.75–0.69 (6H, m).

delta$_C$ 169.18, 153.10, 141.58, 141.34, 139.74, 139.64, 139.39, 138.32, 130.65, 127.65, 126.31, 118.47, 104.43, 64.64, 62.86, 46.35, 33.24, 29.76, 24.51, 14.82, 13.52, 9.88.

EXAMPLE 64

(A)

N-Methyl-N-4-(3H-2-methylimidazo[4,5-c]pyridylmethyl)phenylsulphonyl-L-leucine morpholinoamide and (B)

N-methyl-N-4-(1H-2methylimidazo[4,5-c]pyridylmethyl)phenylsulphonyl-L-leucine morpholinoamide

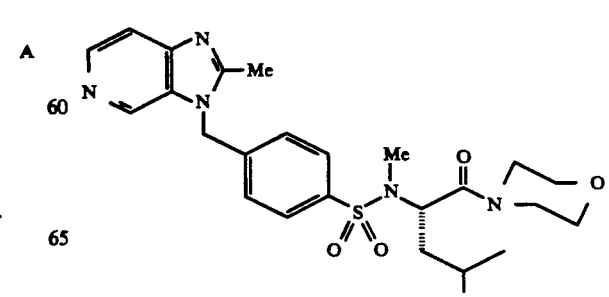

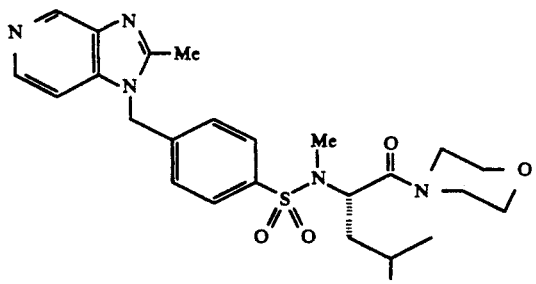

(A) N-Methyl-N-4-(3H-2-methylimidazo[4,5-c]pyridylmethyl)phenylsulphonyl-L-leucine morpholinoamide and (B) N-methyl-N-4-(1H-2-methylimidazo[ 4,5-c]pyridylmethyl)phenylsulphonyl-L-leucine morpholinoamide were prepared by the method of Example 25 Step (a), Example 11 Step (b), Example 5 Step (a) and Example 35 Step (b) starting from N-benzyloxycarbonyl-L-leucine p-nitrophenyl ester and morpholine.

Regioisomer (A): Pale yellow oil (3% yield for last step after chromatography (silica: 5% methanol in DCM)).

i.r. (CDCl$_3$) 1635, 1340, 1150 cm$^{-1}$.

delta$_H$ 8.68 (1H, br s), 8.43 (1H, br s), 7.73 (2H, d, J 8.3 Hz), 7.66 (1H, d, J 5.2 Hz), 7.19 (2H, d, J 8.4 Hz), 5.49 (2H, s), 4.85 (1H, t, J 7.4 Hz), 3.80–3.34 (8H, m), 2.85 (3H, s), 2.61 (3H, s), 1.70–1.57 (1H, m), 1.50–1.33 (1H, m), 1.15–0.99 (1H, m), 0.84 (3H, d, J 6.3 Hz), 0.83 (3H, d, J 6.5 Hz).

Regioisomer (B): Pale yellow oil (3% yield).

i.r. (CDCl$_3$) 1640, 1340, 1155 cm$^{-1}$.

delta$_H$ 9.02 (1H, s), 8.35 (1H, d, J 5.5 Hz), 7.69 (2H, d, J 8.3 Hz), 7.16–7.08 (3H, m), 5.39 (2H, s), 4.83 (1H, t, J 7.3 Hz), 3.80–3.34 (8H, m), 2.85 (3H, s), 2.57 (3H, s), 1.68–1 56 (1H, m), 1.48–1.34 (1H, m), 1 10–0.92 (1H, m), 0.83 (3H, d, J 6.6 Hz), 0.82 (3H, d, J 6.7 Hz).

EXAMPLE 65

N-Propyl-N-4-(3H-imidazo[4,5-c]pyridylmethyl)-phenylsulphonyl-L-leucine ethyl ester

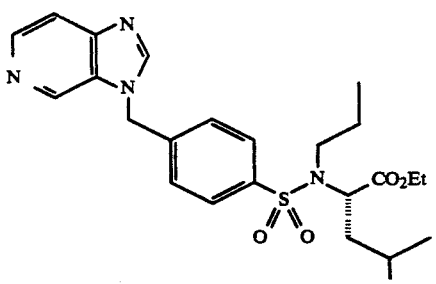

N-Allyl-N-4-(3H-imidazo[4,5-c]pyridylmethyl)-phenylsulphonyl-L-leucine ethyl ester (100 mg, 0.21 mmol) was dissolved in ethanol (15 ml) and added to a suspension of 10% palladium on carbon (100 mg) in ethyl acetate (10 ml) under argon. The flask was evacuated and a ballon of hydrogen was attached. The mixture was stirred at room temperature for 3 h, the catalyst filtered off and the solution concentrated under reduced pressure to give a yellow oil. Purification by chromatography (silica 4% methanol in DCM) gave N-propyl-N-4-(3H-imidazo[4,5-c]pyridylmethyl)- phenylsulphonyl-L-leucine ethyl ester (7 mg, 7%) as a colourless oil.

i.r. (CHCl$_3$) 2960, 1730, 1340, 1145 cm$^{-1}$.

delta$_H$ 8.71 (1H, s), 8.49 (1H, d, J 5.3 Hz), 8.09 (1H, s), 7.84 (2H, d, J 8.3 Hz), 7.76 (1H, d, J 5.7 Hz), 7.31 (2H, d, J 8.3 Hz), 5.52 (2H, s), 4.52 (1H, dd, J 9.4, 5.2 Hz), 3.81 (2H, q, J 7.1 Hz), 3.24–2.96 (2H, m), 1.82–1.46 (5H, m), 0.97 (3H, t, J 7.3 Hz), 0.95 (3H, d, J 5.7 Hz), 0.93 (3H, d, J 6.3 Hz), 0.84 (3H, t, J 7.3 Hz).

delta$_C$ 171.07, 149.06, 145.68, 142.40, 140.48, 139.10, 133.42, 128.43, 122.33, 115.29, 60.99, 58.29, 48.77, 47.83, 39.40, 24.40, 22.78, 21.42, 13.85, 11.38.

EXAMPLES 66 AND 67

The compounds of Examples 66 and 67 were prepared by the method of Example 65 starting from the regioisomers (A) and (B) of Example 60 respectively.

66. N-Propyl-N-4-(3H-2-methylimidazo[4,5-c]pyridylmethyl)phenylsulphonyl-L-leucine ethyl ester

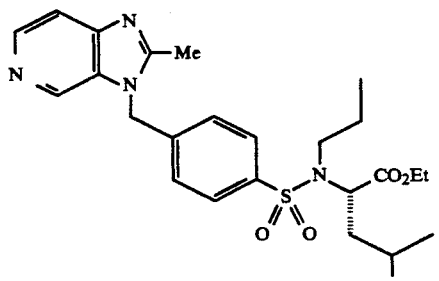

Off white crystalline solid (80% yield): m.p. 90°–91° C i.r. (CHCl$_3$) 2960, 1730, 1340, 1145 cm$^{-1}$.

delta$_H$ 8.57 (1H, s), 8.39 (1H, d, J 5.4 Hz), 7.73 (2H, d, J 8.3 Hz), 7.59 (1H, d, J 4.4 Hz), 7.12 (2H, d, J 8.3 Hz), 5.41 (2H, s), 4.48–4.42 (1H, m), 3.76 (2H, q, J 7.1 Hz), 3.18–2.91 (2H, m), 2.57 (3H, s), 1.76–1.41 (5H, m), 0.93 (3H, t, J 7.1 Hz), 0.87 (6H, br d, J 4.9 Hz), 0.79 (3H, t J 7.4 Hz).

delta$_C$ 170.96, 155.00, 147.81, 142.26, 140.10, 139.54, 132.91, 132.16, 128.26, 114.02, 60.87, 58.15, 47.69, 47.00, 39.30, 24.30, 22.68, 21.33, 13.88, 13.76, 11.28.

67. N-Propyl-N-4-(1H-2-methylimidazo[4,5-c]pyridylmethyl)phenylsulphonyl-L-leucine ethyl ester

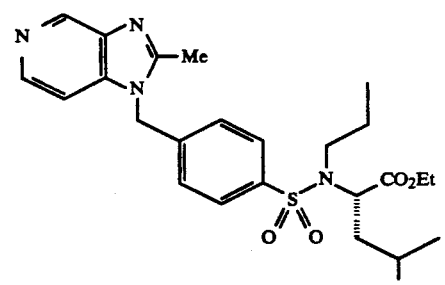

Off white crystalline solid (75% yield): m.p. 107°–108° C.

i.r. (CHCl$_3$) 2960, 1730, 1340, 1140 cm$^{-1}$.

delta$_H$ 8.96 (1H, s), 8.30 (1H, d, J 5.6 Hz), 7.69 (2H, d, J 8.4 Hz), 7.10–7.06 (3H, m), 5.34 (2H, s), 4.46–4.40 (1H, m), 3.74 (2H, q, J 7.0 Hz), 3.15–2.91 (2H, m), 2.53 (3H, s), 1.73–1.40 (5H, m), 0.93 (3H, t, J 7.2 Hz), 0.88 (3H, d, J 6.0 Hz), 0.86 (3H, d, J 6.1 Hz), 0.78 (3H, t, J 7.4 Hz).

deltac 170.88, 153.27, 141.83, 141.71, 140.02, 139.88, 139.54, 128.09, 126.44, 104.60, 60.75, 58.04, 47.61, 46.69, 39.22, 24.23, 22.60, 21.25, 13.76, 13.71, 11.20.

EXAMPLE 68

(A)
N-Methyl-N-4-(3H-2-methylimidazo[4,5-c]pyridylmethyl)phenylsulphonyl-2-keto-3-amino-4-methylpentane and (B)
N-Methyl-N-4-(1H-2-methylimidazo[4,5-c]pyridylmethyl)phenylsulphonyl-2-keto-3-amino-4-methylpentane

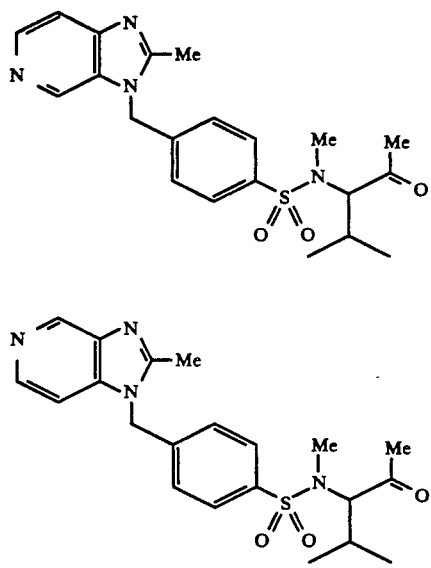

(A) N-Methyl-N-4-(3H-2-methylimidazo[4,5-c]pyridylmethyl)phenylsulphonyl-2-keto-3-amino-4-methylpentane and (B) N-methyl-N-4-(1H-2-methylimidazo[4,5-c]pyridylmethyl)phenylsulphonyl-2-keto-3-amino-4-methylpentane were prepared by the method of Example 1 Step (b) followed by Example 53 steps (a) and (b) starting from 2-keto-3-amino-4-methylpentane hydrochloride.

Regioisomers (A) and (B) were separated by column chromatography (silica: 5% methanol in DCM).

Regioisomer (B): Colourless oil (4% yield for last step after chromatography):

i.r. (CDCl₃) 1715, 1340, 1160 cm⁻¹.

delta$_H$ 8.94 (1H, s), 8.26 (1H, d, J 5.5 Hz), 7.66 (2H, d, J 8.3 Hz), 7.13–7.00 (3H, m), 5.33 (2H, s), 4.04 (1H, d, J 10.4 Hz), 2.65 (3H, s), 2.49 (3H, s), 2.07 (3H, s), 2.10–1.92 (1H, m), 0.76 (3H, d, J 6.6 Hz), 0.53 (3H, d, J 6.8 Hz).

deltac 205.06, 153.20, 141.87, 141.70, 139.98, 139.86, 139.59, 127.74, 126.70, 104.54, 68.30, 46.60, 29.89, 29.48, 25.97, 19.20, 19.08.

EXAMPLE 69

(A)
N-t-Butoxycarbonylmethyl-N-4-(3H-2-methylimidazo[4,5-c]pyridylmethyl)phenylsulphonyl-L-leucine ethyl ester and (B)
N-t-butoxycarbonylmethyl-N-4-(1H-2-methylimidazo[4,5-c]pyridylmethyl)phenylsulphonyl-L-leucine ethyl ester

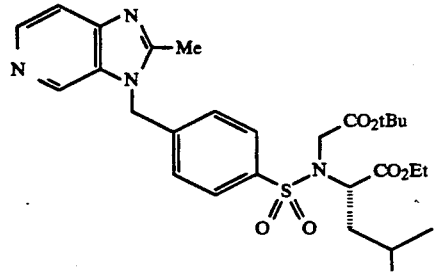

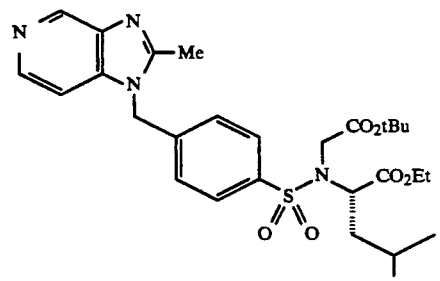

(a) N-t-Butoxycarbonylmethyl-N-4-bromomethylphenylsulphonyl-L-leucine ethyl ester N-4-Bromomethylphenylsulphonyl-L-leucine ethyl ester (1.0 g, 2.6 mmol) was dissolved in THF (50 ml) and the stirred resulting solution cooled to 0° C. and treated with potassium bis(trimethylsilyl)amide (0.5M in THF, 5 ml). The reaction mixture was stirred for 15 min, treated with t-butyl bromoacetate (0.75 ml, 0.5 mmol) and allowed to warm to room temperature overnight. The reaction mixture was then diluted with ethyl acetate and washed with brine. The organic layer was dried over anhydrous magnesium sulphate, filtered and concentrated under reduced pressure. Purification of the residue by chromatography (silica: 15% ethyl acetate in hexane) gave N-t-butoxycarbonylmethyl-N-4-bromomethylphenylsulphonyl-L-leucine ethyl ester (0.8 g, 54%) as a colourless oil.

delta$_H$ 7.89 (2H, d, J 8.2 Hz), 7.50 (2H, d, J 8.3 Hz), 4.60 (2H, s), 4.39–4.30 (1H, m), 4.11 (1H, d, J 18.5 Hz), 3.96 (1H, d, J 18.5 Hz), 3.90 (2H, q, J 7.1 Hz), 1.90–1 73 (1H, m), 1.60–1.39 (2H, m), 1.47 (9H, s) 1.08 (3H, t, J 7.0 Hz), 0.8S (3H, d, J 6.7 Hz), 0.83 (3H, d, J 6.5 Hz).

(b) (A) N-t-Butoxycarbonylmethyl-N-4-(3H-2-methylimidazo(4,5-c]pyridylmethyl)phenylsulphonyl-L-leucine ethyl ester and (B) N-t-butoxycarbonylmethyl-N-4-(1H-2-methylimidazo[4,5-c]pyridylmethyl-phenylsulphonyl-L-leucine ethyl ester (A) N-t-Butoxycarbonylmethyl-N-4-(3H-2-methylimidazo[4,5-c]pyridylmethyl)phenylsulphonyl-L-leucine ethyl ester and (B) N-t-butoxycarbonylmethyl-N-4-(1H-2-methylimidazo[4,5-c]pyridylmethyl-phenylsulphonyl-L-leucine ethyl ester were prepared by the procedure described in Example 35 Step (b)

utilising N-t-butoxycarbonylmethyl-N-4-bromomethylphenylsulphonyl-L-leucine ethyl ester in lieu of N-4-bromomethylphenylsulphonyl-L-leucine ethyl ester.

Regioisomer (A); Yellow oil (6% yield after chromatography (silica: 7% methanol in DCM)):

Analysis calculated for $C_{28}H_{38}N_4O_6S.0.8H_2O$ Requires C 58.68 H 6.96 N 9.78. Found C 58.76 H 6.72 N 9.73.

i.r. ($CHCl_3$) 2215, 1740 cm$^{-1}$.

$delta_H$ 8.51 (1H, s) 8.33 (1H, d, J 5.5 Hz), 7.78 (2H, d, J 8.3 Hz), 7.53 (1H, d, J 5.6 Hz), 7.09 (2H, d, J 8.2 Hz), 5.38 (2H, s), 4.18 (1H, t, J 8.0 Hz), 4.01 (1H, d, J 22.0 Hz), 3.85 (1H, d, J 22.0 Hz), 3.82–3.68 (2H, m), 2.52 (3H, s), 1.72–1.61 (1H, m), 1.45–1.28 (2H, m), 1.35 (9H, s), 0.92 (3H, t, J 7.1 Hz), 0.74 (3H, d, J 6.6 Hz), 0.68 (3H, d, J 6.5 Hz).

Regioisomer (B): Yellow oil (5% yield):

Analysis calculated for $C_{28}H_{38}N_4O_6S.0.9H_2O$ Requires C 58.50 H 6.98 N 9.75. Found C 58.45 H 6.68 N 9.74.

i.r. ($CHCl_3$) 2210, 1735 cm$^{-1}$.

$delta_H$ 8.95 (1H, s), 8.28 (1H, d, J 5.6 Hz), 7.79 (2H, d, J 8.3 Hz), 7.08 (3H, d, J 7.9 Hz), 5.33 (2H, s), 4.20 (1H, t 8.2 Hz), 4.03 (1H, d, J 22.0 Hz), 3.87 (1H, d, 22.0 Hz) 3.83–3.71 (2H, m), 2.51 (3H, s), 1.73–1.62 (1H, m), 1.51–1.32 (2H, m), 1.37 (9H, s), 0.95 (3H, t, J 7.1 Hz), 0.76 (3H, d, J 6.6 Hz), 0.70 (3H, d, J 6.5 Hz).

EXAMPLE 70

(A) N-Ethoxycarbonylmethyl-N-4-(3H-2-methylimidazo[4,5-c]pyridylmethyl)phenylsulphonyl-L-leucine ethyl ester and (B) N-ethoxycarbonylmethyl-N-4-(1H-2-methylimidazo[4,5-c]pyridylmethyl)phenylsulphonyl-L-leucine ethyl ester

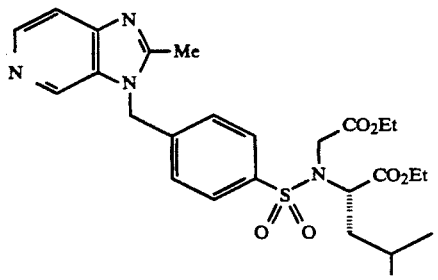

A

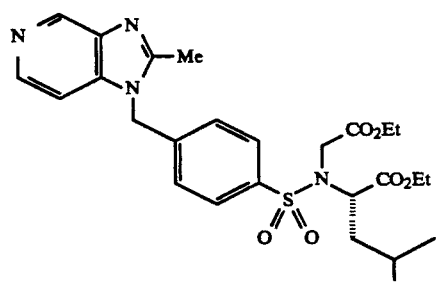

B (a) N-Ethoxycarbonylmethyl-N-4-bromomethylphenylsulphonyl-L-leucine ethyl ester N-4-Bromomethylphenylsulphonyl-L-leucine ethyl ester (2.0 g, 5.1 mmol) was dissolved in dry THF (50 ml) and the stirred solution was treated with potassium hydride (35% dispersion in oil, 0.583 g). After 20 min. ethyl bromoacetate (1.70 g, 10.2 mmol) was added and the resulting mixture allowed to stir overnight. Ethyl acetate and brine were added, and the organic layer was separated dried over anhydrous magnesium sulphate, filtered and concentrated under reduced pressure. Purification of the residue by chromatography (silica: 1:3 ethyl acetate/hexane) gave N-ethoxycarbonylmethyl-N-4-bromomethylphenylsulphonyl-L-leucine ethyl ester (1 89 g, 77%) as a colourless oil.

$delta_H$ 7.91 (2H, d, J 8.3 Hz), 7.52 (2H, d, J 8.2 Hz), 4.61, 4.49 (2H, 2s), 4.38, (1H. br t, J 7.2 Hz), 4.28–4.03 (4H, m), 3.92 (2H, q, J 7.1 Hz), 1.90–1.70 (1H, m), 1.60–1.48 (2H, m), 1.40–1.22 (3H, m), 1.10 (3H, t, J 7.0 Hz), 0.88 (3H, d, J 6.6 Hz), 0.84 (3H, d, J 6.6 Hz).

(b) (A) N-Ethoxycarbonylmethyl-N-4-(3H-2-methylimidazo4,5-c]pyridylmethyl)phenylsulphonyl-L-leucine ethyl ester and (B) N-ethoxycarbonylmethyl-N-4-(1H-2-methylimidazo[4,5-c]pyridylmethyl)phenylsulphonyl-L-leucine ethyl ester (A) N-Ethoxycarbonylmethyl-N-4-(3H-2-methylimidazo[4,5-c]pyridylmethyl)phenylsulphonyl-L-leucine ethyl ester and (B) N-ethoxycarbonylmethyl-N-4-(1H-2-methylimidazo[4,5-c]pyridylmethyl)phenylsulphonyl-L-leucine ethyl ester were prepared by the procedure described in Example 35 Step (b) utilising N-ethoxycarbonylmethyl-N-4-bromomethylphenylsulphonyl-L-leucine ethyl ester in lieu of N-4-bromomethylphenylsulphonyl-L-leucine ethyl ester.

Regioisomer (A): Yellow oil (4% yield after chromatography (silica: 5% methanol in DCM)):

Analysis calculated for $C_{26}H_{34}N_4O_6S.0.5H_2O$ Requires C 57.86 H 6.35 N 10.39. Found C 58.01 H 6.38 N 10.19.

i.r. ($CHCl_3$) 3690, 2960, 1735, 1600, 1390, 1155 cm$^{-1}$.

$delta_H$ 8.58 (1H, s), 8.41 (1H, d, J 5.5 Hz), 7.88 (2H, d, J 8.3 Hz), 7.61 (1H, d, J 5.3 Hz), 7.16 (2H, d, J 8.3 Hz), 5.44 (2H, s), 4.30–3.78 (7H, m), 2.58 (3H, s), 1.73–1.65 (1H, m), 1.54–1.44 (2H, m), 1.23 (3H, t, J 7.1 Hz), 1.01 (3H, t, J 7.1 Hz), 0.80 (3H, d, J 6.6 Hz), 0.74 (3H, d, 6.5 Hz).

Regioisomer (8): Yellow oil (4% yield);

Analysis calculated for $C_{26}H_{34}N_4O_6S.0.5H_2O$ Requires C 57.86 H 6.35 N 10.39. Found C 58.05 H 6.39 N 10.35.

i.r. ($CHCl_3$) 3680, 2960, 1735, 1610, 1585, 1340, 1280, 1155 cm$^{-1}$.

$delta_H$ 8.98 (1H, s), 8.31 (1H, d, J 5.4 Hz), 7.83 (2H, d, J 8.4 Hz), 7.13–7.09 (3H, m), 5.36 (2H, s), 4.27–3.78 (7H, m), 2.55 (3H, s), 1.71–1.66 (1H, m), 1.50–1.43 (2H, m), 1.21 (3H, dt, J 7.0, 1.5 Hz), 0.99 (3H, dt, J 7.1, 1.8 Hz), 0.79 (3H, d, J 6.5 Hz), 0.72 (3H, d, J 6.5 Hz).

EXAMPLE 71

(A) N-Methoxycarbonylmethyl-N-4-(3H-2-methylimidazo[4,5-c]pyridylmethyl)phenylsulphonyl-L-leucine ethyl ester and (B) N-methoxycarbonylmethyl-N-4-(1H-2-methylimidazo[4,5-c]pyridylmethyl)-phenylsulphonyl-L-leucine ethyl ester

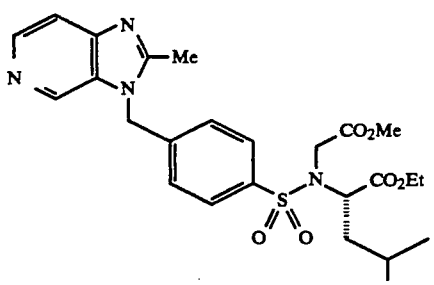

A

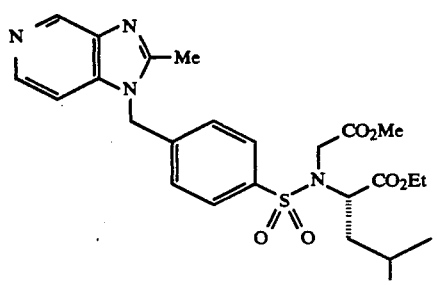

B (A) N-Methoxycarbonylmethyl-N-4-(3H-2-methylimidazo[4,5-c]pyridylmethyl)phenylsulphonyl-L-leucine ethyl ester and (B) N-methoxycarbonylmethyl-N-4-(1H-2-methylimidazo[4,5-c]pyridylmethyl)-phenylsulphonyl-L-leucine ethyl ester were prepared by the procedure described in Example 70 starting from methyl bromoacetate.

Regioisomer (A); Colourless oil (3% yield after chromatography (silica: 5% methanol in DCM):

i.r. (CHCl$_3$) 2960, 2220, 1735, 1610, 1345, 1155 cm$^{-1}$.

delta$_H$ 8.56 (1H, s), 8.39 (1H, d, J 5.7 Hz), 7.84 (2H, d, J 8.4 Hz), 7.59 (1H, d, J 5.5 Hz), 7.15 (2H, d, J 8.2 Hz), 5.43 (2H, s), 4.25 (1H, dd, J 8.2, 6.6 Hz), 4.18 (1H, d, J 18.9 Hz), 4.03 (1H, d, J 18.4 Hz), 3.89–3.78 (2H, m), 3.66 (3H, s), 2.57 (3H, s), 1.70–1.65 (1H, m), 1.49–1.42 (2H, m), 0.98 (3H, t, J 7.2 Hz), 0.79 (3H, d, J 6.6 Hz), 0.72 (3H, d, 6.4 Hz).

delta$_C$ 169.45, 168.52, 153.80, 146.40, 141.03, 138.89, 138.00, 131.61, 130.85, 127.46, 125.46, 125.26, 112.69, 59.79, 56.06, 50.84, 45.64, 44.80, 43.93, 37.95, 22.70, 21.08, 20.04, 12.52, 12.43.

Regioisomer (B): Yellow oil (2% yield):

i.r. (CHCl$_3$) 2960, 2220, 1735, 1610, 1340, 1155 cm$^{-1}$.

delta$_H$ 9.03 (1H, s), 8.36 (1H, d, J 5.5 Hz), 7.88 (2H, d, J 8.5 Hz), 7.17–7.11 (3H, m), 5.39 (2H, s), 4.28 (1H, dd, J 8.2, 6.5 Hz), 4.22 (1H, d, J 18.3 Hz), 4.06 (1H, d, J 18.5 Hz), 3.93–3.77 (2H, m), 3.70 (3H, s), 2.58 (3H, s), 1.76–1.64 (1H, m), 1.53–1.45 (2H, m), 1.03 (3H, t, J 7.1 Hz), 0.82 (3H, d, J 6.6 Hz), 0.76 (3H, d, J 6.5 Hz).

delta$_C$ 169.60, 168.61, 151.82, 140.74, 140.69, 138.80, 138.03, 127.50, 126.80, 125.22, 103.25, 59.79, 56.07, 50.85, 45.46, 43.92, 37.99, 22.73, 21.10, 20.09, 12.49.

EXAMPLE 72

(A) N-Methyl-N-3-chloro-4-(3H-2-methylimidazo[4,5-c]pyridylmethyl)phenylsulphonyl-L-leucine ethyl ester
and (B)
N-methyl-N-3-chloro-N-4-(1H-2-methylimidazo[4,5-c]pyridylmethyl)phenylsulphonyl-L-leucine ethyl ester

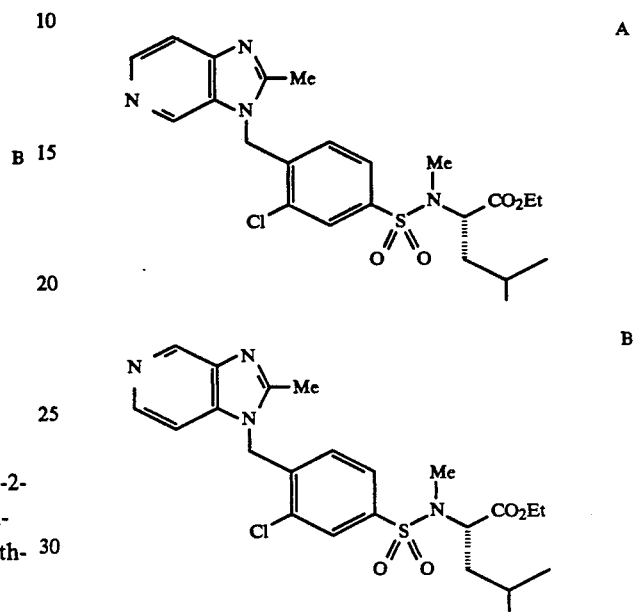

(a) 3-Chloro-4-bromomethylphenylsulphonyl chloride

N-Bromosuccinimide (13.76 g, 76 mmol) was added to a stirred solution of 3-chloro-4-toluenesulphonyl chloride (12 g, 76 mmol) in CCl$_4$ (120 ml) under argon. After one hour benzoyl peroxide (0.92 g, 3.8 mmol) was added and the reaction mixture refluxed overnight. The mixture was allowed to cool, the resulting white precipitate filtered off and the filtrate evaporated to a yellow oil. Purification of the residue by chromatography over silica gel (3% ethyl acetate in hexane) afforded 3-chloro-4-bromomethylphenylsulphonyl chloride (3.3 g, 14%) as a colourless oil.

delta$_H$ 8.30–7.05 (3H, m), 4.62 (2H, s).

(b) N-3-Chloro-4-bromomethylphenylsulphonyl-L-leucine ethyl ester

N-3-Chloro-4-bromomethylphenylsulphonyl-L-leucine ethyl ester was prepared following the procedure of Example 35 Step (a) utilising 3-chloro-4-bromomethylphenylsulphonyl chloride in lieu of 4-bromomethylphenylsulphonyl chloride.

Colourless oil (20% yield after purification by chromatography over silica gel (eluent 1:6 ethyl acetate/hexane):

delta$_H$ 7.88 (1H, d, J 3.0 Hz), 7.77–7.72 (1H, m), 7.62 (1H, d, J 8.2 Hz), 5.40 (1H, d, J 9.4 Hz), 4.71 (2H, s), 4.04–3.84 (3H, m), 1.90–1.71 (1H, m), 1.60–1.46 (2H, m), 1.17–1.09 (3H, m), 0.93 (6H, m).

(c) N-Methyl-N-3-chloro-4-bromomethylphenylsulphonyl-L-leucine ethyl ester

N-Methyl-N-3-chloro-4-bromomethylphenylsulphonyl-L-leucine ethyl ester was prepared following the procedure of Example 53 Step (a), utilising N-3-chloro-4-bromomethylphenylsulphonyl-L-leucine ethyl ester in lieu of N-4-bromomethylphenyl-L-leucine ethyl ester, as an oil which was used directly in the next step.

(d) (A) N-Methyl-N-3-chloro-4-(3H-2-methylimidazo[4,5-c]pyridylmethyl)phenylsulphonyl-L-leucine ethyl ester and (B) N-methyl-N-3-chloro-4-(1H-2-methylimidazo[4,5-c]pyridylmethyl)phenylsulphonyl-L-leucine ethyl ester (A) N-Methyl-N-3-chloro-4-(3H-2-methylimidazo[4,5-c]pyridylmethyl)phenylsulphonyl-L-leucine ethyl ester and (B) N-methyl-N-3-chloro-4-(1H-2-methylimidazo[4,5-c]pyridylmethyl)phenylsulphonyl-L-leucine ethyl ester were prepared by the method of Example 53 Step (b) utilising N-methyl-3-chloro-4-bromomethylphenylsulphonyl-L-leucine ethyl ester in lieu of N-methyl-4-bromomethylphenylsulphonyl-L-leucine ethyl ester and 3:1 THF/DMF as solvent.

Regioisomer (A): Colourless oil (2% yield after chromatography (silica: 6% methanol in DCM)):

i.r. (CHCl$_3$) 2960, 1730, 1610, 1335 cm$^{-1}$.

delta$_H$ 8.54 (1H, s), 8.43 (1H, d, J 5.5 Hz), 7.88 (1H, d, J 1.5 Hz), 7.63 (1H, d, J 5.5 Hz), 7.52 (1H, dd, J 8.2, 1.4 Hz), 6.58 (1H, d, J 8.2 Hz), 5.49 (2H, s), 4.61 (1H, m), 3.87 (2H, q, J 7.1 Hz), 2.79 (3H, s), 2.57 (3H, s), 1.61–1.59 (3H, m), 1.03 (3H, t, J 7.1 Hz), 0.98–0.91 (6H, m).

delta$_C$ 170.63, 155.17, 147.87, 142.51, 140.62, 137.01, 132.94, 132.12, 128.74, 127.11, 126.32, 114.17, 61.03, 57.31, 45.10, 37.93, 29.81, 24.31, 22.97, 20.93, 13.86, 13.74.

Regioisomer (B): Colourless oil (5% yield):

i.r. (CHCl$_3$) 2940, 1730, 1610, 1350 cm$^{-1}$.

delta$_H$ 8.97 (1H, s), 8.28 (1H, d, J 5.6 Hz), 7.81 (1H, d, J 1.8 Hz), 7.46 (1H, dd, J 8.2, 1.8 Hz), 7.04 (1H, dd, J 5.4, 0.8 Hz), 6.50 (1H, d, J 8.2 Hz), 5.39 (2H, s), 4.56 (1H, m), 3.82 (2H, q, J 7.1 Hz), 2.75 (3H, s), 2.51 (3H, s), 1.55 (3H, m), 1.00 (3H, t, J 7.2 Hz), 0.90 (3H, d, J 6.1 Hz), 0.89 (3H, d, J 6.1 Hz).

delta$_C$ 170.50, 153.28, 142.08, 141.90, 140.36, 139.67, 139.59, 136.95, 132.84, 128.52, 127.02, 126.11, 104.50, 60.67, 57.18, 44.75, 37.84, 29.70, 24.22, 22.87, 20.81, 13.78, 13.63.

EXAMPLES 73–74

The compounds of Examples 73–74 were prepared by the method of Example 53 Steps (c)–(h) employing the appropriate carboxylic anhydride in lieu of acetic anhydride in the final step.

73. N-Methyl-N-4-(1H-2-ethylimidazo[4,5-c]pyridylmethyl)phenylsulphonyl-L-leucine ethyl ester

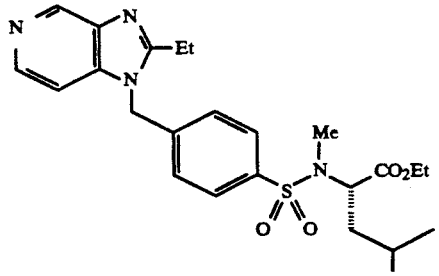

Off white crystalline solid (45% yield for last step after chromatography (silica: 4% methanol in DCM)): m.p. 107°–108° C.

i.r. (CDCl$_3$) 2960, 1730, 1340, 1150 cm$^{-1}$.

[α]$_D$25 −14.2 (c 1.5, EtOH).

delta$_H$ 9.09 (1H, s), 8.38 (1H, d, J 5.6 Hz), 7.77 (2H, d, J 8.5 Hz), 7.14 (3H, m), 5.41 (2H, s), 4.64 (1H, m), 3.84 (2H, q, J 7.2 Hz), 2.86 (2H, q, J 7.4 Hz), 2.83 (3H, s), 1.61 (3H, m), 1.46 (3H, t, J 7.4 Hz), 1.02 (3H, t, J 7.2 Hz), 0.96 (3H, d, J 6.0 Hz), 0.95 (3H, d, J 6.2 Hz).

delta$_C$ 170.70, 157.67, 141.98, 140.11, 139.76, 139.14, 128.06, 126.43, 104.61, 60.73, 57.06, 46.41, 37.96, 29.70, 24.28, 22.91, 20.94, 20.78, 11.12.

74. N-Methyl-N-4-(1H-2-n-pentylimidazo[4,5-c]pyridylmethyl)phenylsulphonyl-L-leucine ethyl ester

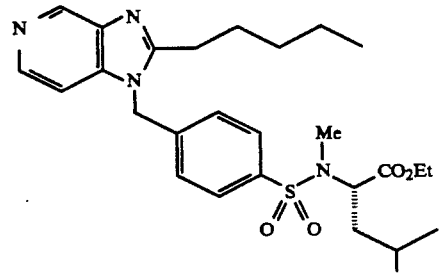

Yellow oil (12% yield for last step after chromatography (silica: 12% methanol in DCM)):

i.r. (CDCl$_3$) 2960, 1730, 1340, 1145 cm$^{-1}$.

delta$_H$ 9.07 (1H, s), 8.39 (1H, d, J 5.1 Hz), 7.76 (2H, d, J 8.7 Hz), 7.11 (3H, m), 5.41 (2H, s), 4.63 (1H, m), 3.84 (2H, q, J 7.1 Hz), 2.83 (1H, t, J 7.7 Hz), 2.82 (3H, s), 2.35 (1H, t, J 7.5 Hz), 1.86 (1H, m), 1.64 (2H, m), 1.33 (6H, m), 1.02 (3H, t, J 7.2 Hz), 0.95 (9H, m).

delta$_C$ 170.85, 157.39, 141.35, 140.36, 139.61, 139.39, 128.28, 126.43, 104.95, 60.87, 57.16, 46.64, 38.06, 31.45, 29.76, 24.38, 23.02, 22.91, 22.31, 22.25, 21.03, 13.84.

EXAMPLE 75

N-Acetyl-N-4-(3H-2-methylimidazo[4,5-c]pyridylmethyl)phenylsulphonyl-L-leucine ethyl ester

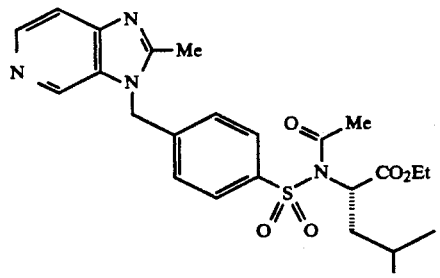

A 1M THF solution of sodium bis(trimethysilyl)amide (1.6 ml, 1.6 mmol) was added to a stirred solution of N-4-(3H-2-methylimidazo[4,5-c]pyridylmethyl)-phenylsulphonyl-L-leucine ethyl ester (0.70 g, 1.6 mmol) in dry THF (60 ml) under argon. The solution was cooled to 0° C. and acetyl chloride (0.11 ml) added. The mixture was allowed to warm up to room temperature and was stirred overnight. The solvent was removed under reduced pressure and the residue purified by chromatography (silica: 5% methanol in DCM) to give N-acetyl-N-4-(3H-2-methylimidazo[4,5-c]pyridylmethyl)phenylsulphonyl-L-leucine ethyl ester (0.36 g. 48%) as a colourless oil.

i.r. (CDCl$_3$) 2210, 1735, 1710, 1350, 1165 cm$^{-1}$.

delta$_H$ 8.57 (1H, s), 8.41 (1H, d, J 5.5 Hz), 8.03 (2H, d, J 8.5 Hz), 7.61 (1H, d, J 5.4 Hz), 7.21 (2H, d, J 8.3 Hz), 5.47 (2H, s), 4.95–4.90 (1H, m), 4.07 (2H, q, J 7.1 Hz), 2.58 (3H, s), 2.17 (3H, s), 2.18–2.04 (1H, m), 1.82–1.63 (2H, m), 1.11 (3H, t, J 7.2 Hz), 0.96 (3H, d, J 6.5 Hz), 0.92 (3H, d, J 6.5 Hz).

delta$_C$ 169.57, 169.16, 154.85, 147.63, 142.18, 141.28, 139.31, 132.68, 131.97, 128.93, 126.68, 113.91, 61.39, 58.67, 46.70, 39.22, 25.04, 24.79, 22.66, 21.82, 13.69.

EXAMPLE 76

(A) N-Ethoxycarbonyl-N-4-(3H-2-methylimidazo[4,5-c]pyridylmethyl)phenylsulphonyl-L-leucine ethyl ester and (B) N-ethoxycarbonyl-N-4-(1H-2-methylimidazo[4,5-c]pyridylmethyl)phenylsulphonyl-L-leucine ethyl ester

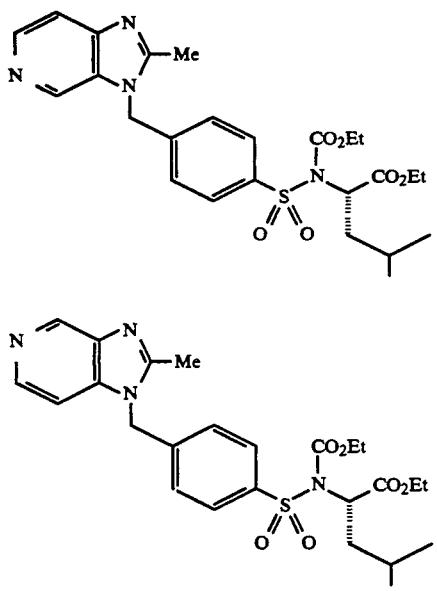

(a) N-Ethoxycarbonyl-N-4-bromomethylphenylsulphonyl-L-leucine ethyl ester

A solution of sodium bis(trimethylsilyl)amide (1M in THF, 39 ml, 39 mmol) was added to a stirred solution of N-4-bromomethylphenylsulphonyl-L-leucine ethyl ester (15.0 g, 38.2 mmol) in dry THF (150 ml) at room temperature under argon. The reaction mixture was cooled to 0° C. and ethyl chloroformate (3.7 ml, 38.3 mmol) was added. The mixture was allowed to warm to room temperature and was stirred overnight. The solvent was removed under reduced pressure and the residue taken up in ethyl acetate (150 ml) and aqueous ammonium chloride (100 ml) added. The organic layer was separated, washed with brine (100 ml), dried over anhydrous sodium sulphate, filtered and concentrated under reduced pressure. The residue was purified by chromatography (silica: 15% ethyl acetate in hexane) to give N-ethoxycarbonyl-N-4-bromomethylphenylsulphonyl-L-leucine ethyl ester (6.1 g, 34%) as a colourless oil.

delta$_H$ 8.06 (2H, d, J 8.4 Hz), 7.55 (2H, d, J 8.4 Hz), 5.14 (1H, dd, J 8.6, 5.6 Hz), 4.63 (3H, s), 4.22–4.03 (4H, m), 2.07–1.97 (2H, m), 1.78 (1H, m), 1.20 (3H, t, J 7.1 Hz), 1.10 (3H, t, J 7.2 Hz), 1.05 (3H, d, J 6.4 Hz), 1.00 (3H, d, J 6.4 Hz).

(b) (A) N-Ethoxycarbonyl-N-4-(3H-2-methylimidazo[4,5-c]pyridylmethyl)phenylsulphonyl-L-leucine ethyl ester and (B) N-ethoxycarbonyl-N-4-(1H-2-methylimidazo[4,5-c]pyridylmethyl)phenylsulphonyl-L-leucine ethyl ester (A) N-Ethoxycarbonyl-N-4-(3H-2-methylimidazo[4,5-c]pyridylmethyl)phenylsulphonyl-L-leucine ethyl ester and (B) N-ethoxycarbonyl-N-4-(1H-2-methylimidazo[4,5-c]pyridylmethyl)phenyl-sulphonyl-L-leucine ethyl ester were prepared by the procedure described in Example 35 Step (b) utilising N-ethoxycarbonyl-N-4-bromomethylphenylsulphonyl-L-leucine ethyl ester in lieu of N-4-bromomethylphenylsulphonyl-L-leucine ethyl ester.

Regioisomer (A): White foam (2% yield for last step after chromatography (silica: 5% methanol in DCM)): i.r. (CDCl$_3$) 2220, 1730, 1600, 1235, 1155 cm$^{-1}$.

delta$_H$ 8.55 (1H, s), 8.35 (1H, d, J 5.6 Hz), 7.94 (2H, d, J 8.5 Hz), 7.57 (1H, d, J 6.2 Hz), 7.13 (2H, d, J 8.4 Hz), 5.42 (2H, s), 5.03 (1H, dd, J 8.6, 5.7 Hz), 4.11–3.91 (4H, m), 2.54 (3H, s), 1.91 (2H, m), 1.67 (1H, m), 1.05 (3H, t, J 7.1 Hz), 0.99 (3H, t, J 7.1 Hz), 0.94 (3H, d, J 6.4 Hz), 0.89 (3H, d, J 6.6 Hz).

Regioisomer (B): White foam (2% yield): i.r. (CDCl$_3$) 2220, 1730, 1245, 1170 cm$^{-1}$.

delta$_H$ 8.91 (1H, s), 8.24 (1H, d, J 5.1 Hz), 7.90 (2H, d, J 8.4 Hz), 7.10–7.03 (3H, m), 5.33 (2H, s), 5.01 (1H, dd, J 8.6, 5.7 Hz), 4.09–3.87 (4H, m), 2.48 (3H, s), 1.89 (2H, m), 1.64 (1H, m), 1.04 (3H, t, J 7.1 Hz), 0.97 (3H, t, J 7.1 Hz), 0.92 (3H, d, J 6.4 Hz), 0.87 (3H, d, J 6.6 Hz).

delta$_C$ 169.72, 153.25, 151.00, 141.65, 141.48, 140.77, 139.98, 138.92, 129.69, 128.96, 125.96, 104.55, 63.32, 61.47, 58.02, 46.55, 39.04, 24.66, 22.97, 21.34, 13.73, 13.68, 13.57.

EXAMPLE 77

N-Methyl-N-4-(1H-2-methylimidazo[4,5-c]pyridylmethyl)phenylsulphonyl-L-leucine octadecyl ester

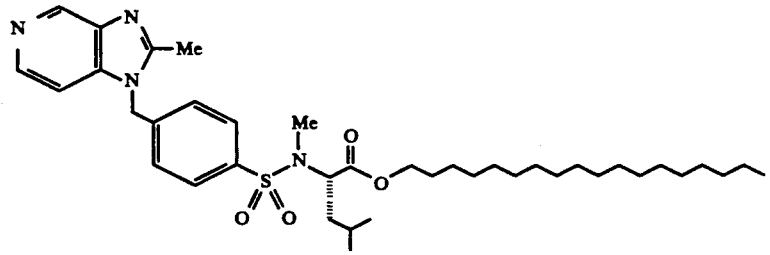

(a) N-Methyl-N-4-(1H-2-methylimidazo[4,5-c]pyridylmethyl)phenylsulphonyl-L-leucine Aqueous 2M potassium hydroxide solution (2.5 ml, 5 mmol) was added to a stirred solution of N-methyl-N-4-(1H-2-methylimidazo[4,5-c]pyridylmethyl)phenylsulphonyl-L-leucine ethyl ester (500 mg, 1.1 mmol) in ethanol (2 ml). The reaction mixture was stirred overnight at room temperature. The mixture was washed with DCM, acidified to pH 5.2 and extracted with DCM. The organic extracts were evaporated to give a colourless oil. Crystallisation from methanol gave N-methyl-N-4-(1H-2-methylimidazo[4,5-c]pyridylmethyl)phenylsulphonyl-L-leucine (191 mg, 40%) as a white crystalline solid.

i.r. (KBr) 3660-3150, 1720-1695, 1610, 1325, 1145 cm$^{-1}$.

delta$_{H (CD30D)}$ 8.36 (1H, s), 8.29 (1H, d, J 5.7 Hz), 7.77 (2H, d, J 8.4 Hz), 7.56 (1H, d, J 5.7 Hz), 7.27 (2H, d, J 8.3 Hz), 5.61 (2H, s), 4.55-4.49 (1H, m), 2.79 (3H, s), 2.59 (3H, s), 1.64-1.46 (3H, m), 0.89 (3H, d, J 6.0 Hz), 0.88 (3H, d, J 5.8 Hz).

(b) N-Methyl-N-4-(1H-2-methylimidazo[4,5-c]pyridylmethyl)phenylsulphonyl-L-leucine octadecyl ester 1-(3-Dimethylaminopropyl)-3-ethylcarbodiimide hydrochloride (139 mg, 0.7 mmol), pentafluorophenol (205 mg, 1.1 mmol) and N-methylmorpholine (80 µl, 0.7 mmol) were added to a stirred solution of N-methyl-N-4-(1H-2-methylimidazo[4,5-c]pyridylmethyl)phenylsulphonyl-L-leucine (240 mg, 0.6 mmol) in dry DMF (5 ml) at 0° C. The mixture was stirred for 1.5 h at 0° C. Octadecanol (300 mg, 1.1 mmol) was added and the mixture allowed to warm up to ambient temperature and was stirred for 60 h. Diethyl ether was added and the resultant mixture washed with water (×2), dried over anhydrous sodium sulphate, filtered and the solvent removed under reduced pressure to give a brown solid. Chromatogarphy (silica: 5% methanol in DCM) gave N-methyl-N-4-(1H-2-methylimidazo[4,5-c]pyridylmethyl)phenylsulphonyl-L-leucine octadecyl ester (125 mg, 3%) as a brown oil.

i.r. (CDCl$_3$) 2930, 1735, 1340, 1150 cm$^{-1}$.

delta$_H$ 9.00 (1H, br s), 8.33 (1H, br s), 7 70 (2H, d, J 8.3 Hz), 7.10 (3H, m), 5.36 (2H, s), 4.63-4.57 (1H, m), 3.83-3.66 (2H, m), 2.79 (3H, s), 2.55 (3H, s), 1.58-1.55 (3H, m), 1.41-1.31 (2H, m), 1.30-1.22 (30H, m), 0.92-0.82 (9H, m).

delta$_C$ 170.89, 153 30, 141.96, 141.86, 140.14, 139.61, 139.24, 128.12, 126.55, 104.62, 65.02, 57.12, 46.79, 38.11, 31.80, 29.73, 29.57, 29.45, 29.36, 29.23, 29.04, 28.23, 25.70, 24.35, 22.92, 22.56, 21.00, 13.99.

COMPARATIVE EXAMPLE

N-Cyclohexyl-N-methyl-4-(1H-imidazo[4,5-c]pyridylmethyl)benzamide

This compound is not within the scope of the invention: It has been included here as a comparative example. This compound was described in EP-A-0260613.

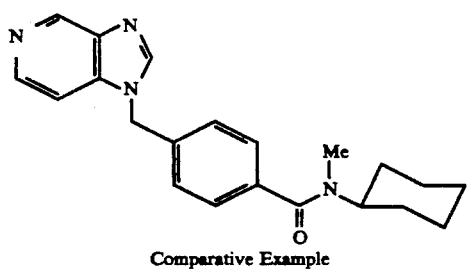

Comparative Example (a) N-Cyclohexyl-N-methyl-4-methylbenzamide

To an ice cold stirred solution of N-methylcylohexylamine (20 ml, 0.15 mol) and triethylamine (22 ml) in dry THF (100 ml) under argon was slowly added p-toluoyl chloride (20 ml, 0.15 mol). A white precipitate formed. The ice bath was removed and the mixture stirred at ambient temperature for 24 h. Ice cold 2M hydrochloric acid (100 ml) was added and the organic layer separated. The aqueous layer was extracted with ethyl acetate (3×100 ml). The combined organics were washed with brine (3×100 ml), dried over anhydrous sodium sulphate, filtered and evaporated to give the crude amide, which was crystallised from hexane to give N-cyclohexyl-N-methyl-4-methylbenzamide (30.9 g, 87%) as a white crystalline solid.

m.p. 70°-71° C.

i.r. (nujol) 2920, 1640 cm$^{-1}$.

delta$_H$ 7.26 (2H, d, J 8.0 Hz), 7.18 (2H, d, J 8.3 Hz), 4.50, 3.50 (1H, 2br m), 3.08-2.68 (3H, br m), 2.37 (3H, s), 1.93-0.93 (10H, br m).

(b) N-Cyclohexyl-N-methyl-4-bromomethylbenzamide

Utilising the procedure described in Example 1(a) employing N-cyclohexyl-N-methyl-4-methylbenzamide in lieu of p-toluenesulphonyl chloride and tetrachloromethane as solvent yielded crude N-cyclohexyl-N-methyl-4-bromomethylbenzamide (67%) as an orange waxy solid.

i.r. (CH2Cl$_2$) 2935, 1720 cm$^{-1}$.

delta$_H$ 7.46 (2H, d, J 8.1 Hz), 7.34 (2H, d, J 8.1 Hz), 4.51 (2H, s), 3.78, 3.50 (1H, 2br m), 2.97 (3H, br s), 1.89-0.98 (10H, br m).

(c) N-Cyclohexyl-N-methyl-4-(1H-imidazo[4,5-c]pyridylmethyl)benzamide

Sodium bis(trimethylsilyl)amide (22 ml of 1M solution in THF) was added to a stirred solution of imidazo[4,5-c]pyridine (2.60 g, 0.02 mol) in dry THF (200 ml) under argon. A fine white precipitate formed. After 90 m the mixture was treated with N-cyclohexyl-N-methyl-4-bromomethylbenzamide (6.20 g, 0.02 mol) dissolved in dry THF (50 ml). The mixture was allowed to warm to ambient temperature and stirred overnight. Methanol (1 ml) was added, followed by water and the product extracted using ethyl acetate (3×150 ml). The combined organic layers were washed with water (2×100 ml), dried over anhydrous potassium carbonate and the solvent removed to give the crude product. Flash chromatography (flash silica: 10% methanol in ethyl acetate) followed by repeated fractional crystallisation (6 times from ethyl acetate/DIPE) gave the desired regioisomer N-cyclohexyl-N-methyl-4-(1H-imidazo[4,5-c]pyridylmethyl)benzamide (0.39 g, 5%) as an off white crystalline solid.

m.p. 121°-123° C.

Analysis calculated for $C_{21}H_{24}N_4O.0.6H_2O$ Requires C 70.21 H 7.07 N 15.60. Found C 70.08 H 6.91 N 15.3.

i.r. (KBr) 3080, 2930, 1615 cm$^{-1}$.

delta$_H$ 9.17 (1H, s), 8.42 (1H, d, J 5.6 Hz), 8.03 (1H, s), 7.3 (2H, d, J 7.8 Hz), 7.27-7.19 (3H, m), 5.42 (2H, s), 4.50, 3.37 (1H, 2br m), 2.96, 2.76 (3H, 2br s), 2.05-1.02 (10H, br m).

Note on the Assignment of Regiochemistry

From a number of reactions used to prepare the exemplary compounds, which possess the imidazo[4,5-c]pyridine and 2-methylimidazo[4,5-c]pyridine moiety, two regioisomers are isolated; these regioisomers were usually separated by chromatography (silica gel: 1-10% methanol in DCM). The first regioisomer to elute is the 3H-imidazo[4,5-c]pyridyl or 3H-2-methylimidazo[4,5-c]pyridyl derivative and has been denoted as regioisomer (A) and the second to elute is the 1H-imidazo[4,5c-

]pyridyl or 1H-2-methylimidazo[4,5-c]pyridyl derivative and has been denoted as being regioisomer (B). The assignment of regiochemistry is based upon a differential n.O.e. NMR experiment conducted at 500 MHz on Example 35 regioisomer (B). Irradiation of the benzylic protons (delta 5.39 ppm) showed enhancements to the 2-methylimidazopyridine H-7 doublet signal (9%) and methyl protons (2%) and to the phenyl meta protons (8%). The regioisomers of the other Examples have been assigned by comparison of their 1H NMR spectra with that of Example 35 regioisomers (A) and (B).

PHARMACOLOGY EXAMPLE 1

The inhibition of 3H-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mM $MgCl_2$, 2 mM EDTA, pH 7.0), snap freezed in liquid $N_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor The prepared platelet membranes may be stored at $-70°$ C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained 3H-PAF (0.5 nM; 1-O-[3H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM $MgCl_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

%Inhibition = $[(TB-TBA)/SB] \times 100$ where the specific binding $SB = TB - NSB$.

Table 1 lists results from this assay for inhibition of 3H-PAF receptor binding for illustrative examples of the compounds of this invention. Also presented in Table 1 is the result for a comparative example (N-cyclohexyl-N-methyl-4-(1H-imidazo[4,5-c]pyridylmethyl)benzamide. This compound (a PAF antagonist described in EP-A-0260613) is not within the scope of the invention.

TABLE 1

Results for inhibition of 3H-PAF receptor binding

| Example | Inhibition of 3H-PAF binding $IC_{50}$ nM |
|---|---|
| 6 | 30 |
| 7 | 20 |
| 14 | 15 |
| 32B | 8 |
| 35B | 0.2 |
| 42A | 2 |
| 43B | 1 |
| 53B | 0.15 |
| 54 | 3 |
| 57B | 1 |
| Comparative Example | 10,000 |

PHARMACOLOGY EXAMPLE 2

The activity of the compounds of general formula I is also demonstrated in vivo by their ability to reverse the hypotension caused by an infusion of PAF in rats. Male Sprague-Dawley rats (300–350 g) were anaesthetised with a mixture of sodium pentobarbitone, 22.5 mg/kg and thiopental 62.5 mg/kg. Through a midline incision in the neck, the trachea was cannulated and the animals, breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng/kg/min was infused i.v. until a sustained fall in mean blood pressure of 50 mmHg was achieved. Test compounds were administered i.v. as a bolus and resulted in a dose dependent reversal of the PAF induced hypotension The peak of this reversal was measured and the dose to cause a 50% reversal of the hypotensive PAF response ($ED_{50}$) calculated by straight line interpolation and the results are presented in Table 2. Also presented in Table 2 is the result for a comparative example (N-cyclohexyl-N-methyl-4-(1H-imidazo[4,5- c]pyridylmethyl)benzamide. This compound (a PAF antagonist described in EP-A-0260613) is not within the scope of the invention.

TABLE 2

Results for inhibition of PAF-induced hypotension in the rat

| Example | ED$_{50}$ (μg/kg i.v.) |
|---|---|
| 7 | 11.6 |
| 12 | 21.0 |
| 32B | 2.1 |
| 53B | 0.5 |
| 56B | 0.6 |
| Comparative Example | 150 |

PHARMACOLOGY EXAMPLE 1

Rats were anaesthetised with a mixture of sodium pentobarbitone, 22.5 mg/kg, and thiopental, 62.5 mg/kg. The animals breathed spontaneously, air enriched with oxygen, and a carotid artery was cannulated for the measurement of blood pressure and heart rate. *E. Coli* acetone powder serotype No. 0111:84 (endotoxin) 100 mg/kg, was administered via a jugular vein; this resulted in a hypotension of approximately 50 mmHg which was sustained for up to 2 hours. Test compounds were administered i.v. via the other jugular vein as a bolus.

The dose which resulted in a 50% reversal of the endotoxin induced hypotension (ED$_{50}$) was calculated by straight line interpolation between the mean responses, calculated from bracketing doses, giving one dose per compound per animal. The results are presented in Table 3.

TABLE 3

Results for inhibition of endotoxin induced hypotension in the rat

| Example | ED$_{50}$ (μg/kg i.v.) |
|---|---|
| 32B | 15.5 |
| 35B | 2.9 |

PHARMACOLOGY EXAMPLE 4

The inhibition of PAF induced bronchoconstriction was measured in anaesthetised artificially ventilated guinea-pigs (450–500 g) using a modified version of the Konzett-Rössler technique (Konzett M and Rössler R, *Naunym-Schmiedeb. Arch. Exp. Pathol. Pharmakol.*, 1940, 197, 71) Male Dunkin-Hartley guinea-pigs were anaesthetised with urethane, 1.6 g/kg. Through a midline neck incision, the trachea was cannulated and the animal ventilated with a constant tidal volume set between 5 and 15 ml, to give a tracheal inflation pressure of 15 mmHg at a rate of 40 per minute. A carotid artery was cannulated for the measurement of blood pressure and heart rate and both jugular veins were cannulated, one for the infusion of PAF and the other for the administration of test compounds. PAF, 40 ng/kg/min in saline with 0.25% bovine serum albumin, was infused i.v. to produced a 100% increase in tracheal inflation pressure, and bronchoconstrictor effects were determined. Test compounds were administered p.o. (10 mg/kg) 1 hour before the infusion of PAF was started whilst the animals were conscious. The percentage inhibition of PAF-induced bronchoconstriction (ED$_{50}$) was determined and the results are presented in Table 4.

TABLE 4

Results for inhibition of PAF-induced Bronchoconstriction in the guinea pig

| Example | % Inhibition (10 mg/kg p.o.) |
|---|---|
| 53(B) | 91 |
| 56(B) | 72 |
| 60(B) | 60 |
| 69(B) | 60 |

We claim:
1. A compound of general formula I;

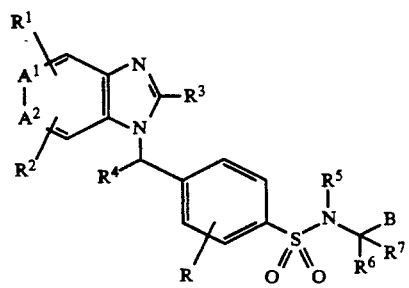

wherein
A$^1$ is =N—, =CH— or =CR$^1$—;
A$^2$ is —N=, —CH= or —CR$^2$=;
provided that, when one of A$^1$ and A$^2$ is a nitrogen atom, the other of A$^1$ and A$^2$ is other than a nitrogen atom;
R represents hydrogen, —C$_1$-C$_6$ alkyl, —C$_2$-C$_6$ alkenyl, halogen or —OC$_1$-C$_6$ alkyl;
each of R$^1$ and R$^2$ independently represents hydrogen, —C$_1$-C$_6$ alkyl, —C$_2$-C$_6$ alkenyl, halogen, —CN, —CO$_2$H, CO$_2$C$_1$-C$_6$ alkyl, —CONH$_2$, —CHO, —CH$_2$OH, CF$_3$, —OC$_1$-C$_6$ alkyl, —SC$_1$-C$_6$ alkyl, —SC$_1$-C$_6$ alkyl, —SO$_2$C$_1$-C$_6$ alkyl, —NH$_2$, —NHCOMe or NO$_2$ or R$^1$ and R$^2$ together with the carbon atoms to which they are attached form a fused phenyl ring;
R$^3$ represents hydrogen, —C$_1$-C$_6$ alkyl, —C$_2$-C$_6$ alkenyl, —C$_2$-C$_6$ alkynyl, —OC$_1$-C$_6$ alkyl, —SC$_1$-C$_6$ alkyl, —(C$_1$-C$_6$ alkyl)OC$_1$-C$_6$ alkyl, —(C$_1$-C$_6$ alkyl)SC$_1$-C$_6$ alkyl, CF$_3$, -(C$_1$-C$_6$ alkyl)phenyl, —C$_3$-C$_8$ cycloalkyl, —C$_4$-C$_8$ cycloalkenyl, —(C$_1$-C$_6$ alkyl)C$_3$-C$_8$ cycloalkyl, —(C$_1$-C$_6$ alkyl)-C$_4$-C$_8$ cycloalkenyl or thiophenyl;
R$^4$ represents hydrogen, —C$_1$-C$_6$ alkyl, —C$_2$-C$_6$ alkenyl, —C$_2$-C$_6$ alkynyl, CO$_2$C$_1$-C$_6$ alkyl, —SC$_1$-C$_6$ alkyl, —(C$_1$-C$_6$ alkyl)SC$_1$-C$_6$ alkyl, —(C$_1$-C$_6$ alkyl)OC$_1$-C$_6$ alkyl, —(C$_1$-C$_6$ alkyl)phenyl or thiophenyl;
R$^5$ represents hydrogen, —C$_1$-C$_6$ alkyl, —C$_2$-C$_6$ alkenyl, —C$_2$-C$_6$ alkynyl, —COC$_1$-C$_6$ alkyl, CO$_2$C$_1$-C$_6$ alkyl, —(COC$_1$-C$_6$ alkyl)phenyl, —(-CO$_2$C$_1$-C$_6$ alkyl)phenyl, —(C$_1$-C$_6$ alkyl)OC$_1$-C$_6$ alkyl, —(C$_1$-C$_6$ alkyl)SC$_1$-C$_6$ alkyl, —(C$_1$-C$_6$ alkyl)CO$_2$C$_1$-C$_6$ alkyl, —C$_3$-C$_8$ cycloalkyl, —C$_4$-C$_8$ cycloalkenyl or a group —D wherein D represents a group:

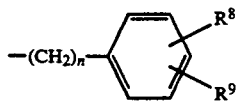

wherein n is an integer from 0 to 3, and each of $R^8$ and $R^9$ is independently hydrogen, $-C_1-C_6$ alkyl, $-C_2-C_6$ alkenyl, $-C_2-C_6$ alkynyl, halogen, $-CN$, $-CO_2H$, $CO_2C_1-C_6$ alkyl, $-CONH_2$, $-CONH-C_1-C_6$ alkyl, $-CONH(C_1-C_6$ alkyl)2, $-CHO$, $-CH_2OH$, $CF_3$, $-OC_1-C_6$ alkyl, $-SC_1-C_6$ alkyl, $-SCC_1-C_6$ alkyl, $-SO_2C_1-C_6$ alkyl, $-NH_2$ or $-NHCOMe$;

each of $R^6$ and $R^7$ independently represents hydrogen, halogen, $-C_1-C_6$ alkyl optionally substituted by one or more halogen atoms, $-C_2-C_6$ alkenyl, $-C_2-C_6$ alkynyl, $-(C_1-C_6$ alkyl)$CO_2C_1-C_6$ alkyl, $-(C_1-C_6$ alkyl)$SC_1-C_6$ alkyl, $-(C_1-C_6$ alkyl)$OC_1-C_6$ alkyl, $-(C_1-C_6$ alkyl)$N(C_1-C_6$ alkyl)$_2$, $-C_3-C_8$ cycloalkyl, $-C_4-C_8$ cycloalkenyl, $-(C_1-C_6$ alkyl)$C_3-C_8$ cycloalkyl, $-(C_1-C_6$ alkyl)$C_4-C_8$ cycloalkenyl, $-(C_1-C_6$ alkyl)$OC_3-C_8$ cycloalkyl, $-(C_1-C_6$ alkyl)$OC_4-C_8$ cycloalkenyl, $-(C_1-C_6$ alkyl)$SC_3-C_8$ cycloalkyl, $-(C_1-C_6$ alkyl)$SC_4-C_8$ cycloalkenyl, a side chain of a naturally occurring amino acid, a group $-D$ as defined above or a $-(C_1-C_6$ alkyl)$OD$ group wherein D is as defined above;

or $R^6$ together with $R^5$ and the atoms to which they are attached form a 5 to 8 membered nitrogen-containing heterocyclic ring;

or $R^6$ and $R^7$ together with the carbon atom to which they are attached form a $C_3-C_8$ cycloalkyl ring;

B represents a) a $-ZR^{10}$ group wherein Z is $-C(O)-$, $-C(=O)O-$, $-C(=S)-$ or $-C(=S)O-$ and $R^{10}$ is $-C_1-C_{18}$ alkyl optionally substituted by one or more halogen atoms, $-C_2-C_{18}$ alkenyl, $-C_2-C_{18}$ alkynyl, $-(C_1-C_6$ alkyl)$OC_1-C_6$ alkyl, $-(C_1-C_6$ alkyl)$SC_1-C_6$ alkyl, $-(C_1-C_6$ alkyl)$O(C_1-C_6$ alkyl)$OC_1-C_6$ alkyl, $-C_3-C_8$ cycloalkyl, $-C_4-C_8$ cycloalkenyl, pyridyl, a group $-D$ as defined above or a $-(C_1-C_6$ alkyl)$OD$ group wherein D is as defined above;

b) a $-CONR^{11}R^{12}$ group wherein each of $R^{11}$ and $R^{12}$ is independently hydrogen, $-C_1-C_{18}$ alkyl optionally substituted by one or more halogen atoms, $-C_2-C_{18}$ alkenyl, $-C_2-C_{18}$ alkynyl, $-C_3-C_8$ cycloalkyl, $-C_4-C_8$ cycloalkenyl, pyridyl, a group $-D$ as defined above or $R^{11}$ and $R^{12}$ together with the nitrogen atom to which they are attached form a 5 to 8 membered nitrogen-containing heterocyclic ring;

or a pharmaceutically or veterinarily acceptable acid addition salt or hydrate thereof.

2. A compound as claimed in claim 1, in which $A^1$ represents $=N-$, $=CH-$ or $=CR^1-$.

3. A compound as claimed in claim 2, in which $A^2$ represents $-N=$, $-CH=$ or $-CR^2=$.

4. A compound as claimed in claim 3, wherein R represents a halogen atom or a hydrogen atom.

5. A compound as claimed in claim 4, wherein $R^1$ represents a halogen atom or a hydrogen atom.

6. A compound as claimed in claim 5, wherein $R^2$ represents halogen atom or a hydrogen atom.

7. A compound as claimed in claim 6, wherein $R^3$ represents a hydrogen atom or a $-C_1-C_6$ alkyl group.

8. A compound as claimed in claim 7, wherein $R^4$ represents a hydrogen atom.

9. A compound as claimed in claim 8, wherein $R^5$ represents a hydrogen atom, a $-C_1-C_6$ alkyl group, a $-C_2-C_6$ alkenyl group, a $-COC_1-C_6$ alkyl group, a $CO_2C_1-C_6$ alkyl group or a $-(C_1-C_6$ alkyl)$CO_2C_1-C_6$ alkyl group.

10. A compound as claimed in claim 9, wherein $R^6$ represents a hydrogen atom, a $-C_1-C_6$ alkyl group, a $-C_2-C_6$ alkenyl group, a $-(C_1-C_6$ alkyl)$CO_2C_1-C_6$ alkyl group, $-(C_1-C_6$ alkyl)$SC_1-C_6$ alkyl group, a side chain of a naturally occurring amino acid, a group D or a $-(C_1-C_6$ alkyl)$OD$ group, or $R^5$ and $R^6$, and the atoms to which they are attached form a 5 to 8 membered nitrogen-containing heterocyclic ring.

11. A compound as claimed in claim 10, wherein $R^7$ represents a hydrogen atom, a $-C_1-C_6$ alkyl group or together with $R^6$ and the carbon atom to which they are attached forms a $C_3-C_8$ cycloalkyl ring.

12. A compound as claimed in claim 11, wherein $R^6$ represents the side chain of a naturally occurring amino acid and the stereochemistry of the carbon to which $R^6$ and $R^7$ are attached is the same as that of the naturally occurring amino acid.

13. A compound; as claimed in claim 12, wherein n represents an integer of 0 or 1.

14. A compound as claimed in claim 13, wherein $R^8$ represents a hydrogen atom or a $-C_1-C_6$ alkyl group.

15. A compound as claimed in claim 14, wherein $R^9$ represents a hydrogen atom.

16. A compound as claimed in claim 15, wherein Z represents a $-C(=O)-$ group or a $-C(=O)O-$ group.

17. A compound as claimed in claim 16, wherein $R^{10}$ represents a $-C_1-C_{18}$ alkyl group, a $-C_2-C_{18}$ alkenyl group, a $-(C_1-C_6$ alkyl)$OC_1-C_6$ alkyl group, a $-(C_1-C_6$ alkyl)$O(C_1-C_6$ alkyl)$OC_1-C_6$ alkyl group, a group D or a $-(C_1-C_6$ alkyl)$OD$ group.

18. A compound as claimed in claim 10, wherein $R^{11}$ represents a $-C_1-C_6$ alkyl group or a pyridyl group.

19. N-4-(1H-2-Methylbenzimidazol-1-methyl)phenylsulphonylglycine methyl ester,

N-4-(1H-2-Methylbenzimidazol-1-ylmethyl)phenylsulphonyl-2,2-dimethylglycine methyl ester, N-4-(1H-2-Methylbenzimidazol-1-ylmethyl)phenylsulphonyl-1-aminocyclohexanecarboxylic acid methyl ester, N-4-(1H-2-Methylbenzimidazol-1-methyl)phenylsulphonyl-L-2-phenylglycine methyl ester, N-4-(1H-2-Methylbenzimidazol-1-ylmethyl)phenylsulphonyl-L-valine methyl ester, N-4-(1H-2-Methylbenzimidazol-1-ylmethyl)phenylsulphonyl-L-isoleucine methyl ester, N-4-(1H-2-Methylbenzimidazol-1-ylmethyl)phenylsulphonyl-L-leucine methyl ester;

N-4-(1H-2-Methylbenzimidazol-1-ylmethyl)phenylsulphonyl—D-leucine methyl ester,

N-4-(1H-2-Methylbenzimidazol-1ylmethyl)phenylsulphonyl-L-norleucine methyl ester, N-4-(1H-2-Methylbenzimidazol-1-ylmethyl)phenylsulphonyl-L-phenylalanine methyl ester, N-4-(1H-2-Methylbenzimidazol-1-ylmethyl)phenylsulphonyl-O-methyl-L-tyrosine methyl ester, N-4-(1H-2-Methylbenzimidazol-1-ylmethyl)phenylsulphonyl-O-benzyl-L-serine methyl ester, N-4-(1H-2-Methylbenzimidazol-1-ylmethyl)phenylsulphonyl-L-methionine methyl ester, N-4-(1H-2-Methylbenzimidazol-1-ylmethyl)phenylsulphonyl-L-leucine ethyl ester,
N-4-(1H-2-Methylbenzimidazol1-ylmethyl)phenylsulphonyl-L-phenylalanine ethyl ester,
N-4-(1H-2-Methylbenzimidazol-1-ylmethyl)phenylsulphonyl-L-methionine ethyl ester,
N-4-(1H-2-Methylbenzimidazol-1-ylmethyl)phenylsulphonyl-L-aspartic acid diethyl ester,
N-4-(1H-2-Methylbenzimidazol-1-ylmethyl)phenylsulphonyl-L-leucine isopropyl ester,
N-4-(1H-2-Methylbenzimidazol-1-ylmethyl)phenylsulphonyl-L-leucine n-butyl ester,
N-4-(1H-2-Methylbenzimidazol-1-ylmethyl)phenylsulphonyl-L-alanine tert-butyl ester,
N-4-(1H-2-Methylbenzimidazol-1-ylmethyl)phenylsulphonyl-L-phenylalanine tert-butyl ester,
N-4-(1H-2-Methylbenzimidazol-1-ylmethyl)phenylsulphonyl-L-leucine benzyl ester,
N-4-(1H-2-Methylbenzimidazol-1-ylmethyl)phenylsulphonyl-L-phenylalanine benzyl ester,
N-4-(1H-2-Methylbenzimidazol-1-ylmethyl)phenylsulphonyl-L-isoleucine methylamide,
N-4-(1H-2-Methylbenzimidazol-1-ylmethyl)phenylsulphonyl-L-phenylalanine methylamide,
N-4-(1H-2-Methylbenzimidazol-1-ylmethyl)phenylsulphonyl-L-phenylalanine 2-pyridylamide,
N-4-(1H-2-Methylbenzimidazol-1-ylmethyl)phenylsulphonyl-L-phenylalanine morpholinoamide,
N-4-(1H-2-Methylbenzimidazol-1-ylmethyl)phenylsulphonyl-L-leucine pyrrolidinoamide,
N-4-(1H-2-Methylbenzimidazol-1-ylmethyl)phenylsulphonyl-L-prolinyl methyl ester,
N-4-(1H-2-Methylbenzimidazol-1-ylmethyl)phenylsulphonyl-L-prolinyl benzyl ester,
N-4-(3H-Imidazo[4,5-c]pyrid-3-ylmethyl)phenylsulphonyl-L-leucine methyl ester,
N-4-(1H-Imidazo[4,5-c]pyrid-1-ylmethyl)phenylsulphonyl-L-leucine methyl ester,
N-4-(3H-2-Methylimidazo[4,5-c]pyrid-3-ylmethyl)phenylsulphonyl-L-leucine methyl ester,
N-4-(1H-2-Methylimidazo[4,5-c]pyrid-1-ylmethyl)phenylsulphonyl-L-leucine methyl ester,
N-4-(3H-Imidazo[4,5-c)pyrid-1-ylmethyl)phenylsulphonyl-L-phenylalanine methyl ester,
N-4-(1H-Imidazo[4,5-c)pyrid-3-ylmethyl)phenylsulphonyl-L-phenylalanine methyl ester,
N-4-(3H-Imidazo[4,5-c)pyrid-3-ylmethyl)phenylsulphonyl-O-benzyl-L-serine methyl ester,
N-4-(1H-imidazo[4,5-c]pyrid-1-ylmethyl)phenylsulphonyl-0-benzyl-L-serine methyl ester,
N-4-(3H-2-Methylimidazo[4,5-c]pyrid-3-ylmethyl)-phenylsulphonyl-L-leucine ethyl ester,
N-4-(1H-2-Methylimidazo[4,5-c]pyrid-1-ylmethyl)-phenylsulphonyl-L-leucine ethyl ester,
N-4-(3H-2-Methylimidazo[4,5-c]pyrid-3-ylmethyl)-phenylsulphonyl-L-leucine n-propyl ester,
N-4-(1H-2-Methylimidazo[4,5-c]pyrid-1-ylmethyl)-phenylsulphonyl-L-leucine n-propyl ester,
N-4-(3H-2-Methylimidazo[4,5-c]pyrid-3-ylmethyl)-phenylsulphonyl-L-leucine allyl ester,
N-4-(1H-2-Methylimidazo[4,5-c]pyrid-1-ylmethyl)-phenylsulphonyl-L-leucine allyl ester,
N-4-(3H-2-Methylimidazo[4,5-c]pyrid-3-ylmethyl)-phenylsulphonyl-L-leucine i-propyl ester,
N-4-(1H-2-Methylimidazo[4,5-c]pyrid-1-ylmethyl)-phenylsulphonyl-L-leucine i-propyl ester,
N-4-(3H-2-Methylimidazo[4,5-c]pyrid-3-ylmethyl)-phenylsulphonyl-L-leucine n-butyl ester,
N-4-(1H-2-Methylimidazo[4,5-c]pyrid-1-ylmethyl)-phenylsulphonyl-L-leucine n-butyl ester,
N-4-(3H-2-Methylimidazo[4,5-c]pyrid-3-ylmethyl)-phenylsulphonyl-L-leucine 1-methylpropyl ester,
N-4-(1H-2-Methylimidazo[4,5-c]pyrid-1-ylmethyl)-phenylsulphonyl-L-leucine 1-methylpropyl ester,
N-4-(3H-2-Methylimidazo[4,5-c]pyrid-3-ylmethyl)-phenylsulphonyl-L-leucine benzyl ester,
N-4-(1H-2-Methylimidazo[4,5-c]pyrid-1-ylmethyl)-phenylsulphonyl-L-leucine benzyl ester,
N-4-(3H-2-Methylimidazo[4,5-c]pyrid-3-ylmethyl)-phenylsulphonyl-L-leucine 2-ethoxyethyl ester,
N-4-(1H-2-Methylimidazo[4,5-c]pyrid-1-ylmethyl)-phenylsulphonyl-L-leucine 2-ethoxyethyl ester,
N-4-(3H-2-Methylimidazo[4,5-c]pyrid-3-ylmethyl)-phenylsulphonyl-L-leucine 2-benzoxyethyl ester,
N-4-(1H-2-Methylimidazo[4,5-c]pyrid-1-ylmethyl)-phenylsulphonyl-L-leucine 2-benzoxyethyl ester,
N-4-(3H-2-Methylimidazo[4,5-c]pyrid-3-ylmethyl)-phenylsulphonyl-L-leucine 1-methyl-2-methoxyethyl ester,
N-4-(1H-2-Methylimidazo[4,5-c]pyrid-1ylmethyl)-phenylsulphonyl-L-leucine 1-methyl-2-methoxyethyl ester,
N-4-(3H-2-Methylimidazo[4,5-c]pyrid-3-ylmethyl)-phenylsulphonyl-L-leucine 2-(2-ethoxyethoxy)ethyl ester,
N-4-(1H-2-Methylimidazo[4,5-c]pyrid-1-ylmethyl)-phenylsulphonyl-L-leucine 2-(2-ethoxyethoxy)ethyl ester,
N-4-(3H-2-Methylimidazo[4,5-c]pyrid-3-ylmethyl)-phenylsulphonyl-D,L-allylglycine ethyl ester,
N-4-(1H-2-Methylimidazo[4,5-c]pyrid-1-ylmethyl)-phenylsulphonyl—D,L-allylglycine ethyl ester,
N-4-(3H-2-Methylimidazo[4,5-c]pyrid-3-ylmethyl)-phenylsulphonyl-L-methionine ethyl ester,
N-4-(1H-2-Methylimidazo[4,5-c]pyrid-1-ylmethyl)-phenylsulphonyl-L-methionine ethyl ester,
N-4-(1H-2-Methyl-5-fluorobenzimidazol-1-ylmethyl)-phenylsulphonyl-L-leucine methyl ester,
N-4-(1H-2-Methyl-6-fluorobenzimidazol-1-ylmethyl)-phenylsulphonyl-L-leucine methyl ester,
N-4-(1H-2-Methyl-5-fluorobenzimidazol-1-ylmethyl)-phenylsulphonyl-L-leucine ethyl ester,
N-4-(1H-2-Methyl-6-fluorobenzimidazol-1-ylmethyl)-phenylsulphonyl-L-leucine ethyl ester,
N-4-(1H-2-Methylbenzimidazol-1-ylmethyl)phenylsulphonyl-2-keto-3-amino-4-methylpentane,
N-4-(3H-2-Methylimidazo[4,5-c]pyrid-3-ylmethyl)-phenylsulphonyl-2-keto-3-amino-4-methylpentane,
N-4-(1H-2-methylimidazo[4,5-c]pyrid-1-ylmethyl)-phenylsulphonyl-2-keto-3-amino-4-methylpentane,
N-Methyl-N-4-(1H-2-methylbenzimidazol-1-ylmethyl)-phenylsulphonyl-L-leucine methyl ester,
Methyl-N-4-(3H-2-methylimidazo[4,5-c]pyrid-3-ylmethyl)phenylsulphonyl-L-leucine ethyl ester,
N-Methyl-N-4-(1H-2-methylimidazo[4,5-c]pyrid-1-ylmethyl)phenylsulphonyl-L-leucine ethyl ester,
N-Methyl-N-4-(1H-2-methylbenzimidazol-1-ylmethyl)-phenylsulphonyl-L-leucine ethyl ester,
N-Methyl-N-4-(3H-imidazo[4,5-c]pyrid-3-ylmethyl)-phenylsulphonyl-L-leucine ethyl ester,
N-Methyl-N-4-(1H-imidazo[4,5-c]pyrid-1-ylmethyl)-phenylsulphonyl-L-leucine ethyl ester,
N-Methyl-N-4-(3H-2-methylimidazo[4,5-c]pyrid-3-ylmethyl)phenylsulphonyl-L-leucine i-propyl ester,
N-Methyl-N-4-(1H-2-methylimidazo[4,5-c]pyrid-1-ylmethyl)phenylsulphonyl-L-leucine i-propyl ester, N-Methyl-N-4-(3H-2-methylimidazo[4,5-c]pyrid-3-ylmethyl)phenylsulphonyl-L-leucine n-butyl ester,
N-Methyl-N-4-(1H-2-methylimidazo[4,5-c]pyrid-1-ylmethyl)phenylsulphonyl-L-leucine n-butyl ester,
N-Methyl-N-4-(3H-2-methylimidazo[4,5-c]pyrid-3-ylmethyl)phenylsulphonyl-L-leucine benzyl ester,
N-Methyl-N-4-(1H-2-methylimidazo[4,5-c]pyrid-1-ylmethyl)phenylsulphonyl-L-leucine benzyl ester,
N-Allyl-N-4-(3H-imidazo[4,5-c]pyrid-3-ylmethyl)-phenylsulphonyl-L-leucine ethyl ester,
N-Allyl-N-4-(1H-imidazo[4,5-c]pyrid-1-ylmethyl)-phenylsulphonyl-L-leucine ethyl ester,
N-Allyl-N-4-(3H-2-methylimidazo[4,5-c]pyrid-3-ylmethyl)phenylsulphonyl-L-leucine ethyl ester,
N-Allyl-N-4-(1H-2-methylimidazo[4,5-c]pyrid-1-ylmethyl)phenylsulphonyl-L-leucine ethyl ester,
N-Methyl-N-4-(3H-2-methylimidazo[4,5-c]pyrid-3-ylmethyl)phenylsulphonyl-D,L-allylglycine methyl ester,
N-Methyl-N-4-(1H-2-methylimidazo[4,5-c]pyrid-1-ylmethyl)phenylsulphonyl-D,L-allylglycine methyl ester,
N-Methyl-N-4-(3H-2-methylimidazo[4,5-c]pyrid-3-ylmethyl)phenylsulphonyl-D,L-allylglycine ethyl ester,
N-Methyl-N-4-(1H-2-methylimidazo[4,5-c]pyrid-1-ylmethyl)phenylsulphonyl-D,L-allylglycine ethyl ester,
N-Methyl-N-4-(3H-2-methylimidazo[4,5-c]pyrid-3-ylmethyl)phenylsulphonyl-L-isoleucine allyl ester,
N-methyl-N-4-(1H-2-methylimidazo[4,5-c]pyrid-1ylmethyl)phenylsulphonyl-L-isoleucine allyl ester,
N-Methyl-N-4-(3H-2-methylimidazo[4,5-c]pyrid-3-ylmethyl)phenylsulphonyl-L-leucine morpholinoamide,
N-Methyl-N-4-(1H-2-methylimidazo[4,5-c]pyrid-1ylmethyl)phenylsulphonyl-L-leucine morpholinoamide,
N-Propyl-N-4-(3H-imidazo[4,5-c]pyrid-3-ylmethyl)-phenylsulphonyl-L-leucine ethyl ester,
N-Propyl-N-4-(3H-2-methylimidazo[4,5-c]pyrid-3ylmethyl)phenylsulphonyl-L-leucine ethyl ester,
N-Propyl-N-4-(1H-2-methylimidazo[4,5-c]pyrid-1-ylmethyl)phenylsulphonyl-L-leucine ethyl ester,
N-Methyl-N-4-(3H-2-methylimidazo[4,5-c]pyrid-3-ylmethyl)phenylsulphonyl-2-keto-3-amino-4-methylpentane,
N-Methyl-N-4-(1H-2-methylimidazo[4,5-c]pyrid-1-ylmethyl)phenylsulphonyl-2-keto-3-amino-4-methylpentane,
N-t-Butoxycarbonylmethyl-N-4-(3H-2-methylimidazo[4,5-c]pyrid-3-ylmethyl)phenylsulphonyl-L-leucine ethyl ester,
N-t-Butoxycarbonylmethyl-N-4-(1H-2-methylimidazo[4,5-c]pyrid-1-ylmethyl)phenylsulphonyl-L-leucine ethyl ester,
N-Ethoxycarbonylmethyl-N-4-(3H-2-methylimidazo[4,5-c]pyrid-3-ylmethyl)phenylsulphonyl-L-leucine ethyl ester,
N-Methoxycarbonylmethyl-N-4-(3H-2-methylimidazo[4,5-c]pyrid-1-ylmethyl)phenylsulphonyl-L-leucine ethyl ester,
N-Methoxycarbonylmethyl-N-4-(1H-2-methylimidazo[4,5-c]pyrid-3-ylmethyl)phenylsulphonyl-L-leucine ethyl ester,
N-Methyl-N-3-chloro-4-(3H-2-methylimidazo[4,5-c]pyrid-1-ylmethyl)phenylsulphonyl-L-leucine ethyl ester,
N-Methyl-N-3-chloro-4-(1H-2-methylimidazo[4,5-c]pyrid-1-ylmethyl)phenylsulphonyl-L-leucine ethyl ester,
N-Methyl-N-4-(1H-2-ethylimidazo[4,5-c]pyrid-1-ylmethyl)phenylsulphonyl-L-leucine ethyl ester,
N-Methyl-N-4-(1H-2-n-pentylimidazo[4,5-c]pyrid-1-ylmethyl)phenylsulphonyl-L-leucine ethyl ester,
N-Acetyl-N-4-(3H-2-methylimidazo[4,5-c]pyrid-3-ylmethyl)phenylsulphonyl-L-leucine ethyl ester,
N-Ethoxycarbonyl-N-4-(3H-2-methylimidazo[4,5-c]pyrid-3-ylmethyl)phenylsulphonyl-L-leucine ethyl ester,
N-Ethoxycarbonyl-N-4-(1H-2-methylimidazo[4,5-c]pyrid-1-ylmethyl)phenylsulphonyl-L-leucine ethyl ester,
N-Methyl-N-4-(1H-2-methylimidazo[4,5-c]pyrid-1-ylmethyl)phenylsulphonyl-L-leucine octadecyl ester,
or a salt of such a compound.

20. A pharmaceutical or veterinary composition comprising a compound as claimed in claim 1 and a pharmaceutically and/or veterinarily acceptable carrier.

* * * * *

UNITED STATES PATENT AND TRADEMARK OFFICE
CERTIFICATE OF CORRECTION

PATENT NO. : 5,200,412
DATED : Apr. 6, 1993
INVENTOR(S) : Mark Whittaker, Andrew Miller It is certified that error appears in the above-identified patent and that said Letters Patent is hereby corrected as shown below:

On the cover page, item, [75], delete

"Mark Whittaker; Andrew Miller, both of Oxfordshire, England"

and insert

-- Mark Whittaker, of Oxfordshire; Andrew Miller of Oxford; and Stephen A. Bowles, of Hertfordshire, all of England --.

Signed and Sealed this

Fourteenth Day of September, 1993

Attest:

BRUCE LEHMAN

*Attesting Officer*  *Commissioner of Patents and Trademarks*